(12) United States Patent
Buettelmann et al.

(10) Patent No.: US 7,414,061 B2
(45) Date of Patent: Aug. 19, 2008

(54) ARYL-ISOXAZOL-4-YL-IMIDAZOLE DERIVATIVES

(75) Inventors: Bernd Buettelmann, Schopfheim (DE); Bo Han, Shanghai (CN); Henner Knust, Rheinfelden (DE); Andrew Thomas, Binningen (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 51 days.

(21) Appl. No.: 11/640,622

(22) Filed: Dec. 18, 2006

(65) Prior Publication Data
US 2007/0161654 A1 Jul. 12, 2007

(30) Foreign Application Priority Data
Dec. 27, 2005 (EP) ................... 05113011

(51) Int. Cl.
A61K 31/506 (2006.01)
A61K 31/4439 (2006.01)
A61K 31/42 (2006.01)
C07D 413/14 (2006.01)

(52) U.S. Cl. ............ 514/256; 514/341; 514/378; 544/333; 546/272.1; 548/247

(58) Field of Classification Search ............ 514/256, 514/341, 378; 544/333; 546/272.1; 548/247
See application file for complete search history.

(56) References Cited

U.S. PATENT DOCUMENTS

| | | | |
|---|---|---|---|
| 2004/0006226 A1 | 1/2004 | Ladduwahetty et al. | |
| 2007/0191421 A1* | 8/2007 | Buettelmann et al. | 514/303 |

FOREIGN PATENT DOCUMENTS

| WO | WO 01/29015 | 4/2001 |
|---|---|---|
| WO | WO 02/50062 A2 | 6/2002 |
| WO | WO 02/081474 A1 | 10/2002 |
| WO | WO 03/004027 | 1/2003 |
| WO | WO 2004/022555 A1 | 3/2004 |
| WO | WO 2005/123672 A2 | 12/2005 |
| WO | WO 2007/071598 A1 | 6/2007 |
| WO | WO 2007/074089 A1 | 7/2007 |

OTHER PUBLICATIONS

U.S. Appl. No. 11/543,178, filed Oct. 4, 2006, pending.
U.S. Appl. No. 11/590,571, filed Oct. 31, 2006, pending.
U.S. Appl. No. 11/520,394, filed Sep. 13, 2006, pending.
McNamara et al., Psychobiology (1993), vol. 21, pp. 101-108.
Lam et al., Bioorganic & Medicinal Chemistry Letters (2003) vol. 13(10) pp. 1795-1799.
Wang et al., Journal of Fluorine Chemistry, vol. 111(2) pp. 241-246 (2001).
Roy et al., Synthesis, 2003 pp. 1347-1356.
White, et al., Journal of Organic Chemistry (1981), vol. 46(11) pp. 2273-2280.
Shi Shun et al., J. Org. chem. vol. 68 (2003) pp. 6810-6813.
Burke, et al., Journal of Natural Products, 1986, vol. 49, pp. 522-523.
Hamper et al., J. Agric. Food Chem. (1995), vol. 43, pp. 219-228.
Kumar, et al., Tetrahedron Letters, vol. 47, (2006), p. 1457-1460.
Hormi, Organic Syntheses, vol. 8, p. 247 (1993) & vol. 66, (1988), p. 173.

\* cited by examiner

*Primary Examiner*—Kamal A Saeed
(74) *Attorney, Agent, or Firm*—George W. Johnston; Patricia S. Rocha-Tramaloni; Kimberly J. Prior

(57) ABSTRACT

The present invention is concerned with aryl-isoxazol-4-yl-imidazole derivatives of formula I:

wherein
$R^1$ to $R^6$ are as defined in the specification and pharmaceutically acceptable acid addition salts thereof.

This class of compounds has high affinity and selectivity for GABA A α5 receptor binding sites and might be useful as cognitive enhancer or for the treatment of cognitive disorders like Alzheimer's disease.

36 Claims, No Drawings

ARYL-ISOXAZOL-4-YL-IMIDAZOLE DERIVATIVES

PRIORITY TO RELATED APPLICATIONS

This application claims the benefit of European Application No. 05113011.0, filed Dec. 27, 2005, which is hereby incorporated by reference in its entirety.

BACKGROUND OF THE INVENTION

Receptors for the major inhibitory neurotransmitter, gamma-aminobutyric acid (GABA), are divided into two main classes: (1) GABA A receptors, which are members of the ligand-gated ion channel superfamily and (2) GABA B receptors, which are members of the G-protein linked receptor family. The GABA A receptor complex which is a membrane-bound heteropentameric protein polymer is composed principally of α, β and γ subunits.

Presently a total number of 21 subunits of the GABA A receptor have been cloned and sequenced. Three types of subunits (α, β and γ) are required for the construction of recombinant GABA A receptors which most closely mimic the biochemical, electrophysiological and pharmacological functions of native GABA A receptors obtained from mammalian brain cells. There is strong evidence that the benzodiazepine binding site lies between the α and γ subunits. Among the recombinant GABA A receptors, α1β2γ2 mimics many effects of the classical type-I BzR subtypes, whereas α2β2γ2, α3β2γ2 and α5β2γ2 ion channels are termed type-II BzR.

It has been shown by McNamara and Skelton in *Psychobiology*, 21:101-108 that the benzodiazepine receptor inverse agonist β-CCM enhance spatial learning in the Morris watermaze. However, β-CCM and other conventional benzodiazepine receptor inverse agonists are proconvulsant or convulsant which prevents their use as cognition enhancing agents in humans. In addition, these compounds are non-selective within the GABA A receptor subunits, whereas a GABA A α5 receptor partial or full inverse agonist which is relatively free of activity at GABA A α1 and/or α2 and/or α3 receptor binding sites can be used to provide a medicament which is useful for enhancing cognition with reduced or without proconvulsant activity. It is also possible to use GABA A α5 inverse agonists which are not free of activity at GABA A α1 and/or α2 and/or α3 receptor binding sites but which are functionally selective for α5 containing subunits. However, inverse agonists which are selective for GABA A α5 subunits and are relatively free of activity at GABA A α1, α2 and α3 receptor binding sites are preferred.

SUMMARY OF THE INVENTION

The present invention provides aryl-isoxazol-4-yl-imidazole derivatives of formula I

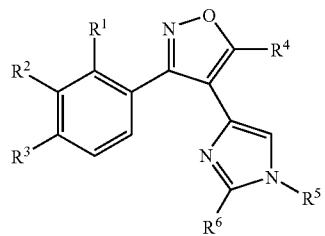

I wherein
$R^1$, $R^2$, and $R^3$ are each independently hydrogen or halogen;
$R^4$ is hydrogen, lower alkyl, cycloalkyl, —$(CH_2)_n$—O-lower alkyl or lower alkyl substituted by hydroxy;
$R^5$ is —$(CH_2)_m$-aryl or —$(CH_2)_m$-heteroaryl each of which is optionally substituted by one or more substituent selected from the group consisting of halogen, cyano, nitro, lower alkyl, lower alkoxy, lower alkylsulfanyl, lower alkyl substituted by halogen, —C(O)-lower alkyl, —C(O)—O-lower alkyl, —NH—C(O)—O-lower alkyl and —C(O)—NH—R', wherein
R' is lower alkynyl or is lower alkyl substituted by halogen, or is —$(CH_2)_n$-cycloalkyl, —$(CH_2)_n$-heterocyclyl, —$(CH_2)_n$-heteroaryl or —$(CH_2)_n$-aryl, each of which is optionally substituted by halogen;
$R^6$ is hydrogen,
—C(O)H,
—$(CH_2)_n$—O-lower alkyl,
—C(O)O-lower alkyl,
lower alkyl substituted by hydroxy or halogen,
cycloalkyl,
aryl,
—$(CH_2)_n$—O—$CH_2$-aryl optionally substituted by halogen or lower alkyl,
—$(CH_2)_n$—O—$CH_2$-heteroaryl optionally substituted by halogen, lower alkyl or lower alkyl substituted by halogen, or
—$(CH_2)_n$—NH—$(CH_2)_o$-heterocyclyl;
n is 0, 1, 2 or 3
m is 0 or 1; and
o is 1, 2 or 3;

and pharmaceutically acceptable acid addition salts thereof.

The present invention also provides pharmaceutical compositions containing a therapeutically effective amount of a compound of the invention and a pharmaceutically acceptable carrier. The invention further provides processes for the manufacture of compounds of the invention and pharmaceutical compositions containing them.

This class of compounds have high affinity and selectivity for GABA A α5 receptor binding sites and might be useful as cognitive enhancer or for the treatment of cognitive disorders like Alzheimer's disease. Thus, the invention also provides methods for enhancing cognition and for treating cognitive disorders, such as Alzheimer's disease, which comprise administering to an individual a therapeutically effective amount of a compound of formula I or a pharmaceutically acceptable salt thereof.

The most preferred indication in accordance with the present invention is Alzheimer's disease.

DETAILED DESCRIPTION OF THE INVENTION

The following definitions of the general terms used in the present description apply irrespective of whether the terms in question appear alone or in combination. It must be noted that, as used in the specification and the appended claims, the singular forms "a", "an," and "the" include plural forms unless the context clearly dictates otherwise.

As used herein, the term "lower alkyl" denotes a straight- or branched-chain hydrocarbon group containing from 1-7, preferably from 1-4, carbon atoms, for example, methyl, ethyl, propyl, isopropyl, n-butyl, i-butyl, t-butyl and the like.

The term "lower alkyl substituted by halogen" denotes a lower alkyl group as defined hereinabove which is substituted by one or more, preferably one, two or three halogen atom(s), i.e. chlorine, iodine, fluorine or bromine. Most preferred is $CF_3$.

The term "lower alkyl substituted by hydroxy" denotes a lower alkyl group as defined hereinabove which is substituted by one or more, hydroxy group(s), The term "lower alkoxy" denotes a lower alkyl group as defined hereinabove, linked via an oxygen atom. Examples of lower alkoxy are methoxy or ethoxy and the like.

The term "lower alkylsulfanyl" denotes a lower alkyl group as defined hereinabove, linked via a sulfur atom. Examples of lower alkoxy are methylsulfanyl or ethylsulfanyl and the like.

The term "lower alkynyl" denotes a straight-chain or branched unsaturated hydrocarbon residue with 2-6, preferably 2-4, carbon atoms, such as ethynyl, n-propynyl, and the like.

The term "aryl" denotes an unsaturated aromatic carbon ring, for example a phenyl, benzyl or naphthyl group. A preferred aryl group is phenyl.

The term "halogen" denotes chlorine, iodine, fluorine and bromine.

The term "cycloalkyl" denotes a cyclic hydrocarbon ring, having from 3 to 7 carbon ring atoms, for example, cyclopropyl, cyclopentyl or cyclohexyl.

The term "heteroaryl" denotes an aromatic 5 or 6 membered ring containing from one to three heteroatoms, such as N, O or S atoms with the remaining ring atoms being carbon. Examples of such aromatic heteroaryl groups are pyridinyl, pyrimidinyl, triazolyl, isoxazolyl, furanyl, thiophenyl, imidazolyl, oxazolyl and pyrazinyl.

The term "heterocyclyl" denotes a non-aromatic 5 or 6 membered ring containing from one to three heteroatoms, such as N, O or S atoms with the remaining ring atoms being carbon. Examples of such non-aromatic heterocyclyl groups are morpholinyl or tetrahydro-pyranyl.

"Pharmaceutically acceptable," such as pharmaceutically acceptable carrier, excipient, etc., means pharmacologically acceptable and substantially non-toxic to the subject to which the particular compound is administered.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluene-sulfonic acid and the like.

"Therapeutically effective amount" means an amount that is effective to prevent, alleviate or ameliorate symptoms of disease or prolong the survival of the subject being treated.

The present invention provides aryl-isoxazol-4-yl-imidazole derivatives of formula I

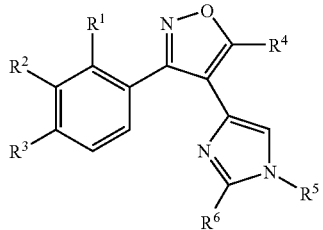

wherein
$R^1$ $R^2$, and $R^3$ are each independently hydrogen or halogen;
$R^4$ is hydrogen, lower alkyl, cycloalkyl, —$(CH_2)_n$—O-lower alkyl or lower alkyl substituted by hydroxy;
$R^5$ is —$(CH_2)_m$-aryl or —$(CH_2)_m$-heteroaryl each of which is optionally substituted by one or more substituent selected from the group consisting of halogen, cyano, nitro, lower alkyl, lower alkoxy, lower alkylsulfanyl, lower alkyl substituted by halogen, —C(O)-lower alkyl, —C(O)—O-lower alkyl, —NH—C(O)—O-lower alkyl and —C(O)—NH—R', wherein
R' is lower alkynyl or is lower alkyl substituted by halogen, or is —$(CH_2)_n$-cycloalkyl, —$(CH_2)_n$-heterocyclyl, —$(CH_2)_n$-heteroaryl or —$(CH_2)_n$-aryl, each of which is optionally substituted by halogen;
$R^6$ is hydrogen,
—C(O)H,
—$(CH_2)_n$—O-lower alkyl,
—C(O)O-lower alkyl,
lower alkyl substituted by hydroxy or halogen,
cycloalkyl, aryl,
—$(CH_2)_n$—O—$CH_2$-aryl optionally substituted by halogen or lower alkyl,
—$(CH_2)_n$—O—$CH_2$-heteroaryl optionally substituted by halogen, lower alkyl or lower alkyl substituted by halogen, or
—$(CH_2)_n$—NH—$(CH_2)_o$-heterocyclyl;
n is 0, 1, 2 or 3
m is 0 or 1; and
o is 1, 2 or 3;

and pharmaceutically acceptable acid addition salts thereof.

Preferred are compounds, which have a binding activity (hKi) of lower than 100 nM and are selective for GABA A α5 subunits and are relatively free of activity at GABA A α1, α2 and α3 receptor binding sites. Most preferred are compounds which have a binding activity (hKi) of lower than 35 nM.

In an embodiment of the present invention are compounds of formula I, wherein
$R^1$, R2, to $R^3$ are each independently hydrogen or halogen;
$R^4$ is hydrogen, or lower alkyl;
$R^5$ is —$(CH_2)_m$-aryl or —$(CH_2)_m$-5 or 6 membered heteroaryl each of which is optionally substituted by one or more halogen, cyano, nitro, lower alkyl, lower alkoxy, lower alkylsulfanyl, lower alkyl substituted by halogen, —(CO)-lower alkyl, —(CO)—O-lower alkyl, —NH—(CO)—O-lower alkyl;
$R^6$ is hydrogen, cycloalkyl, aryl or lower alkyl optionally substituted by lower alkoxy-aryl; and p0 m is 0 or 1;

and pharmaceutically acceptable acid addition salts thereof.

In the compounds of formula I, according to the invention, the following are preferred options for the variables which can appear individually or in any combination in the compounds of formula I:
$R^1$ is preferably hydrogen or F;
$R^2$ is preferably hydrogen, F or Br;
$R^3$ is preferably hydrogen, F or Br;
$R^4$ is preferably hydrogen, methyl, or ethyl;
$R^5$ is —$(CH_2)_m$-aryl (preferably phenyl) or —$(CH_2)_m$-5 or 6 membered heteroaryl (preferably isoxazolyl, pyridinyl or pyrimidinyl) each of which is optionally substituted by one or more halogen (preferably F, Cl or Br), cyano, nitro, lower alkyl (preferably methyl or ethyl), lower alkoxy (preferably methoxy), lower alkylsulfanyl (preferably methylsulfanyl), lower alkyl substituted by halogen (preferably —$CF_3$), —C(O-lower alkyl, —C(O)O-lower alkyl, —NH—C(O)O-lower alkyl or —C(O)—NH—R' and R' is lower alkinyl (preferably propynyl) or is —$(CH_2)_n$-cycloalkyl (preferably cyclopropyl, cyclobutyl, or cyclopentyl), or is —$(CH_2)_n$-heterocyclyl (preferably morpholinyl or tetrahydropyranyl), or is —$(CH_2)_n$-heteroaryl (preferably pyridinyl, imidazolyl, or furanyl) or —$(CH_2)_n$-aryl (preferably phenyl), each of which is optionally substituted by halogen (F);

R⁶ is hydrogen, —C(O)H, —(CH₂)ₙ—O-lower alkyl (preferably methyl), —C(O)O-lower alkyl, lower alkyl substituted by hydroxy or halogen (preferably CH₂OH or CF₃), cycloalkyl (preferably cyclopropyl), aryl (preferably phenyl), —(CH₂)ₙ—O—CH₂-aryl optionally substituted by halogen (F, Cl) or lower alkyl (methyl), —(CH₂)ₙ—O—CH₂-heteroaryl (preferably pyridinyl), optionally substituted by halogen (F), lower alkyl (methyl) or lower alkyl substituted by halogen (CH₃), or —(CH₂)ₙ—NH—(CH₂)ₒ-heterocyclyl (preferably morpholinyl);

m is 0 or 1;
n is 0, 1, 2 or 3; and
o is 1, 2 or 3;

and pharmaceutically acceptable acid addition salts thereof.

In a certain embodiment, the compounds of the invention are those compounds of formula I wherein R⁵ is —(CH₂)ₘ-aryl or —(CH₂)ₘ-5 or 6 membered heteroaryl which is unsubstituted, for example the following compounds:

5-methyl-3-phenyl-4-(1-phenyl-1H-imidazol-4-yl)-isoxazole,
2-[4-(5-methyl-3-phenyl-isoxazol-4-yl)-imidazol-1-yl]-pyridine,
2-[4-(5-Methyl-3-phenyl-isoxazol-4-yl)-imidazol-1-yl]-pyridine,
2-[4-(5-methyl-3-phenyl-isoxazol-4-yl)-imidazol-1-yl]-pyrimidine,
4-(1-benzyl-1H-imidazol-4-yl)-5-methyl-3-phenyl-isoxazole,
2-{4-[3-(2-fluoro-phenyl)-5-methyl-isoxazol-4-yl]-imidazol-1-yl}-pyrimidine,
2-{4-[3-(3-fluoro-phenyl)-5-methyl-isoxazol-4-yl]-imidazol-1-yl}-pyrimidine,
2-{4-[3-(4-fluoro-phenyl)-5-methyl-isoxazol-4-yl]-imidazol-1-yl}-pyrimidine,
2-{4-[3-(4-bromo-phenyl)-5-methyl-isoxazol-4-yl]-imidazol-1-yl}-pyrimidine,
4-(1-benzyl-1H-imidazol-4-yl)-3-(4-bromo-phenyl)-5-methyl-isoxazole,
2-{4-[3-(3,4-difluoro-phenyl)-5-methyl-isoxazol-4-yl]-imidazol-1-yl}-pyrimidine,
2-[2-methyl-4-(5-methyl-3-phenyl-isoxazol-4-yl)-imidazol-1-yl]-pyrimidine,
2-[2-benzyloxymethyl-4-(5-methyl-3-phenyl-isoxazol-4-yl)-imidazol-1-yl]-pyrimidine,
4-(1-benzyl-2-benzyloxymethyl-1H-imidazol-4-yl)-5-methyl-3-phenyl-isoxazole,
4-{4-[3-(4-fluoro-phenyl)-5-methyl-isoxazol-4-yl]-imidazol-1-yl}-pyridine,
3-{4-[3-(4-fluoro-phenyl)-5-methyl-isoxazol-4-yl]-imidazol-1-yl}-pyridine,
[3-phenyl-4-(1-phenyl-1H-imidazol-4-yl)-isoxazol-5-yl]-methanol,
4-(5-methyl-3-phenyl-isoxazol-4-yl)-1-phenyl-1H-imidazole-2-carboxylic acid methyl ester and
4-(2-benzyloxymethyl-1-phenyl-1H-imidazol-4-yl)-5-methyl-3-phenyl-isoxazole.

In a certain embodiment, the compounds of the invention are those compounds of formula I wherein R⁵ is —(CH₂)ₘ-aryl or —(CH₂)ₘ-5 or 6 membered heteroaryl which is substituted by one or more halogen, for example the following compounds:

4-[1-(4-fluoro-phenyl)-1H-imidazol-4-yl]-5-methyl-3-phenyl-isoxazole,
4-[1-(3-fluoro-phenyl)-1H-imidazol-4-yl]-5-methyl-3-phenyl-isoxazole,
4-[1-(3-chloro-phenyl)-1H-imidazol-4-yl]-5-methyl-3-phenyl-isoxazole,
4-[1-(4-bromo-phenyl)-1H-imidazol-4-yl]-5-methyl-3-phenyl-isoxazole,
4-[1-(3-bromo-phenyl)-1H-imidazol-4-yl]-5-methyl-3-phenyl-isoxazole,
4-[1-(3,4-difluoro-phenyl)-1H-imidazol-4-yl]-5-methyl-3-phenyl-isoxazole,
4-[1-(3,5-difluoro-phenyl)-1H-imidazol-4-yl]-5-methyl-3-phenyl-isoxazole,
4-[1-(3-chloro-4-fluoro-phenyl)-1H-imidazol-4-yl]-5-methyl-3-phenyl-isoxazole,
4-[1-(3,4-dichloro-phenyl)-1H-imidazol-4-yl]-5-methyl-3-phenyl-isoxazole,
4-[1-(2,4-dichloro-phenyl)-1H-imidazol-4-yl]-5-methyl-3-phenyl-isoxazole,
4-[1-(2-fluoro-5-methoxy-phenyl)-1H-imidazol-4-yl]-5-methyl-3-phenyl-isoxazole,
4-[1-(4-fluoro-benzyl)-1H-imidazol-4-yl]-5-methyl-3-phenyl-isoxazole,
4-[1-(2-chloro-phenyl)-1H-imidazol-4-yl]-5-methyl-3-phenyl-isoxazole,
4-[1-(2-bromo-phenyl)-1H-imidazol-4-yl]-5-methyl-3-phenyl-isoxazole,
3-(4-fluoro-phenyl)-4-[1-(4-fluoro-phenyl)-1H-imidazol-4-yl]-5-methyl-isoxazole,
4-[1-(4-bromo-phenyl)-1H-imidazol-4-yl]-3-(4-fluoro-phenyl)-5-methyl-isoxazole,
3-(4-fluoro-phenyl)-4-[1-(3-fluoro-phenyl)-1H-imidazol-4-yl]-5-methyl-isoxazole,
4-[1-(3-chloro-phenyl)-1H-imidazol-4-yl]-3-(4-fluoro-phenyl)-5-methyl-isoxazole,
4-[1-(3-bromo-phenyl)-1H-imidazol-4-yl]-3-(4-fluoro-phenyl)-5-methyl-isoxazole,
4-[1-(3,4-difluoro-phenyl)-1H-imidazol-4-yl]-3-(4-fluoro-phenyl)-5-methyl-isoxazole,
4-[1-(3,5-difluoro-phenyl)-1H-imidazol-4-yl]-3-(4-fluoro-phenyl)-5-methyl-isoxazole and
4-[1-(3,5-dichloro-phenyl)-1H-imidazol-4-yl]-3-(4-fluoro-phenyl)-5-methyl-isoxazole.

In a certain embodiment, the compounds of the invention are those compounds of formula I wherein R⁵ is —(CH₂)ₘ-aryl or —(CH₂)ₘ-5 or 6 membered heteroaryl which is substituted by one or more cyano, for example the following compounds: examples 4-[4-(5-methyl-3-phenyl-isoxazol-4-yl)-imidazol-1-yl]-benzonitrile,
3-[4-(5-methyl-3-phenyl-isoxazol-4-yl)-imidazol-1-yl]-benzonitrile,
4-[2-benzyloxymethyl-4-(5-methyl-3-phenyl-isoxazol-4-yl)-imidazol-1-yl]-benzonitrile,
4-{4-[3-(4-fluoro-phenyl)-5-methyl-isoxazol-4-yl]-imidazol-1-yl}-benzonitrile,
3-{4-[3-(4-fluoro-phenyl)-5-methyl-isoxazol-4-yl]-imidazol-1-yl}-benzonitrile and
4-[4-(5-hydroxymethyl-3-phenyl-isoxazol-4-yl)-imidazol-1-yl]-benzonitrile.

In a certain embodiment, the compounds of the invention are those compounds of formula I wherein R⁵ is —(CH₂)ₘ-aryl or —(CH₂)ₘ-5 or 6 membered heteroaryl which is substituted by nitro, for example the following compounds:

5-methyl-4-[1-(4-nitro-phenyl)-1H-imidazol-4-yl]-3-phenyl-isoxazole,
3-(2-fluoro-phenyl)-5-methyl-4-[1-(4-nitro-phenyl)-1H-imidazol-4-yl]-isoxazole,
3-(3-fluoro-phenyl)-5-methyl-4-[1-(4-nitro-phenyl)-1H-imidazol-4-yl]-isoxazole, 3-(3-bromo-phenyl)-5-methyl-4-[1-(4-nitro-phenyl)-1H-imidazol-4-yl]-isoxazole,
3-(4-fluoro-phenyl)-5-methyl-4-[1-(4-nitro-phenyl)-1H-imidazol-4-yl]-isoxazole,
3-(4-bromo-phenyl)-5-methyl-4-[1-(4-nitro-phenyl)-1H-imidazol-4-yl]-isoxazole,
3-(3,4-difluoro-phenyl)-5-methyl-4-[1-(4-nitro-phenyl)-1H-imidazol-4-yl]-isoxazole,
5-methyl-4-[2-methyl-1-(4-nitro-phenyl)-1H-imidazol-4-yl]-3-phenyl-isoxazole,
4-[2-benzyloxymethyl-1-(4-nitro-phenyl)-1H-imidazol-4-yl]-5-methyl-3-phenyl-isoxazole,
5-methyl-4-[1-(3-nitro-phenyl)-1H-imidazol-4-yl]-3-phenyl-isoxazole,
3-(4-fluoro-phenyl)-5-methyl-4-[1-(4-methyl-3-nitro-phenyl)-1H-imidazol-4-yl]-isoxazole,
5-ethyl-3-(4-fluoro-phenyl)-4-[1-(4-nitro-phenyl)-1H-imidazol-4-yl]-isoxazole,
5-cyclopropyl-4-[1-(4-nitro-phenyl)-1H-imidazol-4-yl]-3-phenyl-isoxazole,
[4-(5-methyl-3-phenyl-isoxazol-4-yl)-1-(4-nitro-phenyl)-1H-imidazol-2-yl]-methanol,
4-[2-chloromethyl-1-(4-nitro-phenyl)-1H-imidazol-4-yl]-5-methyl-3-phenyl-isoxazole,
4-(5-methyl-3-phenyl-isoxazol-4-yl)-1-(4-nitro-phenyl)-1H-imidazole-2-carbaldehyde,
5-methyl-4-[2-(4-methyl-benzyloxymethyl)-1-(4-nitro-phenyl)-1H-imidazol-4-yl]-3-phenyl-isoxazole,
4-[2-(4-fluoro-benzyloxymethyl)-1-(4-nitro-phenyl)-1H-imidazol-4-yl]-5-methyl-3-phenyl-isoxazole,
4-[2-(4-chloro-benzyloxymethyl)-1-(4-nitro-phenyl)-1H-imidazol-4-yl]-5-methyl-3-phenyl-isoxazole,
4-[2-(4-bromo-benzyloxymethyl)-1-(4-nitro-phenyl)-1H-imidazol-4-yl]-5-methyl-3-phenyl-isoxazole,
4-[2-(3-chloro-benzyloxymethyl)-1-(4-nitro-phenyl)-1H-imidazol-4-yl]-5-methyl-3-phenyl-isoxazole,
4-[2-(3-fluoro-benzyloxymethyl)-1-(4-nitro-phenyl)-1H-imidazol-4-yl]-5-methyl-3-phenyl-isoxazole,
4-[2-(3-bromo-benzyloxymethyl)-1-(4-nitro-phenyl)-1H-imidazol-4-yl]-5-methyl-3-phenyl-isoxazole,
4-[2-(2-fluoro-benzyloxymethyl)-1-(4-nitro-phenyl)-1H-imidazol-4-yl]-5-methyl-3-phenyl-isoxazole,
2-[4-(5-methyl-3-phenyl-isoxazol-4-yl)-1-(4-nitro-phenyl)-1H-imidazol-2-ylmethoxymethyl]-pyridine,
2-methyl-6-[4-(5-methyl-3-phenyl-isoxazol-4-yl)-1-(4-nitro-phenyl)-1H-imidazol-2-ylmethoxymethyl]-pyridine,
3-[4-(5-methyl-3-phenyl-isoxazol-4-yl)-1-(4-nitro-phenyl)-1H-imidazol-2-ylmethoxymethyl]-pyridine,
5-[4-(5-methyl-3-phenyl-isoxazol-4-yl)-1-(4-nitro-phenyl)-1H-imidazol-2-ylmethoxymethyl]-2-trifluoromethyl-pyridine and
4-[4-(5-methyl-3-phenyl-isoxazol-4-yl)-1-(4-nitro-phenyl)-1H-imidazol-2-ylmethoxymethyl]-pyridine.

In a certain embodiment, the compounds of the invention are those compounds of formula I wherein $R^5$ is —$(CH_2)_m$-aryl or —$(CH_2)_m$-5 or 6 membered heteroaryl which is substituted by lower alkyl, for example the following compounds: examples
5-methyl-3-phenyl-4-(1-m-tolyl-1H-imidazol-4-yl)-isoxazole,
5-methyl-3-phenyl-4-[1-(4-propyl-phenyl)-1H-imidazol-4-yl]-isoxazole,
4-[2-benzyloxymethyl-1-(5-methyl-isoxazol-3-ylmethyl)-1H-imidazol-4-yl]-5-methyl-3-phenyl-isoxazole,
5-methyl-4-[1-(5-methyl-isoxazol-3-ylmethyl)-2-phenyl-1H-imidazol-4-yl]-3-phenyl-isoxazole,
3-(4-fluoro-phenyl)-5-methyl-4-(1-m-tolyl-1H-imidazol-4-yl)-isoxazole and
3-(4-fluoro-phenyl)-5-methyl-4-[1-(4-methyl-3-nitro-phenyl)-1H-imidazol-4-yl]-isoxazole.

In a certain embodiment, the compounds of the invention are those compounds of formula I wherein $R^5$ is —$(CH_2)_m$-aryl or —$(CH_2)_m$-5 or 6 membered heteroaryl which is substituted by lower alkoxy, for example the following compounds:
4-[1-(4-methoxy-phenyl)-1H-imidazol-4-yl]-5-methyl-3-phenyl-isoxazole,
4-[1-(4-ethoxy-phenyl)-1H-imidazol-4-yl]-5-methyl-3-phenyl-isoxazole,
4-[1-(2-ethoxy-phenyl)-1H-imidazol-4-yl]-5-methyl-3-phenyl-isoxazole,
4-[1-(2-fluoro-5-methoxy-phenyl)-1H-imidazol-4-yl]-5-methyl-3-phenyl-isoxazole,
3-(2-fluoro-phenyl)-4-[1-(4-methoxy-phenyl)-1H-imidazol-4-yl]-5-methyl-isoxazole,
3-(3-fluoro-phenyl)-4-[1-(4-methoxy-phenyl)-1H-imidazol-4-yl]-5-methyl-isoxazole and
4-[1-(3-ethoxy-phenyl)-1H-imidazol-4-yl]-5-methyl-3-phenyl-isoxazole.

In a certain embodiment, the compounds of the invention are those compounds of formula I wherein $R^5$ is —$(CH_2)_m$-aryl or —$(CH_2)_m$-5 or 6 membered heteroaryl which is substituted by lower alkylsulfanyl, for example the following compound:
5-methyl-4-[1-(4-methylsulfanyl-phenyl)-1H-imidazol-4-yl]-3-phenyl-isoxazole.

In a certain embodiment, the compounds of the invention are those compounds of formula I wherein $R^5$ is —$(CH_2)_m$-aryl or —$(CH_2)_m$-5 or 6 membered heteroaryl which is substituted by lower alkyl substituted by halogen, for example the following compounds:
5-methyl-3-phenyl-4-[1-(3-trifluoromethyl-phenyl)-1H-imidazol-4-yl]-isoxazole,
5-methyl-3-phenyl-4-[1-(4-trifluoromethyl-phenyl)-1H-imidazol-4-yl]-isoxazole,
5-methyl-3-phenyl-4-[1-(2-trifluoromethyl-phenyl)-1H-imidazol-4-yl]-isoxazole,
4-[1-(3,5-bis-trifluoromethyl-phenyl)-1H-imidazol-4-yl]-5-methyl-3-phenyl-isoxazole,
3-(3,4-difluoro-phenyl)-5-methyl-4-[1-(4-trifluoromethyl-phenyl)-1H-imidazol-4-yl]-isoxazole,
5-methyl-4-[2-methyl-1-(4-trifluoromethyl-phenyl)-1H-imidazol-4-yl]-3-phenyl-isoxazole,
4-[2-benzyloxymethyl-1-(4-trifluoromethyl-phenyl)-1H-imidazol-4-yl]-5-methyl-3-phenyl-isoxazole,
3-(4-fluoro-phenyl)-5-methyl-4-[1-(3-trifluoromethyl-phenyl)-1H-imidazol-4-yl]-isoxazole,
3-(4-fluoro-phenyl)-5-methyl-4-[1-(2-trifluoromethyl-phenyl)-1H-imidazol-4-yl]-isoxazole,
5-ethyl-3-(4-fluoro-phenyl)-4-[1-(4-trifluoromethyl-phenyl)-1H-imidazol-4-yl]-isoxazole,
{3-phenyl-4-[1-(4-trifluoromethyl-phenyl)-1H-imidazol-4-yl]-isoxazol-5-yl}-methanol,
{3-(4-fluoro-phenyl)-4-[1-(4-trifluoromethyl-phenyl)-1H-imidazol-4-yl]-isoxazol-5-yl}-methanol,
3-(4-fluoro-phenyl)-5-methoxymethyl-4-[1-(4-trifluoromethyl-phenyl)-1H-imidazol-4-yl]-isoxazole and
4-(5-methyl-3-phenyl-isoxazol-4-yl)-1-(4-trifluoromethyl-phenyl)-1H-imidazole-2-carboxylic acid ethyl ester.

In a certain embodiment, the compounds of the invention are those compounds of formula I wherein $R^5$ is —$(CH_2)_m$- aryl or —(CH₂)ₘ-5 or 6 membered heteroaryl which is substituted by —(CO)-lower alkyl, for example the following compounds:
1-{4-[4-(3-phenyl-isoxazol-4-yl)-imidazol-1-yl]-phenyl}-ethanone,
1-{4-[4-(5-methyl-3-phenyl-isoxazol-4-yl)-imidazol-1-yl]-phenyl}-ethanone,
1-{4-[4-(5-ethyl-3-phenyl-isoxazol-4-yl)-imidazol-1-yl]-phenyl}-ethanone,
5-ethyl-4-[1-(4-nitro-phenyl)-1H-imidazol-4-yl]-3-phenyl-isoxazole,
1-(4-{4-[3-(2-fluoro-phenyl)-5-methyl-isoxazol-4-yl]-imidazol-1-yl}-phenyl)-ethanone,
1-(4-{4-[3-(3-fluoro-phenyl)-5-methyl-isoxazol-4-yl]-imidazol-1-yl}-phenyl)-ethanone,
1-(4-{4-[3-(3-bromo-phenyl)-5-methyl-isoxazol-4-yl]-imidazol-1-yl}-phenyl)-ethanone,
1-(4-{4-[3-(4-fluoro-phenyl)-5-methyl-isoxazol-4-yl]-imidazol-1-yl}-phenyl)-ethanone,
1-(4-{4-[3-(4-bromo-phenyl)-5-methyl-isoxazol-4-yl]-imidazol-1-yl}-phenyl)-ethanone,
1-(4-{4-[3-(3,4-difluoro-phenyl)-5-methyl-isoxazol-4-yl]-imidazol-1-yl}-phenyl)-ethanone,
1-{4-[2-methyl-4-(5-methyl-3-phenyl-isoxazol-4-yl)-imidazol-1-yl]-phenyl}-ethanone,
1-{4-[2-benzyloxymethyl-4-(5-methyl-3-phenyl-isoxazol-4-yl)-imidazol-1-yl]-phenyl}-ethanone,
1-(4-{4-[5-ethyl-3-(4-fluoro-phenyl)-isoxazol-4-yl]-imidazol-1-yl}-phenyl)-ethanone,
1-{4-[4-(5-cyclopropyl-3-phenyl-isoxazol-4-yl)-imidazol-1-yl]-phenyl}-ethanone,
1-(4-{4-[3-(4-fluoro-phenyl)-5-hydroxymethyl-isoxazol-4-yl]-imidazol-1-yl}-phenyl)-ethanone and
1-(4-{4-[3-(4-fluoro-phenyl)-5-methoxymethyl-isoxazol-4-yl]-imidazol-1-yl}-phenyl)-ethanone.

In a certain embodiment, the compounds of the invention are those compounds of formula I wherein R⁵ is —(CH₂)ₘ-aryl or —(CH₂)ₘ-5 or 6 membered heteroaryl which is substituted by —(CO)—O-lower alkyl, for example the following compounds:
3-[4-(5-methyl-3-phenyl-isoxazol-4-yl)-imidazol-1-yl]-benzoic acid methyl ester,
4-{5-[3-(3-fluoro-phenyl)-5-methyl-isoxazol-4-yl]-imidazol-1-yl}-benzoic acid ethyl ester and
4-{4-[3-(4-fluoro-phenyl)-5-methyl-isoxazol-4-yl]-imidazol-1-yl}-benzoic acid methyl ester.

In a certain embodiment, the compounds of the invention are those compounds of formula I wherein R⁵ is —(CH₂)ₘ-aryl or —(CH₂)ₘ-5 or 6 membered heteroaryl which is substituted by —NH—(CO)—O-lower alkyl, for example the following compound:
{4-[4-(5-methyl-3-phenyl-isoxazol-4-yl)-imidazol-1-yl]-phenyl}-carbamic acid tert-butyl ester.

In a certain embodiment, the compounds of the invention are those compounds of formula I wherein R⁵ is —(CH₂)ₘ-aryl or —(CH₂)ₘ-5 or 6 membered heteroaryl which is substituted by —C(O)—NH—R', wherein R' is lower alkynyl or lower alkyl substituted by halogen or hydroxy, or is —(CH₂)ₙ- cycloalkyl, —(CH₂)ₙ-heterocyclyl, —(CH₂)ₙ-heteroaryl or —(CH₂)ₙ-aryl, each of which is optionally substituted by halogen, for example the following compounds:
N-cyclopropylmethyl-4-[4-(5-methyl-3-phenyl-isoxazol-4-yl)-imidazol-1-yl]-benzamide,
4-[4-(5-methyl-3-phenyl-isoxazol-4-yl)-imidazol-1-yl]-N-prop-2-ynyl-benzamide,
4-[4-(5-methyl-3-phenyl-isoxazol-4-yl)-imidazol-1-yl]-N-(3-morpholin-4-yl-propyl)-benzamide,
N-cyclopropyl-4-[4-(5-methyl-3-phenyl-isoxazol-4-yl)-imidazol-1-yl]-benzamide,
N-cyclobutyl-4-[4-(5-methyl-3-phenyl-isoxazol-4-yl)-imidazol-1-yl]-benzamide,
N-cyclopentyl-4-[4-(5-methyl-3-phenyl-isoxazol-4-yl)-imidazol-1-yl]-benzamide,
4-[4-(5-methyl-3-phenyl-isoxazol-4-yl)-imidazol-1-yl]-N-(tetrahydro-pyran-4-yl)-benzamide,
4-[4-(5-methyl-3-phenyl-isoxazol-4-yl)-imidazol-1-yl]-N-pyridin-3-ylmethyl-benzamide,
4-[4-(5-methyl-3-phenyl-isoxazol-4-yl)-imidazol-1-yl]-N-pyridin-4-ylmethyl-benzamide,
N-(3-fluoro-phenyl)-4-[4-(5-methyl-3-phenyl-isoxazol-4-yl)-imidazol-1-yl]-benzamide,
N-cyclopropylniethyl-3-[4-(5-methyl-3-phenyl-isoxazol-4-yl)-imidazol-1-yl]-benzamide,
N-cyclopropyl-3-[4-(5-methyl-3-phenyl-isoxazol-4-yl)-imidazol-1-yl]-benzamide,
N-cyclobutyl-3-[4-(5-methyl-3-phenyl-isoxazol-4-yl)-imidazol-1-yl]-benzamide,
N-cyclopentyl-3-[4-(5-methyl-3-phenyl-isoxazol-4-yl)-imidazol-1-yl]-benzamide,
3-[4-(5-methyl-3-phenyl-isoxazol-4-yl)-imidazol-1-yl]-N-(tetrahydro-pyran-4-yl)-benzamide,
N-cyclopropylmethyl-2-[4-(5-methyl-3-phenyl-isoxazol-4-yl)-imidazol-1-yl]-benzamide,
2-[4-(5-methyl-3-phenyl-isoxazol-4-yl)-imidazol-1-yl]-N-prop-2-ynyl-benzamide,
N-cyclobutyl-2-[4-(5-methyl-3-phenyl-isoxazol-4-yl)-imidazol-1-yl]-benzamide,
N-cyclopentyl-2-[4-(5-methyl-3-phenyl-isoxazol-4-yl)-imidazol-1-yl]-benzamide,
2-[4-(5-methyl-3-phenyl-isoxazol-4-yl)-imidazol-1-yl]-N-(tetrahydro-pyran-4-yl)-benzamide,
N-cyclopropylmethyl-4-{4-[3-(3-fluoro-phenyl)-5-methyl-isoxazol-4-yl]-imidazol-1-yl}-benzamide,
4-{4-[3-(3-fluoro-phenyl)-5-methyl-isoxazol-4-yl]-imidazol-1-yl}-N-prop-2-ynyl-benzamide,
N-cyclopropyl-4-{4-[3-(3-fluoro-phenyl)-5-methyl-isoxazol-4-yl]-imidazol-1-yl}-benzamide,
N-cyclobutyl-4-{4-[3-(3-fluoro-phenyl)-5-methyl-isoxazol-4-yl]-imidazol-1-yl}-benzamide,
N-cyclopentyl-4-{4-[3-(3-fluoro-phenyl)-5-methyl-isoxazol-4-yl]-imidazol-1-yl}-benzamide,
4-{4-[3-(3-fluoro-phenyl)-5-methyl-isoxazol-4-yl]-imidazol-1-yl}-N-(2-hydroxy-ethyl)-benzamide,
4-{4-[3-(3-fluoro-phenyl)-5-methyl-isoxazol-4-yl]-imidazol-1-yl}-N-(2-morpholin-4-yl-ethyl)-benzamide,
4-{4-[3-(3-fluoro-phenyl)-5-methyl-isoxazol-4-yl]-imidazol-1-yl}-N-(3-morpholin-4-yl-propyl)-benzamide,
4-{4-[3-(3-fluoro-phenyl)-5-methyl-isoxazol-4-yl]-imidazol-1-yl}-N-[2-(1H-imidazol-4-yl)-ethyl]-benzamide,
4-{4-[3-(3-fluoro-phenyl)-5-methyl-isoxazol-4-yl]-imidazol-1-yl}-N-furan-2-ylmethyl-benzamide,
4-{4-[3-(3-fluoro-phenyl)-5-methyl-isoxazol-4-yl]-imidazol-1-yl}-N-pyridin-2-ylmethyl-benzamide,
N-(3-fluoro-phenyl)-4-{4-[3-(3-fluoro-phenyl)-5-methyl-isoxazol-4-yl]-imidazol-1-yl}-benzamide,
N-cyclopropylmethyl-3-{4-[3-(3-fluoro-phenyl)-5-methyl-isoxazol-4-yl]-imidazol-1-yl}-benzamide,
N-cyclopropyl-3-{4-[3-(3-fluoro-phenyl)-5-methyl-isoxazol-4-yl]-imidazol-1-yl}-benzamide,
N-cyclobutyl-3-{4-[3-(3-fluoro-phenyl)-5-methyl-isoxazol-4-yl]-imidazol-1-yl}-benzamide,
N-cyclopentyl-3-{4-[3-(3-fluoro-phenyl)-5-methyl-isoxazol-4-yl]-imidazol-1-yl}-benzamide, 3-{4-[3-(3-fluoro-phenyl)-5-methyl-isoxazol-4-yl]-imidazol-1-yl}-N-(tetrahydro-pyran-4-yl)-benzamide;

4-{4-[3-(3-fluoro-phenyl)-5-methyl-isoxazol-4-yl]-imidazol-1-yl}-N-pyridin-3-ylmethyl-benzamide and N-cyclopentyl-4-{4-[3-(4-fluoro-phenyl)-5-methyl-isoxazol-4-yl]-imidazol-1-yl}-benzamide.

The present compounds of formula I and their pharmaceutically acceptable salts can be prepared by a process comprising the steps of:

a) reacting a compound of formula II:

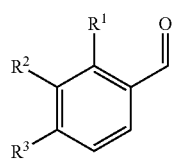

II with hydroxylamine hydrochloride in a suitable solvent, such as ethanol and water, in the presence of a base, such as aqueous sodium hydroxide, to give a compound of formula III:

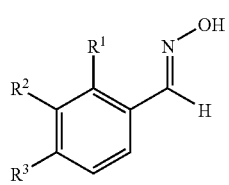

III b) reacting the compound of formula III with a chlorinating agent, such as N-chlorosuccinimide, in a suitable solvent, such as DMF, to give a compound of formula IV:

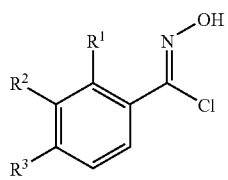

IV c1) either reacting the compound of formula IV with a compound of formula V:

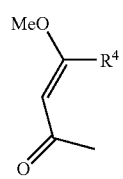

V in the presence of a suitable base, such as triethylamine, in a suitable solvent, such as DCM, c2) or reacting the compound of formula IV with a compound of formula VI:

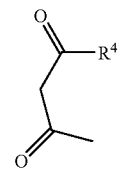

VI in the presence of a suitable base, such as sodium hydride or sodium methoxide, in a suitable solvent, such as DCM or methanol, to give a compound of formula VII:

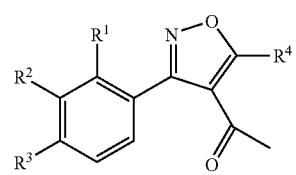

VII d) reacting the compound of formula VII with bromine in a suitable solvent, such as chloroform and acetic acid, to give a compound of formula VIII:

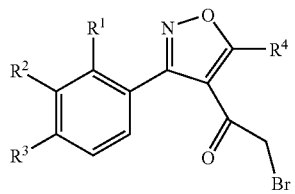

VIII e1) either treating the compound of formula VIII with formamide in the presence of water under heating, e.g. conventional heating or microwave heating to give a compound of formula IX:

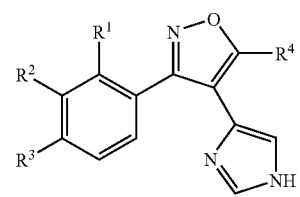

IX e2) or treating the compound of formula VIII with a compound of formula X:

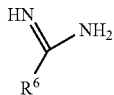

in the presence of suitable solvent, such as dichloromethane, to give a compound of formula XI:

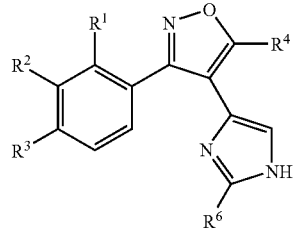

f1) either treating the compound of formula XI with an electrophile of formula X—$R^5$, wherein X is a halogen atom, f2) or treating the compound of formula XI with an electrophile of formula $B(OH)_2$—$R^5$ to give a compound of formula I:

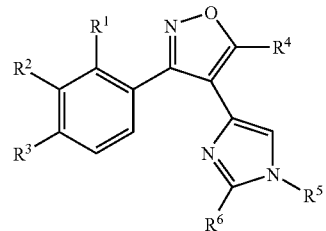

wherein $R^1$ to $R^6$ are as described for formula I hereinabove, and, if desired, converting a compound of formula I into a pharmaceutically acceptable salt.

The following schemes describe the processes for preparation of compounds of formula I in more detail.

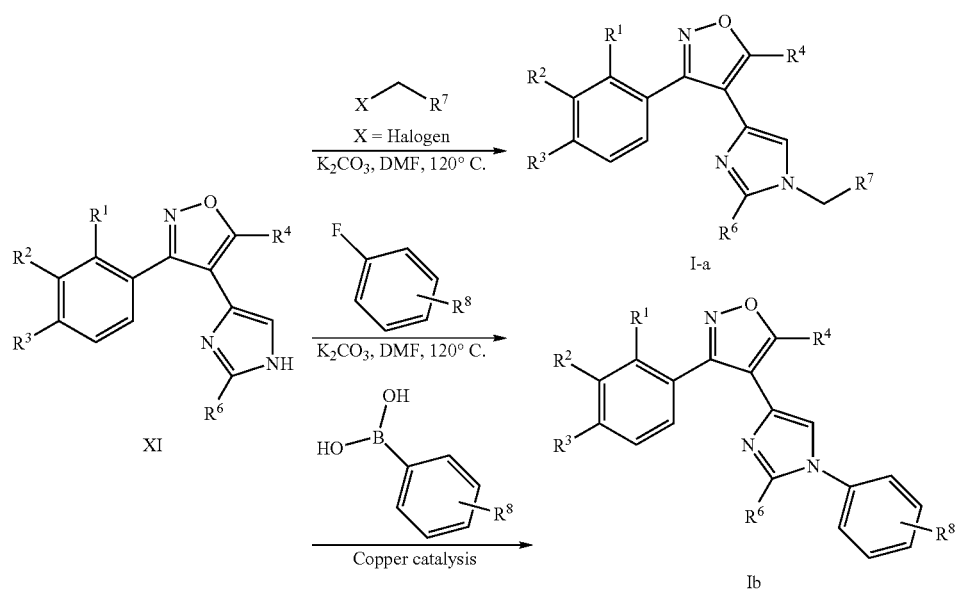

Scheme 1 wherein R⁷ is —(CH₂)_{m-1}-aryl or —(CH₂)_{m-1}-heteroaryl which are optionally substituted by one or more substituents selected from the group consisting of halogen, cyano, nitro, lower alkyl, lower alkoxy, lower alkylsulfanyl, lower alkyl substituted by halogen,
—C(O)-lower alkyl, —C(O)—O-lower alkyl, —NH—C(O)—O-lower alkyl or
—C(O)—NH—R', wherein R' is as defined above, and
R⁸ is halogen, cyano, nitro, lower alkyl, lower alkoxy, lower alkylsulfanyl, lower alkyl substituted by halogen, —C(O)-lower alkyl, —C(O)—O-lower alkyl, —NH—C(O)—O-lower alkyl or —C(O)—NH—R' and wherein R' is as defined above.

In accordance with Scheme 1, compounds of formula I-a and I-b can be prepared following standards methods.

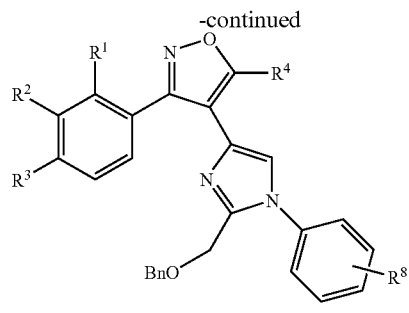

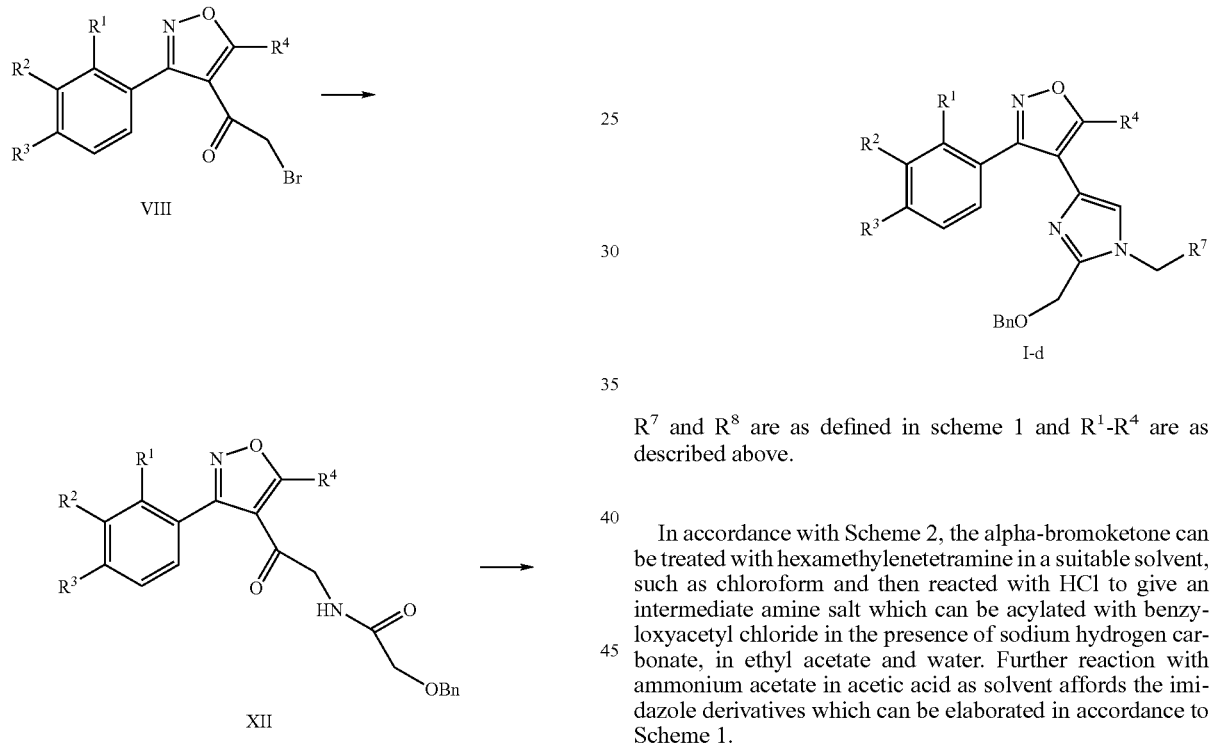

R⁷ and R⁸ are as defined in scheme 1 and R¹-R⁴ are as described above.

In accordance with Scheme 2, the alpha-bromoketone can be treated with hexamethylenetetramine in a suitable solvent, such as chloroform and then reacted with HCl to give an intermediate amine salt which can be acylated with benzyloxyacetyl chloride in the presence of sodium hydrogen carbonate, in ethyl acetate and water. Further reaction with ammonium acetate in acetic acid as solvent affords the imidazole derivatives which can be elaborated in accordance to Scheme 1.

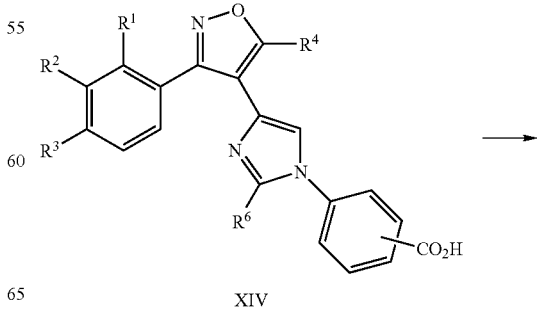

-continued

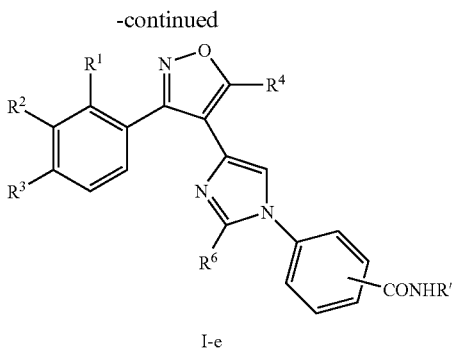

I-e

The definitions are as described above.

In accordance with Scheme 3, the acids of formula XIV which can be activated following standard procedures by 1-ethyl-3-(3'-dimethylaminopropyl)carbodiimide, 1-hydroxybenzotriazole, triethylamine and then reacted with an amine ($R'NH_2$) of choice to give compounds of formula I-e.

The definition of substituents are as described above.

-continued

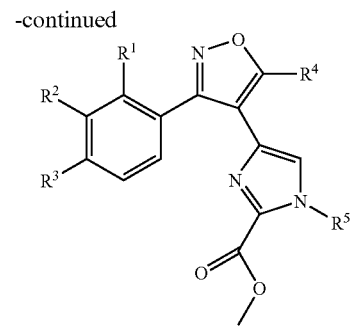

I-f

In accordance with Scheme 4, compounds of formula VIII can be oxidised with DMSO, water to produce the compounds of formula XVI which can then be reacted with a mixture of ammonium acetate in water and acetonitrile at 0° C. together with 2-hydroxy-2-methoxyacetic acid methyl ester to give products of formula XVI. These can be transformed into products of formula I-f following the procedures described in Scheme 1.

Scheme 4

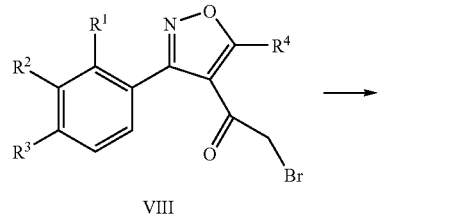

VIII

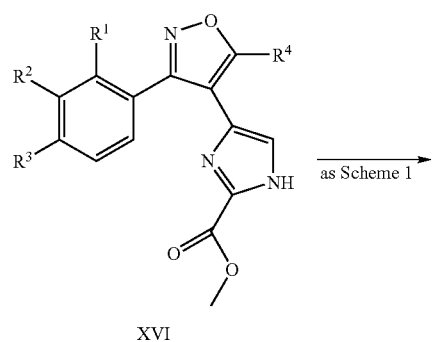

XV

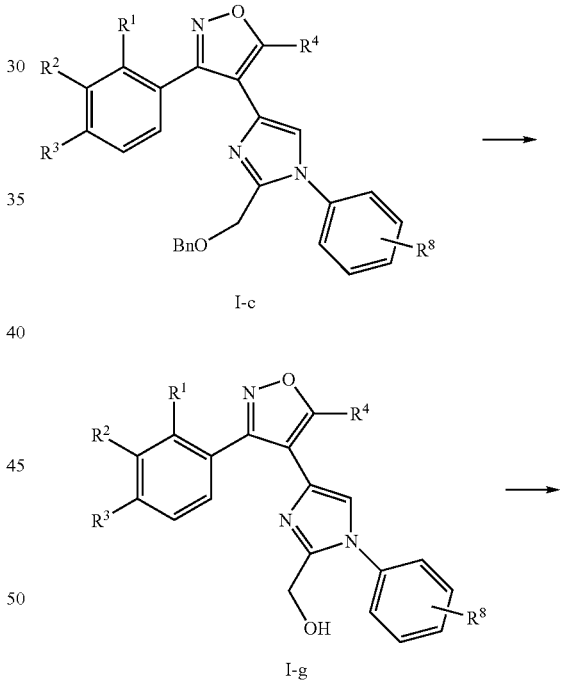

Scheme 5 as Scheme 1

XVI

-continued

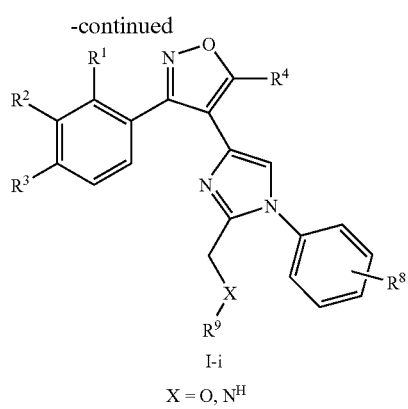

I-i

X = O, N^H $R^1$-$R^4$ are as described above, $R^8$ is as described in scheme 1 and $R^9$ is lower alkyl, —CH$_2$-aryl, optionally substituted by halogen or lower alkyl, or is —CH$_2$-heteroaryl, optionally substituted by halogen, lower alkyl or lower alkyl substituted by halogen, or is —(CH$_2$)$_o$-heterocyclyl.

In accordance with Scheme 5, compounds of formula I-c can be transformed into compounds of formula I-g by treatment with TFA and TfOH. The alcohols of formula I-g can then be converted into the chlorides of formula I-h in DCM at 0° C. in the presence of triethylamine and methanesulfonyl chloride. These can then be reacted with a range of alcohols or amines in the presence of NaH in DMF to give the products of formula I-i.

As mentioned earlier, the compounds of formula I and their pharmaceutically usable salts possess valuable pharmacological properties. It has been found that the compounds of the present invention are ligands for GABA A receptors containing the α5 subunit and are therefore useful in the therapy where cognition enhancement is required.

The compounds were investigated in accordance with the test given hereinafter:

Membrane Preparation and Binding Assay

The affinity of compounds at GABA A receptor subtypes was measured by competition for [3H]flumazenil (85 Ci/mmol; Roche) binding to HEK293 cells expressing rat (stably transfected) or human (transiently transfected) receptors of composition α1β3γ2, α2β3γ2, α3β3γ2 and α5β3γ2.

Cell pellets were suspended in Krebs-tris buffer (4.8 mM KCl, 1.2 mM CaCl2, 1.2 mM MgCl$_2$, 120 mM NaCl, 15 mM Tris; pH 7.5; binding assay buffer), homogenized by polytron for ca. 20 sec on ice and centrifuged for 60 min at 4° C. (50000 g; Sorvall, rotor: SM24=20000 rpm). The cell pellets were resuspended in Krebs-tris buffer and homogenized by polytron for ca. 15 sec on ice. Protein was measured (Bradford method, Bio-Rad) and aliquots of 1 mL were prepared and stored at −80° C.

Radioligand binding assays were carried out in a volume of 200 mL (96-well plates) which contained 100 mL of cell membranes, [3H]flumazenil at a concentration of 1 nM for α1, α2, α3 subunits and 0.5 nM for α5 subunits and the test compound in the range of 10-10$^{-3}$×10$^{-6}$ M. Nonspecific binding was defined by 10$^{-5}$ M diazepam and typically represented less than 5% of the total binding. Assays were incubated to equilibrium for 1 hour at 4° C. and harvested onto GF/C uni-filters (Packard) by filtration using a Packard harvester and washing with ice-cold wash buffer (50 mM Tris; pH 7.5). After drying, filter-retained radioactivity was detected by liquid scintillation counting. Ki values were calculated using Excel-Fit (Microsoft) and are the means of two determinations.

The compounds of the accompanying examples were tested in the above described assay, and the preferred compounds were found to possess a Ki value for displacement of [3H]flumazenil from α5 subunits of the rat GABA A receptor of 100 nM or less. Most preferred are compounds with a Ki (nM)<35. In a preferred embodiment the compounds of the invention are binding selective for the α5 subunit relative to the α1, α2 and α3 subunit.

| Example No. | Ki[nM] hα5 |
|---|---|
| 2 | 21.7 |
| 3 | 29.6 |
| 4 | 33.1 |
| 5 | 29.1 |
| 7 | 30.9 |
| 9 | 25.5 |
| 10 | 20.4 |
| 11 | 15.1 |
| 12 | 5.5 |
| 13 | 11.9 |
| 14 | 30.7 |
| 16 | 15.1 |
| 17 | 27.0 |
| 18 | 21.0 |
| 19 | 28.7 |
| 20 | 32.4 |
| 21 | 31.5 |
| 24 | 29.0 |
| 30 | 9.9 |
| 31 | 5.0 |
| 32 | 19.3 |
| 33 | 15 |
| 36 | 7.8 |
| 38 | 24.0 |
| 39 | 18.3 |
| 46 | 4.7 |
| 47 | 16.6 |
| 48 | 17.6 |
| 49 | 9.1 |
| 50 | 21.6 |
| 51 | 28.5 |
| 62 | 5.4 |
| 63 | 14.4 |
| 64 | 14.7 |
| 65 | 19.1 |
| 66 | 6.7 |
| 71 | 16.7 |
| 72 | 13.2 |
| 73 | 14.6 |
| 74 | 5.1 |
| 75 | 2.7 |
| 76 | 10.9 |
| 77 | 27.3 |
| 78 | 12.8 |
| 79 | 14.0 |
| 82 | 19.5 |
| 84 | 31.8 |
| 97 | 10.0 |
| 98 | 17.7 |
| 101 | 27.0 |
| 104 | 31.5 |
| 106 | 32.1 |
| 114 | 31.0 |
| 116 | 13.2 |
| 117 | 13.3 |
| 118 | 29.0 |
| 119 | 33.7 |
| 122 | 25.6 |
| 124 | 27.2 |
| 125 | 13.6 |
| 126 | 11.9 |
| 131 | 21.5 |
| 132 | 4.7 |

-continued

| Example No. | Ki[nM] hα5 |
|---|---|
| 133 | 29.8 |
| 134 | 12.7 |
| 135 | 1.64 |
| 136 | 1.71 |
| 139 | 28.2 |
| 140 | 9.8 |
| 146 | 17.1 |
| 147 | 18.1 |
| 148 | 23.3 |
| 149 | 29.9 |
| 153 | 17.3 |
| 154 | 13.5 |
| 158 | 17.0 |
| 160 | 12.7 |
| 161 | 16.3 |
| 162 | 28.2 |
| 163 | 9.5 |
| 164 | 27.0 |
| 165 | 18.2 |

The invention also provides pharmaceutical compositions containing compounds of the invention, for example compounds of formula I and their pharmaceutically acceptable acid addition salts, and a pharmaceutically acceptable carrier. Such pharmaceutical compositions can be in the form of tablets, coated tablets, dragées, hard and soft gelatine capsules, solutions, emulsions or suspensions. The pharmaceutical compositions also can be in the form of suppositories or injectable solutions.

The pharmaceutical compounds of the invention, in addition to one or more compounds of the invention, contain a pharmaceutically acceptable carrier. Suitable pharmaceutically acceptable carriers include pharmaceutically inert, inorganic and organic carriers. Lactose, corn starch or derivatives thereof, talc, stearic acid or its salts etc can be used as such excipients e.g. for tablets, dragées and hard gelatine capsules. Suitable excipients for soft gelatine capsules are e.g. vegetable oils, waxes, fats, semisolid and liquid polyols etc. Suitable excipients for the manufacture of solutions and syrups are e.g. water, polyols, saccharose, invert sugar, glucose etc. Suitable excipients for injection solutions are e.g. water, alcohols, polyols, glycerol, vegetable oils etc. Suitable excipients for suppositories are e.g. natural or hardened oils, waxes, fats, semi-liquid or liquid polyols etc.

Moreover, the pharmaceutical compositions can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Compounds of the invention have high affinity and selectivity for GABA A α5 receptor binding sites. The invention provides a method for enhancing cognition, which comprises administering to an individual a therapeutically effective amount of a compound of formula I or a pharmaceutically acceptable salt thereof. The invention further provides a method for treating Alzheimer's disease which comprises administering to an individual a therapeutically effective amount of a compound of formula I or a pharmaceutically acceptable salt thereof.

The compounds and compositions of the invention can be administered in a conventional manner, for example, orally, rectally, or parenterally. The compounds of the invention can be administered orally, for example, in the form of tablets, coated tablets, dragées, hard and soft gelatin capsules, solutions, emulsions, or suspensions. The compounds of the invention also can be administered rectally, for example, in the form of suppositories, or parenterally, for example, in the form of injectable solutions.

The dosage at which compounds can be administered can vary within wide limits and will, of course, be fitted to the individual requirements in each particular case. In general, in the case of oral administration a daily dosage of about 10 to 1000 mg per person of a compound of general formula I should be appropriate, although the above upper limit can also be exceeded when necessary.

The following examples illustrate the present invention without limiting it. All temperatures are given in degrees Celsius.

EXAMPLE A

Tablets of the following composition are manufactured in the usual manner:

|  | mg/tablet |
|---|---|
| Active substance | 5 |
| Lactose | 45 |
| Corn starch | 15 |
| Microcrystalline cellulose | 34 |
| Magnesium stearate | 1 |
| Tablet weight | 100 |

EXAMPLE B

Capsules of the following composition are manufactured:

|  | mg/capsule |
|---|---|
| Active substance | 10 |
| Lactose | 155 |
| Corn starch | 30 |
| Talc | 5 |
| Capsule fill weight | 200 |

The active substance, lactose and corn starch are firstly mixed in a mixer and then in a comminuting machine. The mixture is returned to the mixer, the talc is added thereto and mixed thoroughly. The mixture is filled by machine into hard gelatin capsules.

EXAMPLE C

Suppositories of the following composition are manufactured:

|  | mg/supp. |
|---|---|
| Active substance | 15 |
| Suppository mass | 1285 |
| Total | 1300 |

The suppository mass is melted in a glass or steel vessel, mixed thoroughly and cooled to 45° C.

Thereupon, the finely powdered active substance is added thereto and stirred until it has dispersed completely. The mixture is poured into suppository moulds of suitable size, left to cool, the suppositories are then removed from the moulds and packed individually in wax paper or metal foil.

The following examples 1-69 are provided for illustration of the invention. They should not be considered as limiting the scope of the invention, but merely as being representative thereof.

EXAMPLE 1

1-{4-[4-(3-Phenyl-isoxazol-4-yl)-imidazol-1-yl]-phenyl}-ethanone a) (E)- and/or (Z)-Benzaldehyde-oxime To a suspension of benzaldehyde (5.30 g, 55 mmol) and hydroxylamine hydrochloride (3.82 g, 55 mmol) in ethanol (4 mL) and water (12 mL) was added ice (23 g). Then a solution of sodium hydroxide (5.0 g, 125 mmol) in water (6 mL) was added dropwise within a 10 min period (temperature rises from −8° C. to +7° C.) whereupon most of the solid dissolves. After 30 min stirring at room temperature a white solid precipitated and the resulting mixture was then diluted with water and acidified with HCl (4 N). The white precipitate was then filtered off, washed with water and dried under high vacuum to afford the title compound (5.31 g, 88%) which was obtained as a colourless liquid. MS m/e (EI): 121.0 [M].

b) (E)- and/or (Z)-N-Hydroxy-benzenecarboximidoyl chloride

To a solution of (E)- and/or (Z)-benzaldehyde-oxime (5.27 g, 44 mmol) in DMF (44 mL) was added N-chlorosuccinimide (5.81 g, 44 mmol) portionwise over 1 h, keeping the temperature below 35° C. The reaction mixture was stirred at room temperature overnight. The mixture was then poured onto ice-water, and extracted with ethyl acetate. The combined organic layers were then washed with water and brine, dried over sodium sulphate and evaporated to afford the title compound (5.91 g, 87%) which was obtained as a light yellow solid. MS m/e (EI): 155.0 [M].

c) 1-(3-Phenyl-isoxazol-4-yl)-ethanone

To a mixture of (E)- and/or (Z)-N-hydroxy-benzenecarboximidoyl chloride (7.41 g, 48 mmol) and 4-methoxy-3-buten-2-one (4.77 mL, 48 mmol) in dichloromethane (48 mL) was added triethylamine (6.64 mL, 48 mmol) dropwise under ice-bath cooling keeping the temperature below 5° C. The reaction mixture was then stirred at 5° C. for 15 min, and then the ice-bath was removed and stirring was continued for 30 min (resulting in an increase in temperature to 32° C. Then the mixture was re-cooled under ice-bath cooling for another 30 min and then the ice-bath was removed again and allowed to warm up to room temperature and left overnight. The resulting mixture was then poured into HCl (1 N) and ice-water and then extracted with ethyl acetate. The organic extract was then dried over sodium sulphate and evaporated to leave a yellow oil. Purification by chromatography (SiO$_2$, heptane:ethyl acetate=100:0 to 50:50) afforded the title compound (6.35 g, 71%) which was obtained as a light yellow solid. MS m/e (EI)=187.1 [M].

d) 2-Bromo-1-(3-phenyl-isoxazol-4-yl)-ethanone

To a solution of 1-(3-phenyl-isoxazol-4-yl)-ethanone (6.35 g, 34 mmol) in chloroform (50 mL) and AcOH (1 mL) at 48° C. was added a solution of bromine (1.83 mL, 36 mmol) in chloroform (15 mL) over 10 min keeping the temperature below 50° C. After addition the reaction mixture was allowed to cool down to room temperature and poured into ice-water (200 mL). The layers were separated and the aqueous layer extracted with dichloromethane. The combined organic layers were then washed with water and brine, dried over sodium sulphate and evaporated. Purification by chromatography (SiO$_2$, heptane:ethyl acetate: 100:0 to 7:3) afforded the title compound (3.72 g, 41%) which was obtained as a light yellow solid. MS m/e (EI): 265.0/267.0 [M].

e) 4-(1H-Imidazol-4-yl)-3-phenyl-isoxazole

A suspension of 1-(3-phenyl-isoxazol-4-yl)-ethanone (1.91 g, 7 mmol) in formamide (6.9 mL, 172 mmol) and water (0.78 mL, 43 mmol) was heated in the microwave at 140° C. for 1 h. The resulting mixture was then poured into HCl (1 N, 200 mL) and extracted with ethyl acetate. The aqueous layer was then made basic with sodium hydroxide (4 N) and then extracted with ethyl acetate. The combined organic extracts were then dried over sodium sulphate and evaporated to leave a yellow solid. Purification by chromatography (SiO$_2$, heptane:ethyl acetate=90:10 to 0:100) afforded the title compound (528 mg, 35%) which was obtained as a light yellow solid. MS: m/e=212.1 [M+H]$^+$.

f) 1-{4-[4-(3-Phenyl-isoxazol-4-yl)-imidazol-1-yl]-phenyl}-ethanone

To a solution of 4-(1H-imidazol-4-yl)-3-phenyl-isoxazole (106 mg, 0.5 mmol) in DMF (2.5 mL) was added 4-fluoroacetophenone (61 mL, 0.5 mmol) and potassium carbonate (138 mg, 1.0 mmol) and the resulting mixture heated at 120° C. overnight. The resulting mixture was then poured into HCl (1 N, 200 mL) and extracted with ethyl acetate which was then washed with brine, dried over sodium sulphate and evaporated. Purification by chromatography (SiO$_2$, heptane:ethyl acetate=100:0 to 0:100) afforded the title compound (36 mg, 22%) which was obtained as a light yellow solid. MS: m/e=330.1 [M+H]$^+$.

EXAMPLE 2

5-Methyl-3-phenyl-4-(1-phenyl-1H-imidazol-4-yl)-isoxazole a) 4-(1H-Imidazol-4-yl)-5-methyl-3-phenyl-isoxazole A solution of 4-(bromoacetyl)-5-methyl-3-phenylisoxazole (commercially available) (6.8 g, 24 mmol) in formamide (23.2 mL, 583 mmol) and water (2.3 mL) was heated in the microwave at 140° C. for 1.5 h. The resulting mixture was then poured into HCl (1 N, 200 mL) and extracted with ethyl acetate. The aqueous layer was then made basic with sodium hydroxide (4 N) and then extracted with ethyl acetate. The combined organic extracts were then dried over sodium sulphate and evaporated to leave a brown solid which was recrystallised from hexane-ethyl acetate to afford the title compound (2.72 g, 50%) which was obtained as an off-white solid. MS: m/e=226.3 [M+H]$^+$.

b) 5-Methyl-3-phenyl-4-(1-phenyl-1H-imidazol-4-yl)-isoxazole

To a mixture of copper(I) trifluoromethanesulfonate benzene complex (12.3 mg, 0.22 mmol), 1,10-phenanthroline (79.5 mg, 0.44 mmol), dibenzylideneacetone (5.2 mg, 0.22 mmol) and cesium carbonate (144 mg, 0.44 mmol) was added a suspension of 4-(1H-imidazol-4-yl)-5-methyl-3-phenyl-isoxazole (149 mg, 0.6 mmol) in toluene (2 mL) followed by iodobenzene (90 mg, 0.44 mmol) and the resulting mixture heated at 120° C. for 2 days. After cooling to room temperature the resulting mixture was poured into aqueous ammonium chloride (saturated) and extracted with ethyl acetate. The organic extracts were then dried over sodium sulphate and evaporated. Purification by chromatography (SiO$_2$, heptane:ethyl acetate=1:1) afforded the title compound (18 mg, 13%) which was obtained as a light brown gum. MS: m/e=302.1 [M+H]$^+$.

EXAMPLE 3

4-[1-(4-Fluoro-phenyl)-1H-imidazol-4-yl]-5-methyl-3-phenyl-isoxazole

To a mixture of 4-(1H-imidazol-4-yl)-5-methyl-3-phenyl-isoxazole (112.6 mg, 0.5 mmol) containing [Cu(OH).TMEDA]$_2$Cl$_2$ (23.2 mg, 0.05 mmol) in dry methanol (5 mL) was added 4-fluorophenylboronic acid (140 mg, 1.0 mmol) under an air atmosphere and the resulting mixture stirred at room temperature overnight. After this time, concentrated ammonia solution (2 mL) was added and then the resulting mixture was diluted with water (20 mL) and extracted with ethyl acetate. The organic extracts were then dried over sodium sulphate and evaporated. Purification by preparative HPLC on reversed phase eluting with an acetonitrile/water [0.1% aq NH$_3$ (25%)] gradient afforded the title compound (34 mg, 21%) which was obtained as a white solid. MS (ESI): m/e=320.0 [M+H]$^+$.

EXAMPLE 4

4-[1-(3-Fluoro-phenyl)-1H-imidazol-4-yl]-5-methyl-3-phenyl-isoxazole

As described for Example 3, 4-(1H-imidazol-4-yl)-5-methyl-3-phenyl-isoxazole (112.6 mg, 0.5 mmol) was converted, using 3-fluorophenylboronic acid instead of 4-fluorophenylboronic acid, to the title compound (40 mg, 25%) which was obtained as a white solid. MS (ESI): m/e=320.0 [M+H]$^+$.

EXAMPLE 5

4-[1-(3-Chloro-phenyl)-1H-imidazol-4-yl]-5-methyl-3-phenyl-isoxazole

As described for Example 3, 4-(1H-imidazol-4-yl)-5-methyl-3-phenyl-isoxazole (112.6 mg, 0.5 mmol) was converted, using 3-chlorophenylboronic acid instead of 4-fluorophenylboronic acid, to the title compound (49 mg, 29%) which was obtained as a white solid. MS (ESI): m/e=335.9 [M+H]$^+$.

EXAMPLE 6

4-[1-(4-Bromo-phenyl)-1H-imidazol-4-yl]-5-methyl-3-phenyl-isoxazole

As described for Example 3, 4-(1H-imidazol-4-yl)-5-methyl-3-phenyl-isoxazole (112.6 mg, 0.5 mmol) was converted, using 2-bromophenylboronic acid instead of 4-fluorophenylboronic acid, to the title compound (78 mg, 41%) which was obtained as a white solid. MS (ESI): m/e=379.9 [M+H]$^+$.

EXAMPLE 7

4-[1-(3-Bromo-phenyl)-1H-imidazol-4-yl]-5-methyl-3-phenyl-isoxazole

As described for Example 3, 4-(1H-imidazol-4-yl)-5-methyl-3-phenyl-isoxazole (112.6 mg, 0.5 mmol) was converted, using 3-bromophenylboronic acid instead of 4-fluorophenylboronic acid, to the title compound (66 mg, 35%) which was obtained as a white solid. MS (ESI): m/e=379.9 [M+H]$^+$.

EXAMPLE 8

5-Methyl-3-phenyl-4-(1-m-tolyl-1H-imidazol-4-yl)-isoxazole

As described for Example 3, 4-(1H-imidazol-4-yl)-5-methyl-3-phenyl-isoxazole (112.6 mg, 0.5 mmol) was converted, using 3-methylphenylboronic acid instead of 4-fluorophenylboronic acid, to the title compound (16 mg, 10%) which was obtained as a white solid. MS (ESI): m/e=315.0 [M+H]$^+$.

EXAMPLE 9

5-Methyl-3-phenyl-4-[1-(4-propyl-phenyl)-1H-imidazol-4-yl]-isoxazole

As described for Example 3, 4-(1H-imidazol-4-yl)-5-methyl-3-phenyl-isoxazole (112.6 mg, 0.5 mmol) was converted, using 4-propylphenylboronic acid instead of 4-fluorophenylboronic acid, to the title compound (52 mg, 30%) which was obtained as a white solid. MS (ESI): m/e=344.0 [M+H]$^+$.

EXAMPLE 10

5-Methyl-3-phenyl-4-[1-(3-trifluoromethyl-phenyl)-1H-imidazol-4-yl]-isoxazole As described for Example 3, 4-(1H-imidazol-4-yl)-5-methyl-3-phenyl-isoxazole (112.6 mg, 0.5 mmol) was converted, using 3-(trifluoromethyl)phenylboronic acid instead of 4-fluorophenylboronic acid, to the title compound (55 mg, 30%) which was obtained as a white solid. MS (ESI): m/e=370.0 [M+H]$^+$.

EXAMPLE 11

3-[4-(5-Methyl-3-phenyl-isoxazol-4-yl)-imidazol-1-yl]-benzoic acid methyl ester As described for Example 3, 4-(1H-imidazol-4-yl)-5-methyl-3-phenyl-isoxazole (112.6 mg, 0.5 mmol) was converted, using 3-methoxycarbonylphenylboronic acid instead of 4-fluorophenylboronic acid, to the title compound (65 mg, 40%) which was obtained as a white solid. MS (ESI): m/e=360.0 [M+H]$^+$.

EXAMPLE 12

1-{4-[4-(5-Methyl-3-phenyl-isoxazol-4-yl)-imidazol-1-yl]-phenyl}-ethanone

As described for Example 1f, 4-(1H-imidazol-4-yl)-5-methyl-3-phenyl-isoxazole (100 mg, 0.44 mmol) instead of 4-(1H-imidazol-4-yl)-3-phenyl-isoxazole was converted to the title compound (88 mg, 58%) which was obtained as a yellow gum. MS: m/e=344.1 [M+H]$^+$.

EXAMPLE 13

5-Methyl-4-[1-(4-nitro-phenyl)-1H-imidazol-4-yl]-3-phenyl-isoxazole

As described for Example 12, 4-(1H-imidazol-4-yl)-5-methyl-3-phenyl-isoxazole (100 mg, 0.44 mmol) using 1-fluoro-4-nitrobenzene instead of 4-fluoroacetophenone was converted to the title compound (97 mg, 64%) which was obtained as an off-white solid. MS: m/e=347.3 [M+H]$^+$.

EXAMPLE 14

5-Methyl-3-phenyl-4-[1-(4-trifluoromethyl-phenyl)-1H-imidazol-4-yl]-isoxazole

As described for Example 12, 4-(1H-imidazol-4-yl)-5-methyl-3-phenyl-isoxazole (100 mg, 0.44 mmol) using 4-fluorobenzotrifluoride instead of 4-fluoroacetophenone was converted to the title compound (40 mg, 24%) which was obtained as an off-white solid. MS: m/e=370.0 [M+H]$^+$.

EXAMPLE 15

5-Methyl-3-phenyl-4-[1-(2-trifluoromethyl-phenyl)-1H-imidazol-4-yl]-isoxazole

As described for Example 3, 4-(1H-imidazol-4-yl)-5-methyl-3-phenyl-isoxazole (112.6 mg, 0.5 mmol) was converted, using 2-(trifluoromethyl)phenylboronic acid (190 mg, 1.0 mmol) instead of 4-fluorophenylboronic acid, to the title compound (37 mg, 20%) which was obtained as a white solid. MS (ESI): m/e=369.9 [M+H]$^+$.

EXAMPLE 16

4-[4-(5-Methyl-3-phenyl-isoxazol-4-yl)-imidazol-1-yl]-benzonitrile

As described for Example 3, 4-(1H-imidazol-4-yl)-5-methyl-3-phenyl-isoxazole (112.6 mg, 0.5 mmol) was converted, using 4-cyanophenylboronic acid instead of 4-fluorophenylboronic acid, to the title compound (60 mg, 37%) which was obtained as a white solid. MS (ESI): m/e=327.0 [M+H]$^+$.

EXAMPLE 17

3-[4-(5-Methyl-3-phenyl-isoxazol-4-yl)-imidazol-1-yl]-benzonitrile

As described for Example 3, 4-(1H-imidazol-4-yl)-5-methyl-3-phenyl-isoxazole (112.6 mg, 0.5 mmol) was converted, using 3-cyanophenylboronic acid instead of 4-fluorophenylboronic acid, to the title compound (49 mg, 30%) which was obtained as a white solid. MS (ESI): m/e=327.0 [M+H]$^+$.

EXAMPLE 18

4-[1-(4-Methoxy-phenyl)-1H-imidazol-4-yl]-5-methyl-3-phenyl-isoxazole

As described for Example 2b, 4-(1H-imidazol-4-yl)-5-methyl-3-phenyl-isoxazole (100 mg, 0.44 mmol) using 4-iodoanisole instead of iodobenzene was converted to the title compound (22 mg, 15%) which was obtained as a yellow gum. MS: m/e=332.3 [M+H]$^+$.

EXAMPLE 19

4-[1-(4-Ethoxy-phenyl)-1H-imidazol-4-yl]-5-methyl-3-phenyl-isoxazole

As described for Example 3, 4-(1H-imidazol-4-yl)-5-methyl-3-phenyl-isoxazole (112.6 mg, 0.5 mmol) was converted, using 4-ethoxyphenylboronic acid instead of 4-fluorophenylboronic acid, to the title compound (50 mg, 29%) which was obtained as a white solid. MS (ESI): m/e=346.0 [M+H]$^+$.

EXAMPLE 20

4-[1-(2-Ethoxy-phenyl)-1H-imidazol-4-yl]-5-methyl-3-phenyl-isoxazole

As described for Example 3, 4-(1H-imidazol-4-yl)-5-methyl-3-phenyl-isoxazole (112.6 mg, 0.5 mmol) was converted, using 2-ethoxyphenylboronic acid instead of 4-fluorophenylboronic acid, to the title compound (21 mg, 12%) which was obtained as a white solid. MS (ESI): m/e=346.0 [M+H]$^+$.

EXAMPLE 21

5-Methyl-4-[1-(4-methylsulfanyl-phenyl)-1H-imidazol-4-yl]-3-phenyl-isoxazole

As described for Example 3, 4-(1H-imidazol-4-yl)-5-methyl-3-phenyl-isoxazole (112.6 mg, 0.5 mmol) was converted, using 4-methylthiophenylboronic acid instead of 4-fluorophenylboronic acid, to the title compound (78 mg, 45%) which was obtained as a white solid. MS (ESI): m/e=348.0 [M+H]$^+$.

EXAMPLE 22

{4-[4-(5-Methyl-3-phenyl-isoxazol-4-yl)-imidazol-1-yl]-phenyl}-carbamic acid tert-butyl ester As described for Example 3, 4-(1H-imidazol-4-yl)-5-methyl-3-phenyl-isoxazole (112.6 mg, 0.5 mmol) was converted, using 4-(N-Boc-amino)phenylboronic acid instead of 4-fluorophenylboronic acid, to the title compound (10 mg, 5%) which was obtained as a white solid (ESI). MS: m/e=417.0 [M+H]$^+$.

EXAMPLE 23

4-[1-(3,4-Difluoro-phenyl)-1H-imidazol-4-yl]-5-methyl-3-phenyl-isoxazole

As described for Example 3, 4-(1H-imidazol-4-yl)-5-methyl-3-phenyl-isoxazole (112.6 mg, 0.5 mmol) was converted, using 3, 4-difluorophenylboronic instead of 4-fluorophenylboronic acid, to the title compound (34 mg, 20%) which was obtained as a white solid. MS (ESI): m/e=337.9 [M+H]$^+$.

EXAMPLE 24

4-[1-(3,5-Difluoro-phenyl)-1H-imidazol-4-yl]-5-methyl-3-phenyl-isoxazole

As described for Example 3, 4-(1H-imidazol-4-yl)-5-methyl-3-phenyl-isoxazole (112.6 mg, 0.5 mmol) was converted, using 3,5-difluorophenylboronic acid instead of 4-fluorophenylboronic acid, to the title compound (51 mg, 30%) which was obtained as a white solid (ESI). MS: m/e=337.9 [M+H]$^+$.

EXAMPLE 25

4-[1-(3-Chloro-4-fluoro-phenyl)-1H-imidazol-4-yl]-5-methyl-3-phenyl-isoxazole

As described for Example 3, 4-(1H-imidazol-4-yl)-5-methyl-3-phenyl-isoxazole (112.6 mg, 0.5 mmol) was converted, using 3-chloro-4-fluorophenylboronic acid instead of 4-fluorophenylboronic acid, to the title compound (8 mg, 5%) which was obtained as a white solid. MS (ESI): m/e=353.9 [M+H]⁺.

EXAMPLE 26

4-[1-(3,4-Dichloro-phenyl)-1H-imidazol-4-yl]-5-methyl-3-phenyl-isoxazole

As described for Example 3, 4-(1H-imidazol-4-yl)-5-methyl-3-phenyl-isoxazole (112.6 mg, 0.5 mmol) was converted, using 3,4-dichlorophenylboronic acid instead of 4-fluorophenylboronic acid, to the title compound (18 mg, 10%) which was obtained as a white solid. MS (ESI): m/e=369.9 [M+H]⁺.

EXAMPLE 27

4-[1-(2,4-Dichloro-phenyl)-1H-imidazol-4-yl]-5-methyl-3-phenyl-isoxazole

As described for Example 3, 4-(1H-imidazol-4-yl)-5-methyl-3-phenyl-isoxazole (112.6 mg, 0.5 mmol) was converted, using 2,5-dichlorophenylboronic instead of 4-fluorophenylboronic acid, to the title compound (9 mg, 5%) which was obtained as a white solid. MS (ESI): m/e=369.9 [M+H]⁺.

EXAMPLE 28

4-[1-(3,5-Bis-trifluoromethyl-phenyl)-1H-imidazol-4-yl]-5-methyl-3-phenyl-isoxazole As described for Example 3, 4-(1H-imidazol-4-yl)-5-methyl-3-phenyl-isoxazole (112.6 mg, 0.5 mmol) was converted, using 3,5-bis(trifluoromethyl)phenylboronic instead of 4-fluorophenylboronic acid, to the title compound (17 mg, 8%) as a white solid. MS (ESI): m/e=437.9 [M+H]⁺.

EXAMPLE 29

4-[1-(2-Fluoro-5-methoxy-phenyl)-1H-imidazol-4-yl]-5-methyl-3-phenyl-isoxazole

As described for Example 3, 4-(1H-imidazol-4-yl)-5-methyl-3-phenyl-isoxazole (112.6 mg, 0.5 mmol) was converted, using 2-fluoro-5-methoxyphenylboronic acid instead of 4-fluorophenylboronic acid, to the title compound (6 mg, 3.4%) which was obtained as a white solid. MS (ESI): m/e=350.0 [M+H]⁺.

EXAMPLE 30

1-{4-[4-(5-Ethyl-3-phenyl-isoxazol-4-yl)-imidazol-1-yl]-phenyl}-ethanone a) 5-Ethyl-3-phenyl-isoxazole-4-carboxylic acid methyl ester To a solution of 3-oxo-pentanoic acid methyl ester (19.3 g, 0.15 mol) in methanol (30 mL) was added a solution of sodium methoxide (8.1 g, 0.15 mol) in methanol (30 mL) dropwise under ice-bath cooling keeping the temperature below 30° C. The reaction mixture was then stirred at room temperature for 30 min. Then a solution of (E)- and/or (Z)-N-hydroxy-benzenecarboximidoyl chloride (21.7 g, 0.14 mol, in Example 1a) in methanol (78 mL) was added to this mixture under ice-bath cooling keeping the temperature below 0° C. After adding, the ice-bath was removed and stirring was continued overnight at room temperature. The resulting mixture was concentrated under reduced pressure, and the residue was partitioned between ethyl acetate and water. The aqueous phase was further extracted with ethyl acetate. The combined organic extracts were then dried over sodium sulphate and concentrated to give the title compound as a yellow oil which was used in the next reaction without further purification. MS: m/e=232.1 [M+H]⁺.

b) 5-Ethyl-3-phenyl-isoxazole-4-carboxylic acid

To a solution of 5-ethyl-3-phenyl-isoxazole-4-carboxylic acid methyl ester (12.0 g, 51 mmol) in THF (50 mL), was added a solution of LiOH.H₂O (10.8 g, 255 mmol) in water (25 mL) in one portion. The reaction mixture was then heated under reflux for 12 h. After cooling to room temperature and concentration, the remaining mixture was extracted with ethyl acetate and dried over sodium sulphate. Evaporation afforded the title compound (8.01 g, 72%) as yellow solid. MS: m/e=218.1 [M+H]⁺.

c) 2-Bromo-1-(5-ethyl-3-phenyl-isoxazol-4-yl)-ethanone

To a solution of 5-ethyl-3-phenyl-isoxazole-4-caboxylic acid (5.45 g, 25 mmol) was added thionyl chloride (8.92 g, 75 mmol) in one portion. The reaction mixture was then heated at 60° C. for 4 h until gas evolution ceased. After cooling to room temperature and concentration, diazomethane (1.0 M) in ether (100 mL, 0.1 mol, freshly prepared) was added to the resulting brown oil under ice-bath cooling keeping the temperature below 0° C. After complete addition, the reaction mixture was allowed to stand overnight at 0° C. Then aqueous hydrobromic acid (50 mL, 40% w/w) was added dropwise to the reaction mixture under ice-bath cooling keeping the temperature below 0° C. Then the mixture was stirred at 0° C. for 30 min and at room temperature for another 30 min. The layers were separated and the aqueous layer extracted with diethyl ether. The combined organic layers were then washed with water and brine, and the organic extract dried over sodium sulphate and evaporated to afford the product (4.06 g, 75%) as a brown oil. MS: m/e=295.1 [M+H]⁺.

d) 5-Ethyl-4-(1H-imidazol-4-yl)-3-phenyl-isoxazole

A mixture of 2-bromo-1-(5-ethyl-3-phenyl-isoxazol-4-yl)-ethanone (0.47 g, 2 mmol) and formamide (5 mL) was heated at 160° C. overnight. After cooling to room temperature, water (20 mL) was then added and the resulting mixture extracted with ethyl acetate. The combined organic extracts were then evaporated to leave the title compound (0.45 g, 95%) as a brown solid. MS: m/e=240.1 [M+H]⁺.

e) 1-{4-[4-(5-Ethyl-3-phenyl-isoxazol-4-yl)-imidazol-1-yl]-phenyl}-ethanone

As described for Example 1f, 5-ethyl-4-(1H-imidazol-4-yl)-3-phenyl-isoxazole (100 mg, 0.43 mmol) instead of 4-(1H-imidazol-4-yl)-3-phenyl-isoxazole was converted to the title compound (56 mg, 38%) which was obtained as a colourless gum after purification by preparative HPLC on reversed phase eluting with [0.1% aq NH₃(25%)]. MS: m/e=362.1 [M+H]⁺.

EXAMPLE 31

5-Ethyl-4-[1-(4-nitro-phenyl)-1H-imidazol-4-yl]-3-phenyl-isoxazole

As described for Example 30 e), 5-ethyl-4-(1H-imidazol-4-yl)-3-phenyl-isoxazole (100 mg, 0.43 mmol) was converted using 1-fluoro-4-nitro-benzene instead of 4-fluoroacetophenone to the title compound (45 mg, 30%) which was obtained as a white solid. MS: m/e=347.1 [M+H]⁺.

EXAMPLE 32

2-[4-(5-Methyl-3-phenyl-isoxazol-4-yl)-imidazol-1-yl]-pyridine

As described for Example 12, 4-(1H-imidazol-4-yl)-5-methyl-3-phenyl-isoxazole (100 mg, 0.44 mmol) using 2-fluoropyridine instead of 4-fluoroacetophenone was converted to the title compound (31 mg, 23%) which was obtained as an off-white solid. MS: m/e=303.1 [M+H]$^+$.

EXAMPLE 33

2-[4-(5-Methyl-3-phenyl-isoxazol-4-yl)-imidazol-1-yl]-pyrimidine

As described for Example 12, 4-(1H-imidazol-4-yl)-5-methyl-3-phenyl-isoxazole (100 mg, 0.44 mmol) using 2-chloropyrimidine instead of 4-fluoroacetophenone was converted to the title compound (92 mg, 68%) which was obtained as an off-white solid. MS: m/e=304.0 [M+H]$^+$.

EXAMPLE 34

4-(1-Benzyl-1H-imidazol-4-yl)-5-methyl-3-phenyl-isoxazole

A solution of 4-(1H-imidazol-4-yl)-5-methyl-3-phenyl-isoxazole (100 mg, 0.44 mmol) in DMF (2 mL) was added over 10 min to a suspension of NaH (20 mg, 0.47 mmol) in DMF (1 mL) at room temperature and after 30 min benzyl bromide (83.5 mg, 0.49 mmol) was added. After 2 h at room temperature, the mixture was poured into aqueous acetic acid (10%) and extracted with ethyl acetate. The organic extracts were then washed with water and brine, and then dried over sodium sulphate and evaporated. Purification by chromatography (SiO$_2$, heptane:ethyl acetate=1:1) afforded the title compound (88 mg, 63%) which was obtained as a colourless gum. MS: m/e=316.1 [M+H]$^+$.

EXAMPLE 35

4-[1-(4-Fluoro-benzyl)-1H-imidazol-4-yl]-5-methyl-3-phenyl-isoxazole

As described for Example 34, 4-(1H-imidazol-4-yl)-5-methyl-3-phenyl-isoxazole (100 mg, 0.44 mmol) using 4-fluorobenzyl bromide instead of benzyl bromide was converted to the title compound (104 mg, 70%) as a colourless gum. MS: m/e=334.1 [M+H]$^+$.

EXAMPLE 36

1-(4-{4-[3-(2-Fluoro-phenyl)-5-methyl-isoxazol-4-yl]-imidazol-1-yl}-phenyl)-ethanone a) (E)- and/or (Z)-2-Fluoro-benzaldehyde oxime As described for Example 1a, 2-fluorobenzaldehyde (10 g, 78 mmol) instead of benzaldehyde was converted to the title compound (9.1 g, 83%) which was obtained as a white solid. MS: m/e (EI)=139.0 [M].

b) (E)- and/or (Z)-N-Hydroxy-2-fluoro-benzenecarboximidoyl chloride

As described for Example 1b, (E)- and/or (Z)-2-fluoro-benzaldehyde oxime (8.9 g, 64 mmol) instead of (E)- and/or (Z)-4-benzaldehyde oxime was converted to the title compound (10.5 mg, 95%) which was obtained as a light yellow solid. MS: m/e=173.1 [M].

c) 1-[3-(2-Fluoro-phenyl)-5-methyl-isoxazol-4-yl]-ethanone

A solution of (E)- and/or (Z)-N-hydroxy-2-fluoro-benzenecarboximidoyl chloride (6.5 g, 37 mmol) in ethanol (29 mL) was added dropwise to a solution of acetylacetone (4.6 g, 46 mmol) containing sodium ethoxide (14.8 g, 46 mmol) in ethanol (83 mL) at ice-bath cooling temperature. After complete addition, the resulting mixture was allowed to warm up to room temperature and stirred for 1.5 h. The mixture was then acidified with HCl (6 N) and concentrated and the mixture extracted with ethyl acetate and then washed with water and brine and dried over sodium sulphate. Purification by chromatography (SiO$_2$, heptane:ethyl acetate=100:0 to 75:25) afforded the title compound (7.0 g, 85%) which was obtained as a light yellow liquid. MS: m/e=220.1 [M+H]$^+$.

d) 2-Bromo-1-[3-(2-fluoro-phenyl)-5-methyl-isoxazol-4-yl]-ethanone

As described for Example 1d, 1-[3-(2-fluoro-phenyl)-5-methyl-isoxazol-4-yl]-ethanone (4.4 g, 20 mmol) instead of 1-(3-phenyl-isoxazol-4-yl)-ethanone was converted to the title compound (4.5 g, 76%) which was obtained as alight yellow liquid. MS: m/e=298.1/300.1 [M+H]$^+$.

e) 3-(2-Fluoro-phenyl)-4-(1H-imidazol-4-yl)-5-methyl-isoxazole

As described for Example 1e, 2-bromo-1-[3-(2-fluoro-phenyl)-5-methyl-isoxazol-4-yl]-ethanone (4.0 g, 13 mmol) instead of 2-bromo-1-(3-phenyl-isoxazol-4-yl)-ethanone was converted to the title compound (1.6 g, 49%) which was obtained as a light yellow solid. MS: m/e=244.4 [M+H]$^+$.

f) 1-(4-{4-[3-(2-Fluoro-phenyl)-5-methyl-isoxazol-4-yl]-imidazol-1-yl}-phenyl)-ethanone As described for Example 1f, 3-(2-fluoro-phenyl)-4-(1H-imidazol-4-yl)-5-methyl-isoxazole (100 mg, 0.41 mmol) instead of 4-(1H-imidazol-4-yl)-3-phenyl-isoxazole was converted to the title compound (29 mg, 20%) which was obtained as a colourless gum. MS: m/e=362.1 [M+H]$^+$.

EXAMPLE 37

3-(2-Fluoro-phenyl)-5-methyl-4-[1-(4-nitro-phenyl)-1H-imidazol-4-yl]-isoxazole As described for Example 36, 3-(2-fluoro-phenyl)-4-(1H-imidazol-4-yl)-5-methyl-isoxazole (100 mg, 0.41 mmol) using 1-fluoro-4-nitrobenzene instead of 4-fluoroacetophenone was converted to the title compound (130 mg, 87%) which was obtained as an off-white solid. MS: m/e=365.0 [M+H]$^+$.

EXAMPLE 38

3-(2-Fluoro-phenyl)-4-[1-(4-methoxy-phenyl)-1H-imidazol-4-yl]-5-methyl-isoxazole To a solution of 3-(2-fluoro-phenyl)-4-(1H-imidazol-4-yl)-5-methyl-isoxazole (100 mg, 0.41 mmol) in DMSO (2 mL) was added copper(I) iodide (7.9 mg, 0.04 mmol), 4-iodoanisole (57 mg, 0.45 mmol), L-proline (9.5 mg, 0.08 mmol) and potassium carbonate (113.6 mg, 0.82 mmol) and the resulting mixture heated at 90° C. for 3 days. After cooling to room temperature the resulting mixture was poured into water and extracted with ethyl acetate. The organic extracts were then washed with water and brine, dried over sodium sulphate and evaporated. Purification by chromatography (SiO$_2$, heptane:ethyl acetate=1:1) afforded the title compound (5.7 mg, 4%) which was obtained as a light brown gum. MS: m/e=350.5 [M+H]$^+$.

EXAMPLE 39

2-{4-[3-(2-Fluoro-phenyl)-5-methyl-isoxazol-4-yl]-imidazol-1-yl}-pyrimidine

As described for Example 36, 3-(2-fluoro-phenyl)-4-(1H-imidazol-4-yl)-5-methyl-isoxazole (100 mg, 0.41 mmol) using 2-chloropyrimidine instead of 4-fluoroacetophenone was converted to the title compound (86 mg, 65%) which was obtained as an off-white solid. MS: m/e=322.4 [M+H]$^+$.

EXAMPLE 40

1-(4-{4-[3-(3-Fluoro-phenyl)-5-methyl-isoxazol-4-yl]-imidazol-1-yl}-phenyl)-ethanone a) (E)- and/or (Z)-3-Fluoro-benzaldehyde oxime As described for Example 1a, 3-fluorobenzaldehyde (6.75 g, 54 mmol) instead of benzaldehyde was converted to the title compound (7.04 g, 93%) which was obtained as a white solid. MS: m/e (EI)=139.0 [M].

b) (E)- and/or (Z)-N-Hydroxy-3-fluoro-benzenecarboximidoyl chloride

As described for Example 1b, (E)- and/or (Z)-3-fluoro-benzaldehyde oxime (6.9 g, 50 mmol) instead of (E)- and/or (Z)-4-benzaldehyde oxime was converted to the title compound (6.3 g, 73%) which was obtained as an off-white solid. MS: m/e=173.1 [M].

c) 1-[3-(3-Fluoro-phenyl)-5-methyl-isoxazol-4-yl]-ethanone

As described for Example 36c, (E)- and/or (Z)-N-hydroxy-3-fluoro-benzenecarboximidoyl chloride (3.15 g, 18 mmol) instead of (E)- and/or (Z)-N-hydroxy-2-fluoro-benzenecarboximidoyl chloride was converted to the title compound (3.49 g, 88%) which was obtained as a light yellow solid. MS: m/e=220.3 [M+H]$^+$.

d) 2-Bromo-1-[3-(3-fluoro-phenyl)-5-methyl-isoxazol-4-yl]-ethanone

As described for Example 1d, 1-[3-(3-fluoro-phenyl)-5-methyl-isoxazol-4-yl]-ethanone (4.9 g, 23 mmol) instead of 1-(3-phenyl-isoxazol-4-yl)-ethanone was converted to the title compound (4.66 g, 69%) which was obtained as a light yellow liquid. MS: m/e=296.2/298.2 [M+H]$^+$.

e) 3-(3-Fluoro-phenyl)-4-(1H-imidazol-4-yl)-5-methyl-isoxazole

As described for Example 1e, 2-bromo-1-[3-(3-fluoro-phenyl)-5-methyl-isoxazol-4-yl]-ethanone (4.58 g, 15 mmol) instead of 2-bromo-1-(3-phenyl-isoxazol-4-yl)-ethanone was converted to the title compound (1.99 g, 53%) which was obtained as a light yellow solid. MS: m/e=242.3 [M−H]$^−$ f) 1-(4-{4-[3-(3-Fluoro-phenyl)-5-methyl-isoxazol-4-yl]-imidazol-1-yl}-phenyl)-ethanone As described for Example 1f, 3-(3-fluoro-phenyl)-4-(1H-imidazol-4-yl)-5-methyl-isoxazole (100 mg, 0.41 mmol) instead of 4-(1H-imidazol-4-yl)-3-phenyl-isoxazole was converted to the title compound (84 mg, 57%) which was obtained as a colourless gum. MS: m/e=362.3 [M+H]$^+$.

EXAMPLE 41

3-(3-Fluoro-phenyl)-5-methyl-4-[1-(4-nitro-phenyl)-1H-imidazol-4-yl]-isoxazole

As described for Example 40, 3-(3-fluoro-phenyl)-4-(1H-imidazol-4-yl)-5-methyl-isoxazole (100 mg, 0.41 mmol) using 1-fluoro-4-nitrobenzene instead of 4-fluoroacetophenone was converted to the title compound (123 mg, 82%) which was obtained as an off-white solid. MS: m/e=365.0 [M+H]$^+$.

EXAMPLE 42

3-(3-Fluoro-phenyl)-4-[1-(4-methoxy-phenyl)-1H-imidazol-4-yl]-5-methyl-isoxazole As described for Example 38, 3-(3-fluoro-phenyl)-4-(1H-imidazol-4-yl)-5-methyl-isoxazole (100 mg, 0.41 mmol) instead of 3-(2-fluoro-phenyl)-4-(1H-imidazol-4-yl)-5-methyl-isoxazole was converted to the title compound (8 mg, 6%) which was obtained as a light yellow gum. MS: m/e=350.4 [M+H]$^+$.

EXAMPLE 43

2-{4-[3-(3-Fluoro-phenyl)-5-methyl-isoxazol-4-yl]-imidazol-1-yl}-pyrimidine

As described for Example 40, 3-(3-fluoro-phenyl)-4-(1H-imidazol-4-yl)-5-methyl-isoxazole (100 mg, 0.41 mmol) using 2-chloropyrimidine instead of 4-fluoroacetophenone was converted to the title compound (95 mg, 72%) which was obtained as an off-white solid. MS: m/e=322.4 [M+H]$^+$.

EXAMPLE 44

1-(4-{4-[3-(3-Bromo-phenyl)-5-methyl-isoxazol-4-yl]-imidazol-1-yl}-phenyl)-ethanone a) (E)- and/or (Z)-3-Bromo-benzaldehyde oxime As described for Example 1a, 3-bromobenzaldehyde (27.8 g, 150 mmol) instead of benzaldehyde was converted to the title compound (28.4 g, 95%) which was obtained as a light brown solid. MS: m/e=198.9/200.9 [M+H]$^+$.

b) (E)- and/or (Z)-N-Hydroxy-3-bromo-benzenecarboximidoyl chloride

As described for Example 1b, (E)- and/or (Z)-3-bromo-benzaldehyde oxime (28.4 g, 142 mmol) instead of (E)- and/or (Z)-4-benzaldehyde oxime was converted to the title compound (32.8 g, 99%) which was obtained as a light yellow solid. MS: m/e=233.0/235.0 [M].

c) 1-[3-(3-Bromo-phenyl)-5-methyl-isoxazol-4-yl]-ethanone

As described for Example 36c, (E)- and/or (Z)-N-hydroxy-3-bromo-benzenecarboximidoyl chloride (16.4 g, 70 mmol) instead of (E)- and/or (Z)-N-hydroxy-2-fluoro-benzenecarboximidoyl chloride was converted to the title compound (16.0 g, 88%) which was obtained as a light yellow liquid. MS: m/e=280.1/282.2 [M+H]$^+$.

d) 2-Bromo-1-[3-(3-bromo-phenyl)-5-methyl-isoxazol-4-yl]-ethanone

As described for Example 1d, 1-[3-(3-bromo-phenyl)-5-methyl-isoxazol-4-yl]-ethanone (5.3 g, 20 mmol) instead of 1-(3-phenyl-isoxazol-4-yl)-ethanone was converted to the title compound (5.2 g, 72%) which was obtained as a light yellow liquid. MS: m/e=357.8/359.9 [M+H]$^+$.

e) 3-(3-Bromo-phenyl)-4-(1H-imidazol-4-yl)-5-methyl-isoxazole

As described for Example 1e, 2-bromo-1-[3-(3-bromo-phenyl)-5-methyl-isoxazol-4-yl]-ethanone (5.1 g, 14 mmol) instead of 2-bromo-1-(3-phenyl-isoxazol-4-yl)-ethanone was converted to the title compound (1.85 g, 43%) which was obtained as an off-white solid. MS: m/e=302.2/304.1[M+H]$^+$.

f) 1-(4-{4-[3-(3-Bromo-phenyl)-5-methyl-isoxazol-4-yl]-imidazol-1-yl}-phenyl)-ethanone As described for Example 1f, 3-(3-bromo-phenyl)-4-(1H-imidazol-4-yl)-5-methyl-isoxazole (91 mg, 0.3 mmol) instead of 4-(1H-imidazol-4-yl)-3-phenyl-isoxazole was converted to the title compound (84 mg, 67%) which was obtained as an off-white solid. MS: m/e=422.1/424.1 [M+H]$^+$.

EXAMPLE 45

3-(3-Bromo-phenyl)-5-methyl-4-[1-(4-nitro-phenyl)-1H-imidazol-4-yl]-isoxazole

As described for Example 44, 3-(3-bromo-phenyl)-4-(1H-imidazol-4-yl)-5-methyl-isoxazole (91 mg, 0.3 mmol) using 1-fluoro-4-nitrobenzene instead of 4-fluoroacetophenone was converted to the title compound (50 mg, 39%) which was obtained as a light yellow solid. MS: m/e=425.1/427.1 [M+H]$^+$.

EXAMPLE 46

1-(4-{4-[3-(4-Fluoro-phenyl)-5-methyl-isoxazol-4-yl]-imidazol-1-yl}-phenyl)-ethanone a) (E)- and/or (Z)-4-Fluoro-benzaldehyde oxime As described for Example 1a, 4-fluorobenzaldehyde (7.0 g, 56 mmol) instead of benzaldehyde was converted to the title compound (6.4 g, 81%) which was obtained as a white solid. MS: m/e (EI)=139.1 [M].

b) (E)- and/or (Z)-N-hydroxy-4-fluoro-benzenecarboximidoyl chloride

As described for Example 1b, (E)- and/or (Z)-4-fluoro-benzaldehyde oxime (9.3 g, 67 mmol) instead of (E)- and/or (Z)-benzaldehyde oxime was converted to the title compound (10.0 g, 87%) which was obtained as a white solid. MS: m/e (EI)=173.0 [M].

c) 1-[3-(4-Fluoro-phenyl)-5-methyl-isoxazol-4-yl]-ethanone

As described for Example 36c, (E)- and/or (Z)-N-hydroxy-4-fluoro-benzenecarboximidoyl chloride (5.0 g, 29 mmol) instead of (E)- and/or (Z)-N-hydroxy-2-fluoro-benzenecarboximidoyl chloride was converted to the title compound (5.6 g, 89%) which was obtained as a white solid. MS: m/e=220.3 [M+H]$^+$.

d) 2-Bromo-1-[3-(4-fluoro-phenyl)-5-methyl-isoxazol-4-yl]-ethanone

As described for Example 1d, 1-[3-(4-fluoro-phenyl)-5-methyl-isoxazol-4-yl]-ethanone (2.1 g, 9 mmol) instead of 1-(3-phenyl-isoxazol-4-yl)-ethanone was converted to the title compound (1.6 g, 58%) which was obtained as a light yellow liquid. MS: m/e=374.0/376.1 [M+H]$^+$.

e) 3-(4-Fluoro-phenyl)-4-(1H-imidazol-4-yl)-5-methyl-isoxazole

As described for Example 1e, 2-bromo-1-[3-(4-fluoro-phenyl)-5-methyl-isoxazol-4-yl]-ethanone (1.56 g, 5 mmol) instead of 2-bromo-1-(3-phenyl-isoxazol-4-yl)-ethanone was converted to the title compound (627 mg, 49%) which was obtained as a light brown solid. MS: m/e=244.4 [M+H]$^+$.

f) 1-(4-{4-[3-(4-Fluoro-phenyl)-5-methyl-isoxazol-4\-yl]-imidazol-1-yl}-phenyl)-ethanone As described for Example 1f, 3-(4-fluoro-phenyl)-4-(1H-imidazol-4-yl)-5-methyl-isoxazole (97 mg, 0.4 mmol) instead of 4-(1H-imidazol-4-yl)-3-phenyl-isoxazole was converted to the title compound (71 mg, 49%) which was obtained as an off-white foam. MS: m/e=362.0 [M+H]$^+$.

EXAMPLE 47

3-(4-Fluoro-phenyl)-5-methyl-4-[1-(4-nitro-phenyl)-1H-imidazol-4-yl]-isoxazole

As described for Example 46, 3-(4-fluoro-phenyl)-4-(1H-imidazol-4-yl)-5-methyl-isoxazole (97 mg, 0.4 mmol) using 1-fluoro-4-nitrobenzene instead of 4-fluoroacetophenone was converted to the title compound (105 mg, 72%) which was obtained as a light yellow solid. MS: m/e=365.1 [M+H]$^+$.

EXAMPLE 48

2-{4-[3-(4-Fluoro-phenyl)-5-methyl-isoxazol-4-yl]-imidazol-1-yl}-pyrimidine

As described for Example 46, 3-(4-fluoro-phenyl)-4-(1H-imidazol-4-yl)-5-methyl-isoxazole (97 mg, 0.4 mmol) using 2-chloropyrimidine instead of 4-fluoroacetophenone was converted to the title compound (75 mg, 58%) as a light yellow solid. MS: m/e=322.1 [M+H]$^+$.

EXAMPLE 49

1-(4-{4-[3-(4-Bromo-phenyl)-5-methyl-isoxazol-4-yl]-imidazol-1-yl}-phenyl)-ethanone a) (E)- and/or (Z)-4-Fluoro-benzaldehyde oxime As described for Example 1a, 4-bromobenzaldehyde (2.0 g, 11 mmol) instead of benzaldehyde was converted to the title compound (2.0 g, 94%) which was obtained as a white solid. MS: m/e=198.0/200.1 [M+H]$^+$.

b) (E)- and/or (Z)-N-hydroxy-4-fluoro-benzenecarboximidoyl chloride

As described for Example 1b, (E)- and/or (Z)-4-bromo-benzaldehyde oxime (1.95 g, 10 mmol) instead of (E)- and/or (Z)-benzaldehyde oxime was converted to the title compound (1.8 g, 80%) which was obtained as a light yellow solid. MS: m/e (EI)=233.0/234.9 [M].

c) 1-[3-(4-Bromo-phenyl)-5-methyl-isoxazol-4-yl]-ethanone

As described for Example 36c, (E)- and/or (Z)-N-hydroxy-4-bromo-benzenecarboximidoyl chloride (2.35 g, 10 mmol) instead of (E)- and/or (Z)-N-hydroxy-2-fluoro-benzenecarboximidoyl chloride was converted to the title compound (2.35 g, 84%) which was obtained as a light yellow oil. MS: m/e=280.1/282.1 [M+H]$^+$.

d) 2-Bromo-1-[3-(4-bromo-phenyl)-5-methyl-isoxazol-4-yl]-ethanone

As described for Example 1d, 1-[3-(4-bromo-phenyl)-5-methyl-isoxazol-4-yl]-ethanone (2.49 g, 9 mmol) instead of 1-(3-phenyl-isoxazol-4-yl)-ethanone was converted to the title compound (1.49 g, 47%) which was obtained as a light yellow oil. MS: m/e=358.1/359.9 [M+H]$^+$.

e) 3-(4-Bromo-phenyl)-4-(1H-imidazol-4-yl)-5-methyl-isoxazole

As described for Example 1e, 2-bromo-1-[3-(4-bromo-phenyl)-5-methyl-isoxazol-4-yl]-ethanone (359 mg, 2 mmol)

instead of 2-bromo-1-(3-phenyl-isoxazol-4-yl)-ethanone was converted to the title compound (184 mg, 60%) which was obtained as an off-white solid. MS: m/e=304.0/306.1 [M+H]$^+$.

f) 1-(4-{4-[3-(4-Bromo-phenyl)-5-methyl-isoxazol-4-yl]-imidazol-1-yl}-phenyl)-ethanone As described for Example 1f, 3-(4-bromo-phenyl)-4-(1H-imidazol-4-yl)-5-methyl-isoxazole (91 mg, 0.3 mmol) instead of 4-(1H-imidazol-4-yl)-3-phenyl-isoxazole was converted to the title compound (81 mg, 64%) which was obtained as a light yellow solid. MS: m/e 421.9/424.0 [M+H]$^+$.

EXAMPLE 50

3-(4-Bromo-phenyl)-5-methyl-4-[1-(4-nitro-phenyl)-1H-imidazol-4-yl]-isoxazole

As described for Example 49, 3-(4-bromo-phenyl)-4-(1H-imidazol-4-yl)-5-methyl-isoxazole (91 mg, 0.3 mmol) using 1-fluoro-4-nitrobenzene instead of 4-fluoroacetophenone was converted to the title compound (117 mg, 92%) which was obtained as a light yellow solid. MS: m/e 425.0/426.9 [M+H]$^+$.

EXAMPLE 51

2-{4-[3-(4-Bromo-phenyl)-5-methyl-isoxazol-4-yl]-imidazol-1-yl}-pyrimidine

As described for Example 49, 3-(4-bromo-phenyl)-4-(1H-imidazol-4-yl)-5-methyl-isoxazole (61 mg, 0.2 mmol) using 2-chloropyrimidine instead of 4-fluoroacetophenone was converted to the title compound (56 mg, 73%) which was obtained as a light yellow solid. MS: m/e=382.0/384.1 [M+H]$^+$.

EXAMPLE 52

4-(1-Benzyl-1H-imidazol-4-yl)-3-(4-bromo-phenyl)-5-methyl-isoxazole

A mixture containing 3-(4-bromo-phenyl)-4-(1H-imidazol-4-yl)-5-methyl-isoxazole (61 mg, 0.2 mmol), benzyl bromide (34 mg, 0.2 mmol) and potassium carbonate (55 mg, 0.4 mmol) in DMF (1.2 mL) was heated at 140° C. for 4 h. After cooling to room temperature the resulting mixture was poured into water and extracted with ethyl acetate. The organic extracts were then washed with water and brine, dried over sodium sulphate and evaporated to give a yellow solid (59 mg). This was then dissolved in 1-methyl-2-pyrrolidone (1 mL) and thiourea (23 mg, 0.3 mmol) was added and the resulting mixture heated in the microwave at 150° C. for 1.5 h. After cooling, the mixture was poured onto sodium hydroxide (1 N) and extracted with ethyl acetate. The organic extracts were then washed with water and brine, dried over sodium sulphate and evaporated. Purification by chromatography (SiO$_2$, heptane:ethyl acetate=100:0 to 50:50) afforded the title compound (11 mg, 14%) which was obtained as a light yellow solid. MS: m/e (EI)=393.0/395.0 [M].

EXAMPLE 53

1-(4-{4-[3-(3,4-Difluoro-phenyl)-5-methyl-isoxazol-4-yl]-imidazol-1-yl}-phenyl)-ethanone a) (E)- and/or (Z)-3,4-Difluoro-benzaldehyde oxime As described for Example 1a, 3,4-difluorobenzaldehyde (7.4 g, 50 mmol) instead of benzaldehyde was converted to the title compound (7.7 g, 98%) which was obtained as a white solid. MS: m/e (EI)=157.0 [M].

b) (E)- and/or (Z)-N-Hydroxy-3,4-difluoro-benzenecarboximidoyl chloride

As described for Example 1b, (E)- and/or (Z)-3,4-difluoro-benzaldehyde oxime (7.6 g, 48 mmol) instead of (E)- and/or (Z)-benzaldehyde oxime was converted to the title compound (6.9 g, 75%) which was obtained as a white solid. MS: m/e (EI)=191.0 [M].

c) 1-[3-(3,4-Difluoro-phenyl)-5-methyl-isoxazol-4-yl]-ethanone

As described for Example 36c, (E)- and/or (Z)-N-hydroxy-3,4-difluoro-benzenecarboximidoyl chloride (6.78 g, 35 mmol) instead of (E)- and/or (Z)-N-hydroxy-2-fluoro-benzenecarboximidoyl chloride was converted to the title compound (1.1 g, 13%) which was obtained as a light yellow solid. MS: m/e (EI)=237.1 [M].

d) 2-Bromo-1-[3-(3,4-difluoro-phenyl)-5-methyl-isoxazol-4-yl]-ethanone

As described for Example 1d, 1-[3-(3,4-difluoro-phenyl)-5-methyl-isoxazol-4-yl]-ethanone (1.69 g, 7 mmol) instead of 1-(3-phenyl-isoxazol-4-yl)-ethanone was converted to the title compound (1.18 g, 52%) which was obtained as a light yellow oil. MS: m/e (EI)=315.2/317.2 [M].

e) 3-(3,4-Difluoro-phenyl)-4-(1H-imidazol-4-yl)-5-methyl-isoxazole

As described for Example 1e, 2-bromo-1-[3-(3,4-difluoro-phenyl)-5-methyl-isoxazol-4-yl]-ethanone (740 mg, 2.3 mmol) instead of 2-bromo-1-(3-phenyl-isoxazol-4-yl)-ethanone was converted to the title compound (365 mg, 60%) which was obtained as a yellow solid. MS: m/e 260.0 [M−H]$^-$.

f) 1-(4-{4-[3-(3,4-Difluoro-phenyl)-5-methyl-isoxazol-4-yl]-imidazol-1-yl}-phenyl)-ethanone As described for Example 1f, 3-(3,4-difluoro-phenyl)-4-(1H-imidazol-4-yl)-5-methyl-isoxazole (78 mg, 0.3 mmol) instead of 4-(1H-imidazol-4-yl)-3-phenyl-isoxazole was converted to the title compound (43 mg, 43%) which was obtained as an off-white solid. MS: m/e=380.3 [M+H]$^+$.

EXAMPLE 54

3-(3,4-Difluoro-phenyl)-5-methyl-4-[1-(4-nitro-phenyl)-1H-imidazol-4-yl]-isoxazole As described for Example 53, 3-(3,4-difluoro-phenyl)-4-(1H-imidazol-4-yl)-5-methyl-isoxazole (78 mg, 0.3 mmol) using 1-fluoro-4-nitrobenzene instead of 4-fluoroacetophenone was converted to the title compound (89 mg, 76%) which was obtained as a light yellow solid. MS: m/e=383.1 [M+H]$^+$.

EXAMPLE 55

3-(3,4-Difluoro-phenyl)-5-methyl-4-[1-(4-trifluoromethyl-phenyl)-1H-imidazol-4-yl]-isoxazole As described for Example 53, 3-(3,4-difluoro-phenyl)-4-(1H-imidazol-4-yl)-5-methyl-isoxazole (78 mg, 0.3 mmol) using 4-fluorobenzotrifluoride instead of 4-fluoroacetophenone was converted to the title compound (12 mg, 10%) which was obtained as a colourless gum. MS: m/e=406.3 [M+H]$^+$.

EXAMPLE 56

2-{4-[3-(3,4-Difluoro-phenyl)-5-methyl-isoxazol-4-yl]-imidazol-1-yl}-pyrimidine

As described for Example 53, 3-(3,4-difluoro-phenyl)-4-(1H-imidazol-4-yl)-5-methyl-isoxazole (78 mg, 0.3 mmol) using 2-chloropyrimidine instead of 4-fluoroacetophenone was converted to the title compound (48 mg, 47%) which was obtained as an off-white solid. MS: m/e=406.3 [M+H]$^+$.

EXAMPLE 57

1-{4-[2-Methyl-4-(5-methyl-3-phenyl-isoxazol-4-yl)-imidazol-1-yl]-phenyl}-ethanone a) 5-Methyl-4-(2-methyl-1H-imidazol-4-yl)-3-phenyl-isoxazole A solution of the free base of acetamidine (622 mg, 11 mmol) [which was freshly prepared by treatment of acetamidine HCl (3 g) and partitioning between sodium hydroxide (32%, 4 mL) and dichloromethane-methanol (10%)] in dichloromethane (25 mL) was added over a 1 h period to a solution of 4-(bromoacetyl)-5-methyl-3-phenylisoxazole (commercially available) (1.0 g, 4 mmol) in dichloromethane (5 mL). The resulting mixture was then stirred overnight at room temperature. The mixture was then filtered. The resulting filtrate was then extracted with HCl (1 N) and then the combined aqueous extracts basified with sodium hydroxide and extracted with dichloromethane. The organic extracts were then washed with water and brine, then dried over sodium sulphate and evaporated. Purification by chromatography (SiO$_2$, heptane:ethyl acetate=100:0 to 50:50) afforded the title compound (197 mg, 23%) which was obtained as a white solid. The initial reaction precipitate was worked up following the same procedure as above to give the title compound (379 mg, 44%) as a white solid. MS: m/e=240.1 [M+H]$^+$.

b) 1-{4-[2-Methyl-4-(5-methyl-3-phenyl-isoxazol-4-yl)-imidazol-1-yl]-phenyl}-ethanone As described for Example 1f, 5-methyl-4-(2-methyl-1H-imidazol-4-yl)-3-phenyl-isoxazole (70 mg, 0.3 mmol) instead of 4-(1H-imidazol-4-yl)-3-phenyl-isoxazole was converted to the title compound (30 mg, 26%) which was obtained as a light yellow gum. MS: m/e=358.1 [M+H]$^+$.

EXAMPLE 58

5-Methyl-4-[2-methyl-1-(4-nitro-phenyl)-1H-imidazol-4-yl]-3-phenyl-isoxazole

As described for Example 57, 5-methyl-4-(2-methyl-1H-imidazol-4-yl)-3-phenyl-isoxazole (70 mg, 0.3 mmol) using 1-fluoro-4-nitrobenzene instead of 4-fluoroacetophenone was converted to the title compound (38 mg, 36%) which was obtained as an off-white solid. MS: m/e=361.4 [M+H]$^+$.

EXAMPLE 59

5-Methyl-4-[2-methyl-1-(4-trifluoromethyl-phenyl)-1H-imidazol-4-yl]-3-phenyl-isoxazole As described for Example 57, 5-methyl-4-(2-methyl-1H-imidazol-4-yl)-3-phenyl-isoxazole (70 mg, 0.3 mmol) using 4-fluorobenzotrifluoride instead of 4-fluoroacetophenone was converted to the title compound (10 mg, 9%) which was obtained as a light yellow solid. MS: m/e=384.1 [M+H]$^+$.

EXAMPLE 60

2-[2-Methyl-4-(5-methyl-3-phenyl-isoxazol-4-yl)-imidazol-1-yl]-pyrimidine

As described for Example 57, 5-methyl-4-(2-methyl-1H-imidazol-4-yl)-3-phenyl-isoxazole (70 mg, 0.3 mmol) using 2-chloropyrimidine instead of 4-fluoroacetophenone was converted to the title compound (45 mg, 48%) which was obtained as a white solid. MS: m/e=318.1 [M+H]$^+$.

EXAMPLE 61

2-[2-Cyclopropyl-4-(5-methyl-3-phenyl-isoxazol-4-yl)-imidazol-1-yl]-pyrimidine a) 4-(2-Cyclopropyl-1H-imidazol-4-yl)-5-methyl-3-phenyl-isoxazole As described for Example 57, 4-(bromoacetyl)-5-methyl-3-phenylisoxazole (commercially available) (1.5 g, 5 mmol) using cyclopropylcarbamidine HCl instead of acetamidine HCl was converted to the title compound (1.2 g, 85%) which was obtained as an off-white solid. MS: m/e=266.3 [M+H]$^+$.

b) 2-[2-Cyclopropyl-4-(5-methyl-3-phenyl-isoxazol-4-yl)-imidazol-1-yl]-pyrimidine As described for Example 60, 4-(2-cyclopropyl-1H-imidazol-4-yl)-5-methyl-3-phenyl-isoxazole (70 mg, 0.3 mmol) instead of 5-methyl-4-(2-methyl-1H-imidazol-4-yl)-3-phenyl-isoxazole was converted to the title compound (50 mg, 39%) which was obtained as an off-white solid. MS: m/e=344.1 [M+H]$^+$.

EXAMPLE 62

1-{4-[2-Benzyloxymethyl-4-(5-methyl-3-phenyl-isoxazol-4-yl)-imidazol-1-yl]-phenyl}-ethanone a) 2-Benzyloxy-N-[2-(5-methyl-3-phenyl-isoxazol-4-yl)-2-oxo-ethyl]-acetamide A solution of 4-(bromoacetyl)-5-methyl-3-phenylisoxazole (commercially available) (7.0 g, 25 mmol) in chloroform (30 mL) was added dropwise to a solution of hexamethylenetetramine (3.7 g, 26 mmol) in chloroform (55 mL) and the resulting mixture stirred at room temperature overnight. The mixture was the filtered and the filtrate concentrated to afford an orange foam (11.1 g) which was then dissolved in methanol (110 mL) and then HCl (conc., 14 mL, 105 mmol) added and the resulting mixture stirred at room temperature overnight. The resulting mixture was then filtered and the filtrate triturated with diethyl ether. The resulting precipitate was removed, and the filtrate concentrated to give a brown gum (6.0 g) which was then dissolved in ethyl acetate (57 mL) and water (28 mL) added. To this mixture was added sodium hydrogen carbonate (4.97 g, 59 mmol) followed by the dropwise addition of benzyloxyacetyl chloride (4.2 g, 23 mmol) and the resulting mixture stirred at room temperature for 1 h.

The organic layer was then separated, washed with water and brine, dried over sodium sulphate and evaporated. Purification by chromatography (SiO$_2$, heptane:ethyl acetate=100:0 to 50:50) afforded the title compound (3.45 g, 38%) which was obtained as a light brown solid. MS: m/e=365.0 [M+H]$^+$.

b) 4-(Benzyloxymethyl-1H-imidazol-4-yl)-5-methyl-3-phenyl-isoxazole

To a refluxing solution of 2-benzyloxy-N-[2-(5-methyl-3-phenyl-isoxazol-4-yl)-2-oxo-ethyl]-acetamide (3.35 g, 9 mmol) in acetic acid (10 mL) was added ammonium acetate (14.2 g, 184 mmol) portionwise over 1.5 h. Then the mixture was heated for a subsequent 2 h under reflux and then allowed to cool down to room temperature overnight. The mixture was then poured onto water and extracted with ethyl acetate. The organic layer was then washed with water and brine, dried over sodium sulphate and evaporated. Purification by chromatography (SiO$_2$, heptane:ethyl acetate=100:0 to 50:50) afforded the title compound (2.36 g, 74%) which was obtained as a light yellow solid. MS: m/e=346.1 [M+H]$^+$.

c) 1-{4-[2-Benzyloxymethyl-4-(5-methyl-3-phenyl-isoxazol-4-yl)-imidazol-1-yl]-phenyl}-ethanone As described for Example 1f, 4-(2-benzyloxymethyl-1H-imidazol-4-yl)-5-methyl-3-phenyl-isoxazole (60 mg, 0.17 mmol) instead of 4-(1H-imidazol-4-yl)-3-phenyl-isoxazole was converted to the title compound (17 mg, 21%) which was obtained as a light yellow gum. MS: m/e=464.1 [M+H]$^+$.

EXAMPLE 63

4-[2-Benzyloxymethyl-1-(4-nitro-phenyl)-1H-imidazol-4-yl]-5-methyl-3-phenyl-isoxazole As described for Example 63, 4-(2-benzyloxymethyl-1H-imidazol-4-yl)-5-methyl-3-phenyl-isoxazole (38 mg, 0.11 mmol) using 1-fluoro-4-nitrobenzene instead of 4-fluoroacetophenone was converted to the title compound (41 mg, 80%) which was obtained as a yellow solid. MS: m/e=467.0 [M+H]$^+$.

EXAMPLE 64

4-[2-Benzyloxymethyl-1-(4-trifluoromethyl-phenyl)-1H-imidazol-4-yl]-5-methyl-3-phenyl-isoxazole As described for Example 63, 4-(2-benzyloxymethyl-1H-imidazol-4-yl)-5-methyl-3-phenyl-isoxazole (200 mg, 0.58 mmol) using 4-fluorobenzotrifluoride instead of 4-fluoroacetophenone was converted to the title compound (38 mg, 13%) which was obtained as a light yellow gum. MS: m/e=490.1 [M+H]$^+$.

EXAMPLE 65

4-[2-Benzyloxymethyl-4-(5-methyl-3-phenyl-isoxazol-4-yl)-imidazol-1-yl]-benzonitrile As described for Example 63, 4-(2-benzyloxymethyl-1H-imidazol-4-yl)-5-methyl-3-phenyl-isoxazole (100 mg, 0.29 mmol) using 4-fluorobenzonitrile instead of 4-fluoroacetophenone was converted to the title compound (106 mg, 82%) which was obtained as a white foam. MS: m/e=447.4 [M+H]$^+$.

EXAMPLE 66

2-[2-Benzyloxymethyl-4-(5-methyl-3-phenyl-isoxazol-4-yl)-imidazol-1-yl]-pyrimidine As described for Example 63, 4-(2-benzyloxymethyl-1H-imidazol-4-yl)-5-methyl-3-phenyl-isoxazole (60 mg, 0.17 mmol) using 2-chloropyrimidine instead of 4-fluoroacetophenone was converted to the title compound (30 mg, 41%) which was obtained as an off-white solid. MS: m/e=424.3 [M+H]$^+$.

EXAMPLE 67

4-(1-Benzyl-2-benzyloxymethyl-1H-imidazol-4-yl)-5-methyl-3-phenyl-isoxazole

As described for Example 34, 4-(2-benzyloxymethyl-1H-imidazol-4-yl)-5-methyl-3-phenyl-isoxazole (100 mg, 0.29 mmol) instead of 4-(1H-imidazol-4-yl)-5-methyl-3-phenyl-isoxazole was converted to the title compound (100 mg, 79%) which was obtained as a light yellow gum. MS: m/e=436.1 [M+H]$^+$.

EXAMPLE 68

4-[2-Benzyloxymethyl-1-(5-methyl-isoxazol-3-ylmethyl)-1H-imidazol-4-yl]-5-methyl-3-phenyl-isoxazole As described for Example 67, 4-(2-benzyloxymethyl-1H-imidazol-4-yl)-5-methyl-3-phenyl-isoxazole (100 mg, 0.29 mmol) using 3-(chloromethyl)-5-methylisoxazole instead of benzyl bromide was converted to the title compound (80 mg, 63%) which was obtained as a light yellow gum. MS: m/e=441.4 [M+H]$^+$.

EXAMPLE 69

5-Methyl-4-[1-(5-methyl-isoxazol-3-ylmethyl)-2-phenyl-1H-imidazol-4-yl]-3-phenyl-isoxazole a) 5-Methyl-3-phenyl-4-(2-phenyl-1H-imidazol-4-yl)-isoxazole As described for Example 57, 4-(bromoacetyl)-5-methyl-3-phenylisoxazole (commercially available) (1.0 g, 4 mmol) using benzamidine HCl instead of acetamidine HCl was converted to the title compound (992 mg, 92%) which was obtained as a white solid. MS: m/e=302.1 [M+H]$^+$.

b) 5-Methyl-4-[1-(5-methyl-isoxazol-3-ylmethyl)-2-phenyl-1H-imidazol-4-yl]-3-phenyl-isoxazole As described for Example 68, 5-methyl-3-phenyl-4-(2-phenyl-1H-imidazol-4-yl)-isoxazole (100 mg, 0.33 mmol) instead of 4-(2-benzyloxymethyl-1H-imidazol-4-yl)-5-methyl-3-phenyl-isoxazole was converted to the title compound (43 mg, 33%) which was obtained as a colourless gum. MS: m/e=397.1 [M+H]$^+$.

EXAMPLE 70

5-Methyl-3-phenyl-4-(1-p-tolyl-1H-imidazol-4-yl)-isoxazole

As described for Example 3, 4-(1H-imidazol-4-yl)-5-methyl-3-phenyl-isoxazole (100 mg, 0.44 mmol) was converted, using 4-methylphenylphenylboronic acid (120 mg, 0.88 mmol) instead of 4-fluorophenylboronic acid, to the title

EXAMPLE 71

N-Cyclopropylmethyl-4-[4-(5-methyl-3-phenyl-isoxazol-4-yl)-imidazol-1-yl]-benzamide a) 4-[4-(5-Methyl-3-phenyl-isoxazol-4-yl)-imidazol-1-yl]-benzoic acid ethyl ester As described for Example 1, 4-(1H-imidazol-4-yl)-5-methyl-3-phenyl-isoxazole (2.25 g, 10.0 mmol) was converted, using 4-fluorobenzoic acid ethyl ester (1.54 g, 10.0 mmol) instead of 4-fluoroacetophenone, to the title compound (2.68 g, 72%) which was obtained as brown oil. MS: m/e=374.1 $[M+H]^+$.

b) 4-[4-(5-Methyl-3-phenyl-isoxazol-4-yl)-imidazol-1-yl]-benzoic acid

To a solution of 4-[4-(5-methyl-3-phenyl-isoxazol-4-yl)-imidazol-1-yl]-benzoic acid ethyl ester (1.50 g, 4.0 mmol) in THF (20 mL) was added a solution of lithium hydroxide monohydrate (0.5 g, 12 mmol) in water (10 mL). The resulting mixture was concentrated, acidified and extracted with ethyl acetate. The combined organic extracts were dried with $Na_2SO_4$ and evaporated to afford the title compound (1.38 g, 99%) which was obtained as a light yellow solid. MS m/e=346.1 $[M+H]^+$.

c) N-Cyclopropylmethyl-4-[4-(5-methyl-3-phenyl-isoxazol-4-yl)-imidazol-1-yl]-benzamide To a solution of 4-[4-(5-methyl-3-phenyl-isoxazol-4-yl)-imidazol-1-yl]-benzoic acid (100 mg, 0.29 mmol) in DMF (2 mL), was added 1-ethyl-3-(3-dimethylaminopropyl)-carbodiimide (85.9 mg, 0.45 mmol) and N-hydroxybenzotriazole (60.7 mg, 0.45 mmol), followed by adding cyclopropylmethylamine (26 mg, 0.36 mmol) and triethylamine (75 mg, 0.75 mmol). The reaction mixture was stirred at room temperature overnight. Purification by preparative HPLC on reversed phase eluting with an acetonitrile/water [0.1% aq $NH_3$ (25%)] gradient afforded the title compound (14 mg, 13%) which was obtained as a white solid. MS m/e=398.9 $[M+H]^+$.

EXAMPLE 72

4-[4-(5-Methyl-3-phenyl-isoxazol-4-yl)-imidazol-1-yl]-N-prop-2-ynyl-benzamide

As described for Example 71c, 4-[4-(5-methyl-3-phenyl-isoxazol-4-yl)-imidazol-1-yl]-benzoic acid (100 mg, 0.29 mmol) was converted, using prop-2-ynlamine instead of cyclopropylmethylamine, to the title compound (15 mg, 13%) which was obtained as an off-white solid. MS: m/e=382.9 $[M+H]^+$.

EXAMPLE 73

4-[4-(5-Methyl-3-phenyl-isoxazol-4-yl)-imidazol-1-yl]-N-(3-morpholin-4-yl-propyl)-benzamide As described for Example 71c, 4-[4-(5-methyl-3-phenyl-isoxazol-4-yl)-imidazol-1-yl]-benzoic acid (100 mg, 0.29 mmol) was converted, using 3-morpholin-4-yl-propylamine instead of cyclopropylmethylamine, to the title compound (13 mg, 10%) which was obtained as an off-white solid. MS: m/e=472.0 $[M+H]^+$.

EXAMPLE 74

N-Cyclopropyl-4-[4-(5-methyl-3-phenyl-isoxazol-4-yl)-imidazol-1-yl]-benzamide

As described for Example 71c, 4-[4-(5-methyl-3-phenyl-isoxazol-4-yl)-imidazol-1-yl]-benzoic acid (100 mg, 0.29 mmol) was converted, using cyclopropylamine instead of cyclopropylmethylamine, to the title compound (14 mg, 12%) which was obtained as an off-white solid. MS: m/e=384.9 $[M+H]^+$.

EXAMPLE 75

N-Cyclobutyl-4-[4-(5-methyl-3-phenyl-isoxazol-4-yl)-imidazol-1-yl]-benzamide

As described for Example 71c, 4-[4-(5-methyl-3-phenyl-isoxazol-4-yl)-imidazol-1-yl]-benzoic acid (100 mg, 0.29 mmol) was converted, using cyclobutylamine instead of cyclopropylmethylamine, to the title compound (13 mg, 11%) which was obtained as an off-white solid. MS: m/e=398.9 $[M+H]^+$.

EXAMPLE 76

N-Cyclopentyl-4-[4-(5-methyl-3-phenyl-isoxazol-4-yl)-imidazol-1-yl]-benzamide

As described for Example 71c, 4-[4-(5-methyl-3-phenyl-isoxazol-4-yl)-imidazol-1-yl]-benzoic acid (100 mg, 0.29 mmol) was converted, using cyclopentylamine instead of cyclopropylmethylamine, to the title compound (14 mg, 11%) which was obtained as an off-white solid. MS: m/e=413.0 $[M+H]^+$.

EXAMPLE 77

4-[4-(5-Methyl-3-phenyl-isoxazol-4-yl)-imidazol-1-yl]-N-(tetrahydro-pyran-4-yl)-benzamide As described for Example 71c, 4-[4-(5-methyl-3-phenyl-isoxazol-4-yl)-imidazol-1-yl]-benzoic acid (100 mg, 0.29 mmol) was converted, using tetrahydro-pyran-4-ylamine instead of cyclopropylmethylamine, to the title compound (16 mg, 13%) which was obtained as an off-white solid. MS: m/e=428.9 $[M+H]^+$.

EXAMPLE 78

4-[4-(5-Methyl-3-phenyl-isoxazol-4-yl)-imidazol-1-yl]-N-pyridin-3-ylmethyl-benzamide As described for Example 71c, 4-[4-(5-methyl-3-phenyl-isoxazol-4-yl)-imidazol-1-yl]-benzoic acid (100 mg, 0.29 mmol) was converted, using pyridine-3-ylamine instead of cyclopropylmethylamine, to the title compound (15 mg, 12%) which was obtained as an off-white solid. MS: m/e=436.3 $[M+H]^+$.

EXAMPLE 79

4-[4-(5-Methyl-3-phenyl-isoxazol-4-yl)-imidazol-1-yl]-N-pyridin-4-ylmethyl-benzamide As described for Example 71c, 4-[4-(5-methyl-3-phenyl-isoxazol-4-yl)-imidazol-1-yl]-benzoic acid (100 mg, 0.29 mmol) was converted, using pyridine-4-ylamine instead of cyclopropylmethylamine, to the title compound (13 mg, 10%) which was obtained as an off-white solid. MS: m/e=436.3 [M+H]+.

EXAMPLE 80

N-(3-Fluoro-phenyl)-4-[4-(5-methyl-3-phenyl-isoxazol-4-yl)-imidazol-1-yl]-benzamide As described for Example 71c, 4-[4-(5-methyl-3-phenyl-isoxazol-4-yl)-imidazol-1-yl]-benzoic acid (100 mg, 0.29 mmol) was converted, using 3-fluorophenylamine instead of cyclopropylmethylamine, to the title compound (13 mg, 10%) which was obtained as an off-white solid. MS: m/e=438.9 [M+H]+.

EXAMPLE 81

4-[1-(3-Ethoxy-phenyl)-1H-imidazol-4-yl]-5-methyl-3-phenyl-isoxazole

As described for Example 3, 4-(1H-imidazol-4-yl)-5-methyl-3-phenyl-isoxazole (68 mg, 0.3 mmol) was converted, using 3-ethoxyphenylboronic acid instead of 4-fluorophenylboronic acid, to the tide compound (8 mg, 7%) which was obtained as an off-white solid. MS: m/e=346.5 [M+H]+.

EXAMPLE 82

5-Methyl-4-[1-(3-nitro-phenyl)-1H-imidazol-4-yl]-3-phenyl-isoxazole

As described for Example 3, 4-(1H-imidazol-4-yl)-5-methyl-3-phenyl-isoxazole (100 mg, 0.44 mmol) was converted, using 3-nitrophenylboronic acid (120 mg, 0.88 mmol) instead of 4-fluorophenylboronic acid, to the title compound (113 mg, 73%) which was obtained as a light yellow foam. MS: m/e=347.1 [M+H]+.

EXAMPLE 83

N-Cyclopropylmethyl-3-[4-(5-methyl-3-phenyl-isoxazol-4-yl)-imidazol-1-yl]-benzamide a) 3-[4-(5-Methyl-3-phenyl-isoxazol-4-yl)-imidazol-1-yl]-benzoic acid ethyl ester As described for Example 3, 4-(1H-imidazol-4-yl)-5-methyl-3-phenyl-isoxazole (2.25 g, 10.0 mmol) was converted, using 3-ethoxycarbonylphenylboronic acid (2.89 g, 15 mmol), instead of 4-fluorophenylboronic acid, which after purification by chromatography (SiO₂, heptane:ethyl acetate=50:50) afforded the title compound (1.9 g, 52%) which was obtained as a light yellow solid. MS: m/e=374.1 [M+H]+.

b) 3-[4-(5-Methyl-3-phenyl-isoxazol-4-yl)-imidazol-1-yl]-benzoic acid

As described for Example 71b, 3-[4-(5-methyl-3-phenyl-isoxazol-4-yl)-imidazol-1-yl]-benzoic acid ethyl ester (1.5 g, 4.0 mmol) was converted to the title compound (1.38 g, 99%) which was obtained as a light yellow solid. MS: m/e=346.1 [M+H]+.

c) N-Cyclopropylmethyl-3-[4-(5-methyl-3-phenyl-isoxazol-4-yl)-imidazol-1-yl]-benzamide As described for Example 71c, 3-[4-(5-methyl-3-phenyl-isoxazol-4-yl)-imidazol-1-yl]-benzoic acid (100 mg, 0.29 mmol), instead of 4-[4-(5-methyl-3-phenyl-isoxazol-4-yl)-imidazol-1-yl]-benzoic acid was converted to the title compound (50 mg, 43%) which was obtained as an off-white solid. MS: m/e=399.1 [M+H]+.

EXAMPLE 84

N-Cyclopropyl-3-[4-(5-methyl-3-phenyl-isoxazol-4-yl)-imidazol-1-yl]-benzamide

As described for Example 71c, cyclopropylamine was converted, using 3-[4-(5-methyl-3-phenyl-isoxazol-4-yl)-imidazol-1-yl]-benzoic acid (100 mg, 0.29 mmol) instead of 4-[4-(5-methyl-3-phenyl-isoxazol-4-yl)-imidazol-1-yl]-benzoic acid, to the title compound (53 mg, 47%) which was obtained as an off-white solid. MS: m/e=385.0 [M+H]+.

EXAMPLE 85

N-Cyclobutyl-3-[4-(5-methyl-3-phenyl-isoxazol-4-yl)-imidazol-1-yl]-benzamide

As described for Example 71, cyclobutylamine was converted, using 3-[4-(5-methyl-3-phenyl-isoxazol-4-yl)-imidazol-1-yl]-benzoic acid (100 mg, 0.29 mmol) instead of 4-[4-(5-methyl-3-phenyl-isoxazol-4-yl)-imidazol-1-yl]-benzoic acid, to the title compound (52 mg, 45%) which was obtained as an off-white solid. MS: m/e=399.1 [M+H]+.

EXAMPLE 86

N-Cyclopentyl-3-[4-(5-methyl-3-phenyl-isoxazol-4-yl)-imidazol-1-yl]-benzamide

As described for Example 71, cyclopentylamine was converted, using 3-[4-(5-methyl-3-phenyl-isoxazol-4-yl)-imidazol-1-yl]-benzoic acid (100 mg, 0.29 mmol) instead of 4-[4-(5-methyl-3-phenyl-isoxazol-4-yl)-imidazol-1-yl]-benzoic acid, to the title compound (49 mg, 41%) which was obtained as an off-white solid. MS: m/e=413.0 [M+H]+.

EXAMPLE 87

3-[4-(5-Methyl-3-phenyl-isoxazol-4-yl)-imidazol-1-yl]-N-(tetrahydro-pyran-4-yl)-benzamide As described for Example 71, tetrahydro-pyran-4-ylamine was converted, using 3-[4-(5-methyl-3-phenyl-isoxazol-4-yl)-imidazol-1-yl]-benzoic acid (100 mg, 0.29 mmol) instead of 4-[4-(5-methyl-3-phenyl-isoxazol-4-yl)-imidazol-1-yl]-benzoic acid, to the title compound (52 mg, 42%) which was obtained as an off-white solid. MS: m/e=413.0 [M+H]+.

EXAMPLE 88

4-[1-(2-Chloro-phenyl)-1H-imidazol-4-yl]-5-methyl-3-phenyl-isoxazole

As described for Example 3, 4-(1H-imidazol-4-yl)-5-methyl-3-phenyl-isoxazole (68.2 mg, 0.3 mmol) was converted, using 2-chlorophenylboronic acid instead of 4-fluorophenylboronic acid, to the title compound (11 mg, 10%) which was obtained as an off-white solid. MS: m/e=336.5 [M+H]+.

EXAMPLE 89

4-[1-(2-Bromo-phenyl)-1H-imidazol-4-yl]-5-methyl-3-phenyl-isoxazole

As described for Example 3, 4-(1H-imidazol-4-yl)-5-methyl-3-phenyl-isoxazole (68.2 mg, 0.3 mmol) was converted, using 2-bromophenylboronic acid instead of 4-fluorophenylboronic acid, to the title compound (12 mg, 11%) which was obtained as an off-white solid. MS: m/e=381.5[M+H]+.

EXAMPLE 90

N-Cyclopropylmethyl-2-[4-(5-methyl-3-phenyl-isoxazol-4-yl)-imidazol-1-yl]-benzamide a) 2-[4-(5-Methyl-3-phenyl-isoxazol-4-yl)-imidazol-1-yl]-benzoic acid methyl ester As described for Example 1, 2-(1H-imidazol-4-yl)-5-methyl-3-phenyl-isoxazole (2.25 g, 10.0 mmol) was converted, using 2-fluorobenzoic acid methyl ester (1.54 g, 10.0 mmol) instead of 4-fluoroacetophenone, to the title compound (1.47 g, 39%) which was obtained as brown oil. MS: m/e=360.1 [M+H]+.

b) 2-[4-(5-Methyl-3-phenyl-isoxazol-4-yl)-imidazol-1-yl]-benzoic acid

As described for Example 71c, 2-[4-(5-methyl-3-phenyl-isoxazol-4-yl)-imidazol-1-yl]-benzoic acid methyl ester (1.5 g, 4.0 mmol) was converted to the title compound (1.38 g, 99%) which was obtained as a light yellow solid. MS m/e=346.1 [M+H]+.

c) N-Cyclopropylmethyl-2-[4-(5-methyl-3-phenyl-isoxazol-4-yl)-imidazol-1-yl]-benzamide As described for Example 71 c, 2-[4-(5-methyl-3-phenyl-isoxazol-4-yl)-imidazol-1-yl]-benzoic acid (100 mg, 0.29 mmol) was converted to the title compound (43 mg, 37%) which was obtained as a white solid. MS m/e=399.1 [M+H]+.

EXAMPLE 91

2-[4-(5-Methyl-3-phenyl-isoxazol-4-yl)-imidazol-1-yl]-N-prop-2-ynyl-benzamide

As described for Example 71, prop-2-ynylamine was converted, using 2-[4-(5-methyl-3-phenyl-isoxazol-4-yl)-imidazol-1-yl]-benzoic acid (100 mg, 0.29 mmol) instead of 4-[4-(5-methyl-3-phenyl-isoxazol-4-yl)-imidazol-1-yl]-benzoic acid, to the title compound (28 mg, 25%) which was obtained as an off-white solid. MS: m/e=383.1 [M+H]+.

EXAMPLE 92

N-Cyclobutyl-2-[4-(5-methyl-3-phenyl-isoxazol-4-yl)-imidazol-1-yl]-benzamide

As described for Example 71, cyclobutylamine was converted, using 2-[4-(5-methyl-3-phenyl-isoxazol-4-yl)-imidazol-1-yl]-benzoic acid (100 mg, 0.29 mmol) instead of 4-[4-(5-methyl-3-phenyl-isoxazol-4-yl)-imidazol-1-yl]-benzoic acid, to the title compound (53 mg, 46%) which was obtained as an off-white solid. MS: m/e=399.1 [M+H]+.

EXAMPLE 93

N-Cyclopentyl-2-[4-(5-methyl-3-phenyl-isoxazol-4-yl)-imidazol-1-yl]-benzamide

As described for Example 71, cyclopentylamine was converted, using 2-[4-(5-methyl-3-phenyl-isoxazol-4-yl)-imidazol-1-yl]-benzoic acid (100 mg, 0.29 mmol) instead of 4-[4-(5-methyl-3-phenyl-isoxazol-4-yl)-imidazol-1-yl]-benzoic acid, to the title compound (48 mg, 40%) which was obtained as an off-white solid. MS: m/e=413.1 [M+H]+.

EXAMPLE 94

2-[4-(5-Methyl-3-phenyl-isoxazol-4-yl)-imidazol-1-yl]-N-(tetrahydro-pyran-4-yl)-benzamide As described for Example 71, tetrahydro-pyran-4-ylamine was converted, using 2-[4-(5-methyl-3-phenyl-isoxazol-4-yl)-imidazol-1-yl]-benzoic acid (100 mg, 0.29 mmol) instead of 4-[4-(5-methyl-3-phenyl-isoxazol-4-yl)-imidazol-1-yl]-benzoic acid, to the title compound (47 mg, 37%) which was obtained as an off-white solid. MS: m/e=429.1 [M+H]+.

EXAMPLE 95

4-{5-[3-(3-Fluoro-phenyl)-5-methyl-isoxazol-4-yl]-imidazol-1-yl}-benzoic acid ethyl ester As described for Example 1, 3-(3-fluoro-phenyl)-4-(1H-imidazol-4-yl)-5-methyl-isoxazole (3.89 g, 16.0 mmol) was converted, using 3-fluorobenzoic acid ethyl ester instead of 4-fluoroacetophenone, to the title compound (3.34 g, 53%) which was obtained as a yellow solid. MS: m/e=391.9[M+H]+.

EXAMPLE 96

N-Cyclopropylmethyl-4-{4-[3-(3-fluoro-phenyl)-5-methyl-isoxazol-4-yl]-imidazol-1-yl}-benzamide a) 4-{5-[3-(3-Fluoro-phenyl)-5-methyl-isoxazol-4-yl]-imidazol-1-yl}-benzoic acid As described for Example 71b, 4-{5-[3-(3-fluoro-phenyl)-5-methyl-isoxazol-4-yl]-imidazol-1-yl}-benzoic acid ethyl ester (3.2 g, 8.2 mmol) was converted to the title compound (2.82 g, 95%) which was obtained as an off-yellow solid. MS m/e=363.1 [M+H]+.

b) N-Cyclopropylmethyl-4-{4-[3-(3-fluoro-phenyl)-5-methyl-isoxazol-4-yl]-imidazol-1-yl}-benzamide As described for Example 71c, cyclopropylmethylamine was converted, using 4-{5-[3-(3-fluoro-phenyl)-5-methyl-isoxazol-4-yl]-imidazol-1-yl}-benzoic acid (100 mg, 0.28 mmol) instead of 4-[4-(5-methyl-3-phenyl-isoxazol-4-yl)-imidazol-1-yl]-benzoic acid, to the title compound (59 mg, 52%) which was obtained as an off-white solid. MS: m/e=417.0 [M+H]+.

EXAMPLE 97

4-{4-[3-(3-Fluoro-phenyl)-5-methyl-isoxazol-4-yl]-imidazol-1-yl}-N-prop-2-ynyl-benzamide As described for Example 71c, prop-2-ynylamine was converted, using 4-{5-[3-(3-fluoro-phenyl)-5-methyl-isoxazol-4-yl]-imidazol-1-yl}-benzoic acid (100 mg, 0.28 mmol) instead of 4-[4-(5-methyl-3-phenyl-isoxazol-4-yl)-imidazol-1-yl]-benzoic acid, to the title compound (42 mg, 38%) which was obtained as an off-white solid. MS: m/e=401.0 [M+H]+.

EXAMPLE 98

N-Cyclopropyl-4-{4-[3-(3-fluoro-phenyl)-5-methyl-isoxazol-4-yl]-imidazol-1-yl}-benzamide As described for Example 71c, cyclopropylamine was converted, using 4-{5-[3-(3-fluoro-phenyl)-5-methyl-isoxazol-4-yl]-imidazol-1-yl}-benzoic acid (100 mg, 0.28 mmol) instead of 4-[4-(5-methyl-3-phenyl-isoxazol-4-yl)-imidazol- 1-yl]-benzoic acid, to the title compound (30 mg, 27%) which was obtained as an off-white solid. MS: m/e=403.0 [M+H]+.

EXAMPLE 99

N-Cyclobutyl-4-{4-[3-(3-fluoro-phenyl)-5-methyl-isoxazol-4-yl]-imidazol-1-yl}-benzamide As described for Example 71c, cyclobutylamine was converted, using 4-{5-[3-(3-fluoro-phenyl)-5-methyl-isoxazol-4-yl]-imidazol-1-yl}-benzoic acid (100 mg, 0.28 mmol) instead of 4-[4-(5-methyl-3-phenyl-isoxazol-4-yl)-imidazol-1-yl]-benzoic acid, to the title compound (43 mg, 35%) which was obtained as an off-white solid. MS: m/e=417.0 [M+H]+.

EXAMPLE 100

N-Cyclopentyl-4-{4-[3-(3-fluoro-phenyl)-5-methyl-isoxazol-4-yl]-imidazol-1-yl}-benzamide As described for Example 71c, cyclopentylamine was converted, using 4-{5-[3-(3-fluoro-phenyl)-5-methyl-isoxazol-4-yl]-imidazol-1-yl}-benzoic acid (100 mg, 0.28 mmol) instead of 4-[4-(5-methyl-3-phenyl-isoxazol-4-yl)-imidazol-1-yl]-benzoic acid, to the title compound (15 mg, 13%) which was obtained as an off-white solid. MS: m/e=431.0 [M+H]+.

EXAMPLE 101

4-{4-[3-(3-Fluoro-phenyl)-5-methyl-isoxazol-4-yl]-imidazol-1-yl}-N-(2-hydroxy-ethyl)-benzamide As described for Example 71c, 2-hydroxy-ethylamine was converted, using 4-{5-[3-(3-fluoro-phenyl)-5-methyl-isoxazol-4-yl]-imidazol-1-yl}-benzoic acid (100 mg, 0.28 mmol) instead of 4-[4-(5-methyl-3-phenyl-isoxazol-4-yl)-imidazol-1-yl]-benzoic acid, to the title compound (34 mg, 30%) which was obtained as an off-white solid. MS: m/e=407.0 [M+H]+.

EXAMPLE 102

4-{4-[3-(3-Fluoro-phenyl)-5-methyl-isoxazol-4-yl]-imidazol-1-yl}-N-(2-morpholin-4-yl-ethyl)-benzamide As described for Example 71c, 2-morpholin-4-yl-ethylamine was converted, using 4-{5-[3-(3-fluoro-phenyl)-5-methyl-isoxazol-4-yl]-imidazol-1-yl}-benzoic acid (100 mg, 0.28 mmol) instead of 4-[4-(5-methyl-3-phenyl-isoxazol-4-yl)-imidazol-1-yl]-benzoic acid, to the title compound (14 mg, 11%) which was obtained as an off-white solid. MS: m/e=476.1 [M+H]+.

EXAMPLE 103

4-{4-[3-(3-Fluoro-phenyl)-5-methyl-isoxazol-4-yl]-imidazol-1-yl}-N-(3-morpholin-4-yl-propyl)-benzamide As described for Example 71c, 3-morpholin-4-yl-propylamine was converted, using 4-{5-[3-(3-fluoro-phenyl)-5-methyl-isoxazol-4-yl]-imidazol-1-yl}-benzoic acid (100 mg, 0.28 mmol) instead of 4-[4-(5-methyl-3-phenyl-isoxazol-4-yl)-imidazol-1-yl]-benzoic acid, to the title compound (24 mg, 18%) which was obtained as an off-white solid. MS: m/e=490.0 [M+H]+.

EXAMPLE 104

4-{4-[3-(3-Fluoro-phenyl)-5-methyl-isoxazol-4-yl]-imidazol-1-yl}-N-[2-(1H-imidazol-4-yl)-ethyl]-benzamide As described for Example 71c, 2-(1H-imidazol-4-yl)-ethylamine was converted, using 4-{5-[3-(3-fluoro-phenyl)-5-methyl-isoxazol-4-yl]-imidazol-1-yl}-benzoic acid (100 mg, 0.28 mmol) instead of 4-[4-(5-methyl-3-phenyl-isoxazol-4-yl)-imidazol-1-yl]-benzoic acid, to the title compound (62 mg, 50%) which was obtained as an off-white solid. MS: m/e=455.1 [M+H]+.

EXAMPLE 105

4-{4-[3-(3-Fluoro-phenyl)-5-methyl-isoxazol-4-yl]-imidazol-1-yl}-N-furan-2-ylmethyl-benzamide As described for Example 71c, furan-2-ylmethylamine was converted, using 4-{5-[3-(3-fluoro-phenyl)-5-methyl-isoxazol-4-yl]-imidazol-1-yl}-benzoic acid (100 mg, 0.28 mmol) instead of 4-[4-(5-methyl-3-phenyl-isoxazol-4-yl)-imidazol-1-yl]-benzoic acid, to the title compound (44 mg, 36%) which was obtained as an off-white solid. MS: m/e=443.0 [M+H]+.

EXAMPLE 106

4-{4-[3-(3-Fluoro-phenyl)-5-methyl-isoxazol-4-yl]-imidazol-1-yl}-N-pyridin-2-ylmethyl-benzamide As described for Example 71c, pyridin-2-ylmethylamine was converted, using 4-{5-[3-(3-fluoro-phenyl)-5-methyl-isoxazol-4-yl]-imidazol-1-yl}-benzoic acid (100 mg, 0.28 mmol) instead of 4-[4-(5-methyl-3-phenyl-isoxazol-4-yl)-imidazol-1-yl]-benzoic acid, to the title compound (16 mg, 13%) which was obtained as an off-white solid. MS: m/e=454.0 [M+H]+.

EXAMPLE 107

N-(3-Fluoro-phenyl)-4-{4-[3-(3-fluoro-phenyl)-5-methyl-isoxazol-4-yl]-imidazol-1-yl}-benzamide As described for Example 71c, 3-fluoro-phenylamine was converted, using 4-{5-[3-(3-fluoro-phenyl)-5-methyl-isoxazol-4-yl]-imidazol-1-yl}-benzoic acid (100 mg, 0.28 mmol) instead of 4-[4-(5-methyl-3-phenyl-isoxazol-4-yl)-imidazol-1-yl]-benzoic acid, to the title compound (46 mg, 37%) which was obtained as an off-white solid. MS: m/e=457.0 [M+H]+.

EXAMPLE 108

N-Cyclopropylmethyl-3-{4-[3-(3-fluoro-phenyl)-5-methyl-isoxazol-4-yl]-imidazol-1-yl}-benzamide a) 3-{5-[3-(3-Fluoro-phenyl)-5-methyl-isoxazol-4-yl]-imidazol-1-yl}-benzoic acid ethyl ester As described for Example 3, 3-(3-fluoro-phenyl)-4-(1H-imidazol-4-yl)-5-methyl-isoxazole (2.43 g, 10 mmol) was converted, using of 3-ethoxycarbonylphenylboronic acid instead of 4-fluorophenylboronic acid, through chromatography (SiO$_2$, ethyl acetate: hexane=20:10) to the title compound (1.26 mg, 32%) which was obtained as a light yellow solid. MS: m/e=392.1 [M+H]+.

b) 3-{5-[3-(3-Fluoro-phenyl)-5-methyl-isoxazol-4-yl]-imidazol-1-yl}-benzoic acid As described for Example 71b, 3-{5-[3-(3-fluoro-phenyl)-5-methyl-isoxazol-4-yl]-imidazol-1-yl}-benzoic acid ethyl ester (1.25 g, 3.0 mmol) was converted to the title compound (0.54 g, 50%) which was obtained as a yellow solid. MS m/e=363.1 [M+H]$^+$.

c) N-Cyclopropylmethyl-3-{4-[3-(3-fluoro-phenyl)-5-methyl-isoxazol-4-yl]-imidazol-1-yl}-benzamide As described for Example 71c, cyclopropylmethylamine was converted, using 3-{5-[3-(3-fluoro-phenyl)-5-methyl-isoxazol-4-yl]-imidazol-1-yl}-benzoic acid (100 mg, 0.28 mmol) instead of 4-[4-(5-methyl-3-phenyl-isoxazol-4-yl)-imidazol-1-yl]-benzoic acid, to the title compound (56 mg, 48%) which was obtained as an off-white solid. MS: m/e=417.0 [M+H]$^+$.

EXAMPLE 109

N-Cyclopropyl-3-{4-[3-(3-fluoro-phenyl)-5-methyl-isoxazol-4-yl]-imidazol-1-yl}-benzamide As described for Example 71c, cyclopropylamine was converted, using 3-{4-[3-(3-fluoro-phenyl)-5-methyl-isoxazol-4-yl]-imidazol-1-yl}-benzoic acid (100 mg, 0.28 mmol) instead of 4-[4-(5-methyl-3-phenyl-isoxazol-4-yl)-imidazol-1-yl]-benzoic acid, to the title compound (42 mg, 38%) which was obtained as an off-white solid. MS: m/e=403.0 [M+H]$^+$.

EXAMPLE 110

N-Cyclobutyl-3-{4-[3-(3-fluoro-phenyl)-5-methyl-isoxazol-4-yl]-imidazol-1-yl}-benzamide As described for Example 71c, cyclobutylamine was converted, using 3-{4-[3-(3-fluoro-phenyl)-5-methyl-isoxazol-4-yl]-imidazol-1-yl}-benzoic acid (100 mg, 0.28 mmol) instead of 4-[4-(5-methyl-3-phenyl-isoxazol-4-yl)-imidazol-1-yl]-benzoic acid, to the title compound (44 mg, 38%) which was obtained as an off-white solid. MS: m/e=417.0 [M+H]$^+$.

EXAMPLE 111

N-Cyclopentyl-3-{4-[3-(3-fluoro-phenyl)-5-methyl-isoxazol-4-yl]-imidazol-1-yl}-benzamide As described for Example 71c, cyclopentylamine was converted, using 3-{4-[3-(3-fluoro-phenyl)-5-methyl-isoxazol-4-yl]-imidazol-1-yl}-benzoic acid (100 mg, 0.28 mmol) instead of 4-[4-(5-methyl-3-phenyl-isoxazol-4-yl)-imidazol-1-yl]-benzoic acid, to the title compound (70 mg, 59%) which was obtained as an off-white solid. MS: m/e=431.0 [M+H]$^+$.

EXAMPLE 112

3-{4-[3-(3-Fluoro-phenyl)-5-methyl-isoxazol-4-yl]-imidazol-1-yl}-N-(tetrahydro-pyran-4-yl)-benzamide As described for Example 71c, tetrahydro-pyran-4-ylamine was converted, using 3-{4-[3-(3-fluoro-phenyl)-5-methyl-isoxazol-4-yl]-imidazol-1-yl}-benzoic acid (100 mg, 0.28 mmol) instead of 4-[4-(5-methyl-3-phenyl-isoxazol-4-yl)-imidazol-1-yl]-benzoic acid, to the title compound (56 mg, 49%) which was obtained as an off-white solid. MS: m/e=447.0 [M+H]$^+$.

EXAMPLE 113

4-{4-[3-(3-Fluoro-phenyl)-5-methyl-isoxazol-4-yl]-imidazol-1-yl}-N-pyridin-3-ylmethyl-benzamide As described for Example 71c, pyridine-3-ylamine was converted, using 4-{4-[3-(3-fluoro-phenyl)-5-methyl-isoxazol-4-yl]-imidazol-1-yl}-benzoic acid (100 mg, 0.28 mmol) instead of 4-[4-(5-methyl-3-phenyl-isoxazol-4-yl)-imidazol-1-yl]-benzoic acid, to the title compound (16 mg, 12%) which was obtained as an off-white solid. MS: m/e=453.9 [M+H]$^+$.

EXAMPLE 114

3-(4-Fluoro-phenyl)-4-[1-(4-fluoro-phenyl)-1H-imidazol-4-yl]-5-methyl-isoxazole

As described for Example 3, 4-(1H-imidazol-4-yl)-5-methyl-3-(4-fluorophenyl)-isoxazole (73 mg, 0.3 mmol) was converted, using 4-fluorophenylboronic acid instead of 4-fluorophenylboronic acid, to the title compound (10 mg, 10%) which was obtained as an off-white solid. MS: m/e=338.7[M+H]$^+$.

EXAMPLE 115

4-[1-(4-Bromo-phenyl)-1H-imidazol-4-yl]-3-(4-fluoro-phenyl)-5-methyl-isoxazole

As described for Example 3, 4-(1H-imidazol-4-yl)-5-methyl-3-(4-fluorophenyl)-isoxazole (73 mg, 0.3 mmol) was converted, using 4-bromophenylboronic acid instead of 4-fluorophenylboronic acid, to the title compound (15 mg, 13%) which was obtained as an off-white solid. MS: m/e=399.6[M+H]$^+$.

EXAMPLE 116

4-{4-[3-(4-Fluoro-phenyl)-5-methyl-isoxazol-4-yl]-imidazol-1-yl}-benzonitrile

As described for Example 3, 4-(1H-imidazol-4-yl)-5-methyl-3-(4-fluorophenyl)-isoxazole (73 mg, 0.3 mmol) was converted, using 4-cyanophenylboronic acid instead of 4-fluorophenylboronic acid, to the title compound (13 mg, 13%) which was obtained as an off-white solid. MS: m/e=345.3[M+H]$^+$.

EXAMPLE 117

4-{4-[3-(4-Fluoro-phenyl)-5-methyl-isoxazol-4-yl]-imidazol-1-yl}-pyridine

As described for Example 3, 4-(1H-imidazol-4-yl)-5-methyl-3-(4-fluorophenyl)-isoxazole (73 mg, 0.3 mmol) was converted, using 4-pyridylboronicboronic acid instead of 4-fluorophenylboronic acid, to the title compound (18 mg, 19%) which was obtained as an off-white solid. MS: m/e=321.5[M+H]$^+$.

EXAMPLE 118

3-(4-Fluoro-phenyl)-5-methyl-4-(1-m-tolyl-1H-imidazol-4-yl)-isoxazole

As described for Example 3, 4-(1H-imidazol-4-yl)-5-methyl-3-(4-fluorophenyl)-isoxazole (73 mg, 0.3 mmol) was converted, using m-tolylboronic acid instead of 4-fluorophenylboronic acid, to the title compound (17 mg, 17%) which was obtained as an off-white solid. MS: m/e=334.3 [M+H]+.

EXAMPLE 119

3-(4-Fluoro-phenyl)-4-[1-(3-fluoro-phenyl)-1H-imidazol-4-yl]-5-methyl-isoxazole

As described for Example 3, 4-(1H-imidazol-4-yl)-5-methyl-3-(4-fluorophenyl)-isoxazole (73 mg, 0.3 mmol) was converted, using 3-fluorophenylboronic acid instead of 4-fluorophenylboronic acid, to the title compound (13 mg, 12%) which was obtained as an off-white solid. MS: m/e=338.3 [M+H]+.

EXAMPLE 120

4-[1-(3-Chloro-phenyl)-1H-imidazol-4-yl]-3-(4-fluoro-phenyl)-5-methyl-isoxazole

As described for Example 3, 4-(1H-imidazol-4-yl)-5-methyl-3-(4-fluorophenyl)-isoxazole (73 mg, 0.3 mmol) was converted, using 3-chlorophenylboronic acid instead of 4-fluorophenylboronic acid, to the title compound (5 mg, 4%) which was obtained as an off-white solid. MS: m/e=354.6 [M+H]+.

EXAMPLE 121

4-[1-(3-Bromo-phenyl)-1H-imidazol-4-yl]-3-(4-fluoro-phenyl)-5-methyl-isoxazole

As described for Example 3, 4-(1H-imidazol-4-yl)-5-methyl-3-(4-fluorophenyl)-isoxazole (73 mg, 0.3 mmol) was converted, using 3-bromophenylboronic acid instead of 4-fluorophenylboronic acid, to the title compound (14 mg, 12%) which was obtained as an off-white solid. MS: m/e=399.4 [M+H]+.

EXAMPLE 122

3-{4-[3-(4-Fluoro-phenyl)-5-methyl-isoxazol-4-yl]-imidazol-1-yl}-benzonitrile

As described for Example 3, 4-(1H-imidazol-4-yl)-5-methyl-3-(4-fluorophenyl)-isoxazole (73 mg, 0.3 mmol) was converted, using 3-cyanophenylboronic acid instead of 4-fluorophenylboronic acid, to the title compound (13 mg, 13%) which was obtained as an off-white solid. MS: m/e=345.6 [M+H]+.

EXAMPLE 123

3-(4-Fluoro-phenyl)-5-methyl-4-[1-(3-trifluoromethyl-phenyl)-1H-imidazol-4-yl]-isoxazole As described for Example 3, 4-(1H-imidazol-4-yl)-5-methyl-3-(4-fluoro-phenyl)-isoxazole (72.9 mg, 0.3 mmol) was converted, using 3-trifluoromethylphenylboronic acid instead of 4-fluorophenylboronic acid, to the title compound (13 mg, 11%) which was obtained as an off-white solid. MS: m/e=388.6 [M+H]+.

EXAMPLE 124

3-{4-[3-(4-Fluoro-phenyl)-5-methyl-isoxazol-4-yl]-imidazol-1-yl}-pyridine

As described for Example 3, 4-(1H-imidazol-4-yl)-5-methyl-3-(4-fluorophenyl)-isoxazole (73 mg, 0.3 mmol) was converted, using 3-pyridylboronic acid instead of 4-fluorophenylboronic acid, to the title compound (18 mg, 19%) which was obtained as an off-white solid. MS: m/e=321.4 [M+H]+.

EXAMPLE 125

4-{4-[3-(4-Fluoro-phenyl)-5-methyl-isoxazol-4-yl]-imidazol-1-yl}-benzoic acid methyl ester As described for Example 1, 3,4-(1H-imidazol-4-yl)-5-methyl-3-(4-fluorophenyl)-isoxazole (100 mg, 0.41 mmol) was converted, using 4-fluorobenzoic acid methyl ester (1.54 g, 10.0 mmol) instead of 4-fluoroacetophenone, to the title compound (56 mg, 36%) which was obtained as a light yellow solid. MS: m/e=377.9 [M+H]+.

EXAMPLE 126

N-Cyclopentyl-4-{4-[3-(4-fluoro-phenyl)-5-methyl-isoxazol-4-yl]-imidazol-1-yl}-benzamide a) 4-{4-[3-(4-Fluoro-phenyl)-5-methyl-isoxazol-4-yl]-imidazol-1-yl}-benzoic acid As described for Example 71b, 4-{4-[3-(4-fluoro-phenyl)-5-methyl-isoxazol-4-yl]-imidazol-1-yl}-benzoic acid methyl ester (70 mg, 0.2 mmol) was converted to the title compound (56 mg, 84%) which was obtained as a yellow solid. MS m/e=363.1 [M+H]+.

b) N-Cyclopentyl-4-{4-[3-(4-fluoro-phenyl)-5-methyl-isoxazol-4-yl]-imidazol-1-yl}-benzamide As described for Example 71c, cyclopentylamine was converted, using 4-{4-[3-(4-fluoro-phenyl)-5-methyl-isoxazol-4-yl]-imidazol-1-yl}-benzoic acid (56 mg, 0.17 mmol) instead of 4-[4-(5-methyl-3-phenyl-isoxazol-4-yl)-imidazol-1-yl]-benzoic acid, to the title compound (54 mg, 76%) which was obtained as an off-white solid. MS: m/e=430.1 [M+H]+.

EXAMPLE 127

3-(4-Fluoro-phenyl)-5-methyl-4-[1-(2-trifluoromethyl-phenyl)-1H-imidazol-4-yl]-isoxazole As described for Example 3, 4-(1H-imidazol-4-yl)-5-methyl-3-(4-fluoro-phenyl)-isoxazole (73 mg, 0.3 mmol) was converted, using 2-trifluoromethylphenylboronic instead of 4-fluorophenylboronic acid, to the title compound (19 mg, 16%) which was obtained as an off-white solid. MS: m/e=388.4 [M+H]+.

EXAMPLE 128

4-[1-(3,4-Difluoro-phenyl)-1H-imidazol-4-yl]-3-(4-fluoro-phenyl)-5-methyl-isoxazole As described for Example 3, 4-(1H-imidazol-4-yl)-5-methyl-3-(4-fluoro-phenyl)-isoxazole (73 mg, 0.3 mmol) was converted, using 3,4-difluorophenylboronic acid instead of 4-fluorophenylboronic acid, to the title compound (16 mg, 15%) which was obtained as an off-white solid. MS: m/e=356.4 [M+H]+.

EXAMPLE 129

4-[1-(3,5-Difluoro-phenyl)-1H-imidazol-4-yl]-3-(4-fluoro-phenyl)-5-methyl-isoxazole As described for Example 3, 4-(1H-imidazol-4-yl)-5-methyl-3-(fluoro-phenyl)-isoxazole (72.9 mg, 0.3 mmol) was converted, using 3,5-diflurophenylboronic acid instead of 4-fluorophenylboronic acid, to the title compound (14 mg, 13%) which was obtained as an off-white solid. MS: m/e=356.2 [M+H]$^+$.

EXAMPLE 130

4-[1-(3,5-Dichloro-phenyl)-1H-imidazol-4-yl]-3-(4-fluoro-phenyl)-5-methyl-isoxazole As described for Example 3, 4-(1H-imidazol-4-yl)-5-methyl-3-phenyl-isoxazole (73 mg, 0.3 mmol) was converted, using 3,5-dichlorophenylboronic acid instead of 4-fluorophenylboronic acid, to the title compound (16 mg, 14%) which was obtained as an off-white solid. MS: m/e=389.3 [M+H]$^+$.

EXAMPLE 131

3-(4-Fluoro-phenyl)-5-methyl-4-[1-(4-methyl-3-nitro-phenyl)-1H-imidazol-4-yl]-isoxazole As described for Example 3, 4-(1H-imidazol-4-yl)-5-methyl-3-phenyl-isoxazole (73 mg, 0.3 mmol) was converted, using 4-methyl-5-nitro-phenylboronic acid instead of 4-fluorophenylboronic acid, to the title compound (14 mg, 12%) which was obtained as an off-white solid. MS: m/e=379.2 [M+H]$^+$.

EXAMPLE 132

1-{4-(4-[5-Ethyl-3-(4-fluoro-phenyl)-isoxazol-4-yl]-imidazol-1-yl}-phenyl)-ethanone As described for 1f, 4-fluoroacetonphenone was converted, using 5-ethyl-3-(4-fluoro-phenyl)-4-(1H-imidazole-4-yl)-isoxazole (100 mg, 0.39 mmol) instead of 4-(1H-imidazol-4-yl)-3-phenyl-isoxazole was converted to the title compound (63 mg, 43%) which was obtained as an off-white solid. MS: m/e=362.1 [M+H]$^+$.

EXAMPLE 133

5-Ethyl-3-(4-fluoro-phenyl)-4-[1-(4-trifluoromethyl-phenyl)-1H-imidazol-4-yl]-isoxazole As described for 1f, 1-fluoro-4-trifluoromethyl-benzene was converted, using 5-ethyl-3-(4-fluoro-phenyl)-4-(1H-imidazole-4-yl)-isoxazole (100 mg, 0.39 mmol) instead of 4-(1H-imidazol-4-yl)-3-phenyl-isoxazole was converted to the title compound (52 mg, 33%) which was obtained as an off-white solid. MS: m/e=402.1 [M+H]$^+$.

EXAMPLE 134

5-Ethyl-3-(4-fluoro-phenyl)-4-[1-(4-nitro-phenyl)-1H-imidazol-4-yl]-isoxazole As described for 1f, 1-fluoro-4-nitro-benzene was converted, using 5-ethyl-3-(4-fluoro-phenyl)-4-(1H-imidazole-4-yl)-isoxazole (100 mg, 0.39 mmol) instead of 4-(1H-imidazol-4-yl)-3-phenyl-isoxazole was converted to the title compound (43 mg, 28%) which was obtained as an off-white solid. MS: m/e=379.1.1 [M+H]$^+$.

EXAMPLE 135

1-{4-[4-(5-Cyclopropyl-3-phenyl-isoxazol-4-yl)-imidazol-1-yl]-phenyl}-ethanone a) 5-Cyclopropyl-3-phenyl-isoxazole-4-carboxylic acid ethyl ester To a solution of N-hydroxybenzenecarboximidoyl chloride (*Tetrahedron Letters*, 2006, 47, 1457, 2006; 500 mg, 3.21 mmol) and cyclopropyl-propynoic acid ethyl ester (*Organic Syntheses*, 1988, 66, 173; 515 mg, 3.21 mmol) in diethyl ether (5 mL) was added dropwise over a period of 2 min at ambient temperature triethylamine (0.54 ml, 3.86 mmol) and the reaction mixture was stirred for 3 d at this temperature. The resulting suspension was diluted with tert-butylmethylether (5 mL) and water (10 mL). The aqueous layer was extracted with tert-butylmethylether (10 mL) and the organic layers were washed with water (10 mL) and brine (10 mL). Drying over sodium sulfate and purification by chromatography (SiO$_2$, heptane:ethyl acetate=98:2 to 80:20) afforded the title compound (414 mg, 50%) as a colorless liquid. MS: m/e=258.1[M+H]$^+$.

b) 5-Cyclopropyl-3-phenyl-isoxazole-4-carboxylic acid

To a solution of 5-cyclopropyl-3-phenyl-isoxazole-4-carboxylic acid ethyl ester (408 mg, 1.58 mmol) in ethanol (4 mL) was added aqueous sodium hydroxide (1 N, 3.17 mL, 3.17 mmol) and the mixture was stirred for 3 h at 80° C. The ethanol was distilled off and the residue diluted with water (5 mL) and acified with aqueous HCl (1N) to pH=1. The resulting suspension was filtered off and washed with water affording the title compound (314 mg, 86%) as a white solid. MS: m/e=230.3[M+H]$^+$.

c) 5-Cyclopropyl-3-phenyl-isoxazole-4-carboxylic acid methoxy-methyl-amide

A mixture of 5-cyclopropyl-3-phenyl-isoxazole-4-carboxylic acid (3.72 g, 16 mmol), N,O-dimethylhydroxylamine hydrochloride (2.53 g, 26 mmol), N-methylmorpholine (2.85 mL, 26 mmol) and 4-dimethylaminopyridine (198 mg, 2 mmol) in dichloromethane (50 mL) and DMF (10 mL) was cooled to 0° C. Then 1-(3-dimethylaminopropyl)-3-ethylcarbodiimide (3.73 g, 19 mmol) was added and the reaction mixture was stirred at room temperature for 2 h. The reaction mixture was poured into hydrochloric acid (1 N) and extracted with ethyl acetate. The combined organic layers were then washed with a saturated solution of sodium hydrogen carbonate, brine and then dried over sodium sulphate and evaporated to leave a light yellow oil. Purification by chromatography (SiO$_2$, heptane:ethyl acetate=100:0 to 50:50) afforded the title compound (4.03 g, 91%) which was obtained as a colourles oil. MS: m/e=273.0 [M+H]$^+$.

d) 1-(5-Cylopropyl-3-phenyl-isoxazol-4-yl)-ethanone

To a solution of 5-cyclopropyl-3-phenyl-isoxazole-4-carboxylic acid methoxy-methyl-amide (4.00 g, 14.7 mmol) in THF (42 mL) cooled to −78° C. was added a solution of methylmagnesium bromide (3 M in diethylether, 9.80 mL, 29.4 mmol) dropwise within 5 min at −78° C. The cooling bath was removed and the reaction mixture was allowed to warm up to room temperature over 2.5 h. The reaction mixture was then re-cooled to −78° C., diluted with a saturated ammonium chloride solution (50 mL), allowed to warm up to room temperature and then diluted with water and extracted with ethyl acetate. The combined organic layers were then washed with brine and then dried over sodium sulphate and evaporated to afford the title compound (3.2 g, 94%) which was obtained as a light yellow solid. MS: m/e=228.3 [M+H]$^+$.

e) 2-Bromo-1-(5-cyclopropyl-3-phenyl-isoxazol-4-yl)-ethanone

To a solution of 1-(5-cyclopropyl-3-phenyl-isoxazol-4-yl)-ethanone (3.34 g, 14.6 mmol) in carbontetrachloride (9.7 mL) and AcOH (0.4 mL) at 48° C. was added a solution of bromine (0.79 mL, 14.6 mmol) in carbontetrachloride (7.8 mL) over 10 min keeping the temperature below 50° C. After addition the reaction mixture was allowed to cool down to room temperature and poured into ice-water (50 mL). The layers were separated and the aqueous layer extracted with dichloromethane. The combined organic layers were then washed with water and brine, dried over sodium sulphate and evaporated. Purification by chromatography (SiO$_2$, heptane:ethyl acetate: 100:0 to 80:20) afforded the title compound (4.29 g, 95%) which was obtained as an off-white solid. MS m/e (EI): 305.0/307.0 [M].

f) 5-Cyclopropyl-4-(1H-imidazol-4-yl)-3-phenyl-isoxazole

As described for Example 1e, 2-bromo-1-(5-cyclopropyl-3-phenyl-isoxazol-4-yl)-ethanone (2.0 g, 7 mmol) instead of 2-bromo-1-(3-phenyl-isoxazol-4-yl)-ethanone was converted to the title compound (0.7 g, 43%) which was obtained as a light brown solid. MS: m/e=252.1 [M+H]$^+$.

g) 1-{4-[4-(5-Cyclopropyl-3-phenyl-isoxazol-4-yl)-imidazol-1-yl]-phenyl}-ethanone As described for Example 1f, 5-cyclopropyl-4-(1H-imidazol-4-yl)-3-phenyl-isoxazole (75 mg, 0.3 mmol) instead of 4-(1H-imidazol-4-yl)-3-phenyl-isoxazole was converted to the title compound (64 mg, 58%) which was obtained as a yellow gum. MS: m/e=370.0 [M+H]$^+$.

EXAMPLE 136

5-Cyclopropyl-4-[1-(4-nitro-phenyl)-1H-imidazol-4-yl]-3-phenyl-isoxazole

As described for Example 13, 5-cyclopropyl-4-(1H-imidazol-4-yl)-3-phenyl-isoxazole (75 mg, 0.3 mmol) instead of 4-(1H-imidazol-4-yl)-5-methyl-3-phenyl-isoxazole was converted to the title compound (89 mg, 80%) which was obtained as a yellow solid. MS: m/e=373.1 [M+H]$^+$.

EXAMPLE 137

[3-Phenyl-4-(1-phenyl-1H-imidazol-4-yl)-isoxazol-5-yl]-methanol a) 5-Methoxymethyl-3-phenyl-isoxazole-4-carboxylic acid methyl ester As described for Example 36c, (E)- and/or (Z)-N-hydroxybenzenecarboximidoyl chloride (14.04 g, 90 mmol) was converted, using 4-methoxy-3-oxo-butyric acid methyl ester instead of acteylacetone to the crude title compound (18.76 g) which was obtained as an off-white solid and used directly in the next step without further purification.

b) 5-Methoxymethyl-3-phenyl-isoxazole-4-carboxylic acid

As described for Example 71b, 5-methoxymethyl-3-phenyl-isoxazole-4-carboxylic acid methyl ester (18.7 g, 76 mmol) was converted to the title compound (12.87 g, 73% over two steps) which was obtained as a light yellow solid. MS: m/e=232.0[M+H]$^+$.

c) 5-Methoxymethyl-3-phenyl-isoxazole-4-carboxylic acid chloride

A suspension of 5-methoxymethyl-3-phenyl-isoxazole-4-carboxylic acid (10.0 g, 43.0 mmol) in thionyl chloride (20 mL) was heated at 60° C. for 3 h. The resulting mixture was concentrated under reduced pressure to afford the crude title compound (11.16 g, 100%) which was obtained as a light yellow liquid. The crude product was directly used in the next step without further purification.

d) 2-Bromo-1-(5-methoxymethyl-3-phenyl-isoxazol-4-yl)ethanone

To a solution of 5-methoxymethyl-3-phenyl-isoxazole-4-carboxylic acid chloride (11.16 g, 44 mmol) in dry ether (350 mL) was added diazomethane solution in ether (0.1 N, 100 mL) at iced-bath cooling temperature. The reaction was stirred for 2 h at 0° C. Aqueous solution of hydrobromic acid (>40 wt %, 100 mL) was then added dropwise to the reaction solution at iced-bath cooling temperature. After complete addition, the organic layer was separated, and the aqueous phase was extracted with ether. The combined ether solution was washed with water and brine, dried over magnesium sulphate and evaporated to afford the title compound (12.83 g, 94%) which was obtained as a light yellow liquid. MS: m/e=310.0/311.9 [M+H]$^+$.

e) 3-phenyl-4-(1H-imidazol-4-yl)-5-methoxymethyl-isoxazole

A solution of 2-Bromo-1-(5-methoxymethyl-3-phenyl-isoxazol-4-yl)ethanone (12.8 g, 41 mmol) in formamide (30 mL) was heated under nitrogen atmosphere at 170° C. for 3 h. After the reaction mixture was cooled to room temperature, saturated sodium bicarbonate (200 mL) was added. The formed precipate was filtered, washed with ether, and dried to afford the title compound (7.27 g, 70%) which was obtained as a brown solid. MS: m/e=255.9 [M+H]$^+$.

f) 1-(4-{4-[3-phenyl-5-methoxymethyl-isoxazol-4-yl]-imidazol-1-yl}-phenyl)-ethanone As described for Example 3, 3-phenyl-4-(1H-imidazol-4-yl)-5-methoxymethyl-isoxazole (38.2 mg, 0.15 mmol) was converted, using phenylboronic acid instead of 4-fluorophenylboronic acid, through prepared HPLC to the title compound (30.0 mg, 61%) which was obtained as an off-white solid. MS: m/e=332.0 [M+H]$^+$.

g) [3-Phenyl-4-(1-phenyl-1H-imidazol-4-yl)-isoxazol-5-yl]-methanol

To a stirred solution of 1-(4-{4-[3-phenyl-5-methoxymethyl-isoxazol-4-yl]-imidazol-1-yl}-phenyl)-ethanone (147 mg, 0.44 mmol) in dry dichloromethane (4 mL) was added slowly boron tribromide (334 mg, 1.33 mmol) at dry ice-acetone bath cooling temperature. After complete addition, the resulting mixture was stirred at −78° C. for 15 min, and then allowed to warm up to room temperature for 35 min. The reaction was quenched with saturated sodium bicarbonate. The organic layer was separated, and the aqueous phase was extracted with dichloromethane and ethylacetate. The combined organic solution was dried over sodium sulphate and evaporated. Purification by preparative HPLC afforded the title compound (98 mg, 70%) which was obtained as an off-white solid. MS: m/e=318.0 [M+H]$^+$.

EXAMPLE 138

{3-Phenyl-4-[1-(4-trifluoromethyl-phenyl)-1H-imidazol-4-yl]-isoxazol-5-yl}-methanol a) 5-Methoxymethyl-3-phenyl-4-[1-(4-trifluoromethyl-phenyl)-1-H-imidazol-4-yl]isoxazole As described for Example 1f, 3-phenyl-4-(1H-imidazol-4-yl)-5-methoxymethyl-isoxazole (127.6 mg, 0.50 mmol) was converted, using 1-fluoro-4-trifluoromethyl-benzene instead of 1-(4-fluorophenyl)-ethanone, to the title compound (125 mg, 63%) which was obtained as an off-white solid. MS: m/e=400.1 [M+H]$^+$.

b) {3-Phenyl-4-[1-(4-trifluoromethyl-phenyl)-1H-imidazol-4-yl]-isoxazol-5-yl}-methanol As described for Example 137g, 5-methoxymethyl-3-phenyl-4-[1-(4-trifluoromethyl-phenyl)-1-H-inidazol-4-yl]isoxazole (200 mg, 0.5 mmol) was converted to the title compound (146 mg, 81%) which was obtained as an off-white solid. MS: m/e=386.3[M+H]$^+$.

EXAMPLE 139

4-[4-(5-Hydroxymethyl-3-phenyl-isoxazol-4-yl)-imidazol-1-yl]-benzonitrile a) 4-[4-(5-Methoxymethyl-3-phenyl-isoxazol-4-yl)-imidazol-1-yl]benzonitrile As described for Example 1f, 3-phenyl-4-(1H-imidazol-4-yl)-5-methoxymethyl-isoxazole (128 mg, 0.50 mmol) was converted, using 4-fluorobenzonitrile instead of 1-(4-fluorophenyl)-ethanone, to the title compound (75 mg, 42%) which was obtained as an off-white solid. MS: m/e=357.0 [M+H]$^+$.

b) 4-[4-(5-Hydroxymethyl-3-phenyl-isoxazol-4-yl)-imidazol-1-yl]-benzonitrile

As described for Example 137g, 1-(4-{4-[3-phenyl-5-methoxymethyl-isoxazol-4-yl]-imidazol-1-yl}-phenyl)-ethanone (178 mg, 0.5 mmol) was converted to the title compound (140 mg, 83%) which was obtained as an off-white solid. MS: m/e=343.4[M+H]$^+$.

EXAMPLE 140

1-(4-{4-[3-(4-Fluoro-phenyl)-5-hydroxymethyl-isoxazol-4-yl]-imidazol-1-yl}-phenyl)-ethanone To a stirred solution of 1-(4-{4-[3-(4-fluoro-phenyl)-5-methoxymethyl-isoxazol-4-yl]-imidazol-1-yl}-phenyl)-ethanone (239 mg, 0.61 mmol) in dry dichloromethane (4 mL) was added slowly boron tribromide (0.17 mL, 0.3 mmol) at dry ice-acetone bath cooling temperature. After complete addition, the resulting mixture was stirred at −78° C. for 15 min, and −15° C. for 35 min, and then allowed to warm up to room temperature for 20 min. The reaction was quenched with saturated sodium bicarbonate (30 mL). The organic layer was separated, and the aqueous phase was extracted with dichloromethane and ethylacetate. The combined organic extracts were then dried over sodium sulphate and evaporated. Purification by preparative HPLC afforded the title compound (35 mg, 15%) which was obtained as an off-white solid. MS: m/e=378.0 [M+H]$^+$.

EXAMPLE 141

{3-(4-Fluoro-phenyl)-4-[1-(4-trifluoromethyl-phenyl)-1H-imidazol-4-yl]-isoxazol-5-yl}-methanol As described for Example 140, 3-(4-fluoro-phenyl)-5-methoxymethyl-4-[1-(4-trifluoromethyl-phenyl)-1H-imidazol-4-yl]-isoxazole (417 mg, 1.13 mmol), instead of 1-(4-{4-[3-(4-fluoro-phenyl)-5-methoxymethyl-isoxazol-4-yl]-imidazol-1-yl}-phenyl)-ethanone, was converted to the title compound (460 mg, 95%) which was obtained as yellow solid. MS: m/e=403.9 [M+H]$^+$.

EXAMPLE 142

1-(4-{4-[3-(4-Fluoro-phenyl)-5-methoxymethyl-isoxazol-4-yl]-imidazol-1-yl}-phenyl)-ethanone a) 3-(4-Fluoro-phenyl)-5-methoxymethyl-isoxazole-4-carboxylic acid methyl ester As described for Example 36c, (E)- and/or (Z)-N-hydroxy-4-fluoro-benzenecarboximidoyl chloride (12.1 g, 70 mmol) was converted, using 4-methoxy-3-oxo-butyric acid methyl ester instead of acetylacetone to the title compound (13.8 g, 74%) which was obtained as a light yellow solid. MS: m/e=266.0 [M+H]$^+$.

b) 3-(4-Fluoro-phenyl)-5-methoxymethyl-isoxazole-4-carboxylic acid

As described for Example 71b, 3-(4-fluoro-phenyl)-5-methoxymethyl-isoxazole-4-carboxylic acid methyl ester (13.8 g, 52.3 mmol) was converted to the title compound (12.1 g, 92%) which was obtained as a light yellow solid. MS: m/e=252.0 [M+H]$^+$.

c) 3-(4-Fluoro-phenyl)-5-methoxymethyl-isoxazole-4-carboxylic acid chloride

To a suspension of 3-(4-fluoro-phenyl)-5-methoxymethyl-isoxazole-4-carboxylic acid (2.51 g, 10.0 mmol) in thionyl chloride (4.0 mL) was added two drops of DMF, and the resulting reaction mixture was heated at 60° C. for 3 h. After cooling to room temperature, the mixture was concentrated under reduced pressure to afford the crude title compound (2.7 g, 100%) which was obtained as a light yellow liquid and used directly in the next step without further purification.

d) 2-Bromo-1-[3-(4-fluoro-phenyl)-5-methoxymethyl-isoxazol-4-yl]ethanone

To a solution of 3-(4-fluoro-phenyl)-5-methoxyrnethyl-isoxazole-4-carboxylic acid chloride (2.7 g, 10.0 mmol) in methylene chloride (50 mL) was added diazomethane solution in ether (0.1 N, 100 mL) at ice-bath cooling temperature. The reaction was stirred for 1.5 h at 0° C. and allowed to stand overnight in a freezer at 0° C. An aqueous solution of hydrobromic acid (>40 wt %, 70 mL) was added dropwise to the reaction solution at ice-bath cooling temperature. After complete addition, the resulting mixture was stirred at 0° C. for 0.5 h and then allowed to warm up to room temperature and stirred for 1.5 h. The organic layer was separated, and the aqueous phase was extracted with ether. The combined ether solution was then washed with water and brine, dried over sodium sulphate and evaporated to afford the crude title compound (3.8 g) which was obtained as a light yellow liquid. MS: m/e=328.0/330.4 [M+H]$^+$.

e) 3-(4-Fluoro-phenyl)-4-(1H-imidazol-4-yl)-5-methoxymethyl-isoxazole

A solution of 2-bromo-1-[3-(4-fluoro-phenyl)-5-methoxymethyl-isoxazol-4-yl]ethanone (3.7 g) in formamide (20 mL) was heated under nitrogen atmosphere at 150° C. for 16 h. After the reaction mixture was cooled to room temperature, saturated sodium bicarbonate (40 mL) was added. The formed precipitate was filtered, washed with water, cold ethyl acetate, and dried to afford the title compound (1.82 g, 72% over steps d and e) which was obtained as a light yellow solid. MS: m/e=274.3[M+H]$^+$.

f) 1-(4-{4-[3-(4-Fluoro-phenyl)-5-methoxymethyl-isoxazol-4-yl]-imidazol-1-yl}-phenyl)-ethanone A mixture of 3-(4-fluoro-phenyl)-4-(1H-imidazol-4-yl)-5-methoxymethyl-isoxazole (273 mg, 1.0 mmol), 1-(4-fluorophenyl)-ethanone (212 mg, 1.5 mmol), and potassium carbonate (276 mg, 2.0 mmol) in DMF (4 mL) was stirred at 120° C. for 16 h. After cooling to room temperature, the resulting solution was poured into cold water and stirred for 15 min. The precipitate was collected by filtration, washed with water, hexane, and dried to afford the title compound (330 mg, 79%) which was obtained as light brown solid. MS: m/e=392.5[M+H]$^+$.

EXAMPLE 143

3-(4-Fluoro-phenyl)-5-methoxymethyl-4-[1-(4-trifluoromethyl-phenyl)-1H-imidazol-4-yl]-isoxazole As described for Example 142f, 3-(4-fluoro-phenyl)-4-(1H-imidazol-4-yl)-5-methoxymethyl-isoxazole (546 mg, 2.0 mmol) was converted, using 1-fluoro-4-trifluoromethyl-benzene instead of 1-(4-fluorophenyl)-ethanone, to the title compound (520 mg, 57%) which was obtained as light yellow solid. MS: m/e=418.4[M+H]$^+$.

EXAMPLE 144

4-(5-Methyl-3-phenyl-isoxazol-4-yl)-1-phenyl-1H-imidazole-2-carboxylic acid methyl ester a) 4-(5-Methyl-3-phenyl-isoxazol-4-yl)-1H-imidazole-2-carboxylic acid methyl ester To a solution of 4-(bromoacetyl)-5-methyl-3-phenylisoxazole (commercially available) (6.0 g, 210 mmol) in DMSO (40 mL) was added water (0.4 mL) and the resulting mixture stirred at room temperature overnight and then the mixture evaporated. Purification by chromatography (SiO$_2$, heptane: ethyl acetate=100:0 to 50:50) afforded a compound (3.79 g) which was obtained as a yellow foam. To a mixture of ammonium acetate (3.77 g, 16 mmol) in a water (4 mL) acetonitrile (40 mL) mixture at 0° C. was added 2-hydroxy-2-methoxy-acetic acid methyl ester (7.77 g, 65 mmol) in acetonitrile (100 mL) and to this resulting mixture was then added the yellow foam (3.77 g) over 2 min. The resulting mixture was then stirred at 0° C. for 1.5 h and then warmed up to room temperature over 30 min. The reaction mixture was then extracted with ethyl acetate. The combined organic layers were then washed with a saturated solution of sodium hydrogen carbonate, brine and then dried over sodium sulphate and evaporated to leave an orange solid. During extraction a precipitate formed and was removed by filtration followed by washing with water and then dissolved in ethyl acetate, dried over sodium sulphate and evaporated to leave a white solid. Purification by chromatography (SiO$_2$, heptane:ethyl acetate=100:0 to 80:20) afforded the title compound (2.67 g, 58%) which was obtained as a white solid. MS: m/e=284.0 [M+H]$^+$.

b) 4-(5-Methyl-3-phenyl-isoxazol-4-yl)-1-phenyl-1H-imidazole-2-carboxylic acid methyl ester As described for Example 3, 4-(5-methyl-3-phenyl-isoxazol-4-yl)-1H-imidazole-2-carboxylic acid methyl ester (100 mg, 0.44 mmol) instead of 4-(1H-imidazol-4-yl)-5-methyl-3-phenyl-isoxazole was converted, using phenylphenylboronic acid (86 mg, 0.71 mmol) instead of 4-fluorophenylboronic acid, to the title compound (815 mg, 12%) which was obtained as a white solid. MS: m/e=360.0 [M+H]$^+$.

EXAMPLE 145

4-(5-Methyl-3-phenyl-isoxazol-4-yl)-1-(4-trifluoromethyl-phenyl)-1H-imidazole-2-carboxylic acid ethyl ester To a solution of 5-methyl-3-phenyl-4-[1-(4-trifluoromethyl-phenyl)-1H-imidazol-4-yl]-isoxazole (950 mg, 2.6 mmol) in THF (50 mL) at −78° C. was added BuLi (1.6 M in hexane, 2.4 mL, 3.9 mmol) and the resulting mixture allowed to warm up to −25° C. over 20 min and then re-cooled to −78° C. Then ethyl chloroformate (474 mg, 4.4 mmol) was added and the resulting mixture allowed to warm up to −25° C. over 3 h and then warmed up to 0° C. whereupon water was added. The reaction mixture was then extracted with ethyl acetate and the combined organic layers were then washed with a saturated solution of sodium hydrogen carbonate, brine and then dried over sodium sulphate and evaporated. Purification by chromatography (SiO$_2$, heptane:ethyl acetate=100:0 to 80:20) afforded the title compound (232 mg, 18%) which was obtained as an off-white foam. MS: m/e=442.5 [M+H]$^+$.

EXAMPLE 146

4-(2-Benzyloxymethyl-1-phenyl-1H-imidazol-4-yl)-5-methyl-3-phenyl-isoxazole

As described for Example 144b, 4-(2-benzyloxymethyl-1H-imidazol-4-yl)-5-methyl-3-phenyl-isoxazole (100 mg, 0.29 mmol) instead of 4-(5-methyl-3-phenyl-isoxazol-4-yl)-1H-imidazole-2-carboxylic acid methyl ester was converted to the title compound (8.8 mg, 7%) which was obtained as a colourless gum. MS: m/e=422.3 [M+H]$^+$.

EXAMPLE 147

[4-(5-Methyl-3-phenyl-isoxazol-4-yl)-1-(4-nitro-phenyl)-1H-imidazol-2-yl]-methanol To a solution of 4-[2-benzyloxymethyl-1-(4-nitro-phenyl)-1H-imidazol-4-yl]-5-methyl-3-phenyl-isoxazole (200 mg, 0.43 mmol) in DCM (10 mL) at 0° C. was added trifluoroacetic acid (0.98 mL) and trifluoromethanesulfonic acid (0.06 mL) and the resulting mixture stirred vigorously for 3 h. The mixture was then poured onto a saturated solution of sodium hydrogen carbonate and stirred for 30 min. The resulting precipitate was then filtered off, washed with water and then dried to afford the title compound (91 mg, 56%) which was obtained as a white solid. MS: m/e=377.4 [M+H]$^+$.

EXAMPLE 148

4-[2-Chloromethyl-1-(4-nitro-phenyl)-1H-imidazol-4-yl]-5-methyl-3-phenyl-isoxazole To a solution of [4-(5-methyl-3-phenyl-isoxazol-4-yl)-1-(4-nitro-phenyl)-1H-imidazol-2-yl]-methanol (50 mg, 0.13 mmol) in DCM (5 mL) at 0° C. was added triethylamine (92.6 µL, 0.66 mmol) and methanesulfonyl chloride (30.97 µL, 0.40 mmol) and the resulting mixture allowed to warm up to room temperature over 3 h and then stirred for a subsequent 2 h. The mixture was then poured onto a saturated solution of sodium hydrogen carbonate and extracted with DCM. The combined organic layers were then dried over sodium sulphate and evaporated. Purification by chromatography (SiO$_2$, heptane:ethyl acetate=100:0 to 80:20) afforded the title compound (37 mg, 70%) which was obtained as a yellow foam. MS: m/e=395.0 [M+H]$^+$.

EXAMPLE 149

4-(5-Methyl-3-phenyl-isoxazol-4-yl)-1-(4-nitro-phenyl)-1H-imidazole-2-carbaldehyde To a solution of [4-(5-methyl-3-phenyl-isoxazol-4-yl)-1-(4-nitro-phenyl)-1H-imidazol-2-yl]-methanol (50 mg, 0.13 mmol) in DCM (3 mL) was added manganese(IV) oxide (46 mg, 0.5 mmol) and the resulting mixture stirred at room temperature for 5 h. The mixture was then filtered over dicalite and washed with DCM. Then another aliquot of manganese(IV) oxide (46 mg, 0.5 mmol) was added and the mixture stirred overnight and then another aliquot of manganese(IV) oxide (120 mg, 1.3 mmol) was added and the mixture stirred for 5 h. The mixture was then filtered over dicalite and washed with DCM and evaporated. Purification by chromatography (SiO$_2$, heptane:ethyl acetate=100:0 to 80:20) afforded the title compound (16.4 mg, 33%) which was obtained as a yellow gum. MS: m/e=375.3 [M+H]$^+$.

EXAMPLE 150

4-[2-Methoxymethyl-1-(4-nitro-phenyl)-1H-imidazol-4-yl]-5-methyl-3-phenyl-isoxazole To a solution of 4-[2-chloromethyl-1-(4-nitro-phenyl)-1H-imidazol-4-yl]-5-methyl-3-phenyl-isoxazole (50 mg, 0.13 mmol) in methanol (1 mL) was added a solution of sodium methoxide (5.4 M in MeOH, 23.5 μL, 0.13 mmol) and the resulting mixture stirred at room temperature overnight. The mixture was then poured onto water and extracted with ethyl acetate. The combined organic layers were then dried over sodium sulphate and evaporated. Purification by chromatography (SiO$_2$, heptane:ethyl acetate=100:0 to 80:20) afforded the title compound (27 mg, 55%) which was obtained as a yellow solid. MS: m/e=391.1 [M+H]$^+$.

EXAMPLE 151

4-[2-Ethoxymethyl-1-(4-nitro-phenyl)-1H-imidazol-4-yl]-5-methyl-3-phenyl-isoxazole As described for Example 150, 4-[2-chloromethyl-1-(4-nitro-phenyl)-1H-imidazol-4-yl]-5-methyl-3-phenyl-isoxazole (50 mg, 0.13 mmol), using sodium ethoxide in ethanol instead of sodium methoxide in methanol, was converted to the title compound (47 mg, 92%) which was obtained as a yellow solid. MS: m/e=405.5 [M+H]$^+$.

EXAMPLE 152

[4-(5-Methyl-3-phenyl-isoxazol-4-yl)-1-(4-nitrophenyl)-1H-imidazol-2-ylmethyl]-(3-morpholin-4-yl-propyl)-amine To a solution of 4-[2-chloromethyl-1-(4-nitro-phenyl)-1H-imidazol-4-yl]-5-methyl-3-phenyl-isoxazole (50 mg, 0.13 mmol) in DMF (2 mL) was added 4-(3-aminopropyl)morpholine (36.5 mg, 0.25 mmol) and KI (4.2 mg, 0.03 mmol) and the resulting mixture heated at 80° C. for 2 h. After cooling to room temperature, the mixture was then poured onto water and extracted with ethyl acetate. The combined organic layers were then washed with brine and water and then dried over sodium sulphate and evaporated. Purification by chromatography (SiO$_2$, dichloromethane:methanol=100:0 to 80:20) afforded the title compound (47 mg, 74%) which was obtained as a yellow gum. MS: m/e=503.4 [M+H]$^+$.

EXAMPLE 153

5-Methyl-4-[2-(4-methyl-benzyloxymethyl)-1-(4-nitro-phenyl)-1H-imidazol-4-yl]-3-phenyl-isoxazole A solution of 4-[2-chloromethyl-1-(4-nitro-phenyl)-1H-imidazol-4-yl]-5-methyl-3-phenyl-isoxazole (50 mg, 0.13 mmol) in DMF (0.5 mL) was added to a suspension on NaH (55% in oil, 5.5 mg, 0.13 mmol) in DMF (0.5 mL) containing 4-methylbenzyl alcohol (15.5 mg, 0.13 mmol) in DMF (0.5 mL) and the resulting mixture stirred at room temperature for 2 h. The mixture was then poured onto water and extracted with ethyl acetate. The combined organic layers were then washed with brine and water and then dried over sodium sulphate and evaporated. Purification by chromatography (SiO$_2$, heptane:ethyl acetate=100:0 to 80:20) afforded the title compound (11.6 mg, 19%) which was obtained as a yellow gum. MS: m/e=481.3 [M+H]$^+$.

EXAMPLE 154

4-[2-(4-Fluoro-benzyloxymethyl)-1-(4-nitro-phenyl)-1H-imidazol-4-yl]-5-methyl-3-phenyl-isoxazole As described for Example 153, 4-[2-chloromethyl-1-(4-nitro-phenyl)-1H-imidazol-4-yl]-5-methyl-3-phenyl-isoxazole (50 mg, 0.13 mmol), using 4-fluorobenzyl alcohol instead of 4-methylbenzyl alcohol, was converted to the title compound (22 mg, 36%) which was obtained as a yellow gum. MS: m/e=485.5 [M+H]$^+$.

EXAMPLE 155

4-[2-(4-Chloro-benzyloxymethyl)-1-(4-nitro-phenyl)-1H-imidazol-4-yl]-5-methyl-3-phenyl-isoxazole As described for Example 153, 4-[2-chloromethyl-1-(4-nitro-phenyl)-1H-imidazol-4-yl]-5-methyl-3-phenyl-isoxazole (100 mg, 0.25 mmol), using 4-chlorobenzyl alcohol instead of 4-methylbenzyl alcohol, was converted to the title compound (28 mg, 22%) which was obtained as a light yellow solid. MS: m/e=501.3 [M+H]$^+$.

EXAMPLE 156

4-[2-(4-Bromo-benzyloxymethyl)-1-(4-nitro-phenyl)-1H-imidazol-4-yl]-5-methyl-3-phenyl-isoxazole As described for Example 153, 4-[2-chloromethyl-1-(4-nitro-phenyl)-1H-imidazol-4-yl]-5-methyl-3-phenyl-isoxazole (100 mg, 0.25 mmol), using 4-bromobenzyl alcohol instead of 4-methylbenzyl alcohol, was converted to the title compound (21 mg, 15%) which was obtained as a light yellow solid. MS: m/e=545.3/547.3 [M+H]$^+$.

EXAMPLE 157

4-[2-(3-Chloro-benzyloxymethyl)-1-(4-nitro-phenyl)-1H-imidazol-4-yl]-5-methyl-3-phenyl-isoxazole As described for Example 153, 4-[2-chloromethyl-1-(4-nitro-phenyl)-1H-imidazol-4-yl]-5-methyl-3-phenyl-isoxazole (100 mg, 0.25 mmol), using 3-chlorobenzyl alcohol and KI (8.4 mg, 0.05 mmol) instead of 4-methylbenzyl alcohol, was converted to the title compound (76 mg, 60%) which was obtained as a light yellow solid. MS: m/e=501.4 [M+H]$^+$.

EXAMPLE 158

4-[2-(3-Fluoro-benzyloxymethyl)-1-(4-nitro-phenyl)-1H-imidazol-4-yl]-5-methyl-3-phenyl-isoxazole As described for Example 157, 4-[2-chloromethyl-1-(4-nitro-phenyl)-1H-imidazol-4-yl]-5-methyl-3-phenyl-isoxazole (100 mg, 0.25 mmol), using 3-fluorobenzyl alcohol instead of 3-chlorobenzyl alcohol, was converted to the title

EXAMPLE 159

4-[2-(3-Bromo-benzyloxymethyl)-1-(4-nitro-phenyl)-1H-imidazol-4-yl]-5-methyl-3-phenyl-isoxazole As described for Example 157, 4-[2-chloromethyl-1-(4-nitro-phenyl)-1H-imidazol-4-yl]-5-methyl-3-phenyl-isoxazole (100 mg, 0.25 mmol), using 3-bromobenzyl alcohol instead of 3-chlorobenzyl alcohol, was converted to the title compound (84 mg, 61%) which was obtained as a light yellow gum. MS: m/e=545.3/547.3 [M+H]$^+$.

EXAMPLE 160

4-[2-(2-Fluoro-benzyloxymethyl)-1-(4-nitro-phenyl)-1H-imidazol-4-yl]-5-methyl-3-phenyl-isoxazole As described for Example 157, 4-[2-chloromethyl-1-(4-nitro-phenyl)-1H-imidazol-4-yl]-5-methyl-3-phenyl-isoxazole (100 mg, 0.25 mmol), using 2-fluorobenzyl alcohol instead of 3-chlorobenzyl alcohol, was converted to the title compound (75 mg, 61%) which was obtained as a light yellow foam. MS: m/e=485.5 [M+H]$^+$.

EXAMPLE 161

2-[4-(5-Methyl-3-phenyl-isoxazol-4-yl)-1-(4-nitro-phenyl)-1H-imidazol-2-ylmethoxymethyl]-pyridine As described for Example 157, 4-[2-chloromethyl-1-(4-nitro-phenyl)-1H-imidazol-4-yl]-5-methyl-3-phenyl-isoxazole (100 mg, 0.25 mmol), using 2-(hydroxymethyl)pyridine instead of 3-chlorobenzyl alcohol, was converted to the title compound (75 mg, 56%) which was obtained as a light yellow foam. MS: m/e=468.5 [M+H]$^+$.

EXAMPLE 162

2-Methyl-6-[4-(5-methyl-3-phenyl-isoxazol-4-yl)-1-(4-nitro-phenyl)-1H-imidazol-2-ylmethoxymethyl]-pyridine As described for Example 157, 4-[2-chloromethyl-1-(4-nitro-phenyl)-1H-imidazol-4-yl]-5-methyl-3-phenyl-isoxazole (100 mg, 0.25 mmol), using 6-methyl-2-pyridinemethanol instead of 3-chlorobenzyl alcohol, was converted to the title compound (72 mg, 53%) which was obtained as a light yellow foam. MS: m/e=482.5 [M+H]$^+$.

EXAMPLE 163

3-[4-(5-Methyl-3-phenyl-isoxazol-4-yl)-1-(4-nitro-phenyl)-1H-imidazol-2-ylmethoxymethyl]-pyridine As described for Example 157, 4-[2-chloromethyl-1-(4-nitro-phenyl)-1H-imidazol-4-yl]-5-methyl-3-phenyl-isoxazole (100 mg, 0.25 mmol), using 3-(hydroxymethyl)pyridine instead of 3-chlorobenzyl alcohol, was converted to the title compound (89 mg, 75%) which was obtained as a light yellow solid. MS: m/e=468.0 [M+H]$^+$.

The compound (70 mg, 57%) which was obtained as a light yellow solid. MS: m/e=485.5 [M+H]$^+$.

EXAMPLE 164

5-[4-(5-Methyl-3-phenyl-isoxazol-4-yl)-1-(4-nitro-phenyl)-1H-imidazol-2-ylmethoxymethyl]-2-trifluoromethyl-pyridine As described for Example 157, 4-[2-chloromethyl-1-(4-nitro-phenyl)-1H-imidazol-4-yl]-5-methyl-3-phenyl-isoxazole (100 mg, 0.25 mmol), using 6-(trifluoromethyl)pyridine-3-methanol instead of 3-chlorobenzyl alcohol, was converted to the title compound (72 mg, 53%) which was obtained as a light yellow solid. MS: m/e=536.5 [M+H]$^+$.

EXAMPLE 165

4-[4-(5-Methyl-3-phenyl-isoxazol-4-yl)-1-(4-nitro-phenyl)-1H-imidazol-2-ylmethoxymethyl]-pyridine As described for Example 157, 4-[2-chloromethyl-1-(4-nitro-phenyl)-1H-imidazol-4-yl]-5-methyl-3-phenyl-isoxazole (100 mg, 0.25 mmol), using 4-(hydroxymethyl)pyridine instead of 3-chlorobenzyl alcohol, was converted to the title compound (43 mg, 36%) which was obtained as a light brown solid. MS: m/e=468.1 [M+H]$^+$.

The invention claimed is:

1. An aryl-isoxazol-4-yl-imidazole derivative of formula I:

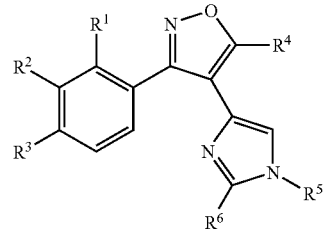

wherein $R^1$, $R^2$, and $R^3$ are each independently hydrogen or halogen;

$R^4$ is hydrogen, lower alkyl, cycloalkyl, —(CH$_2$)$_n$—O—lower alkyl or lower alkyl substituted by hydroxy;

$R^5$ is —(CH$_2$)$_m$-aryl or —(CH$_2$)$_m$-heteroaryl, each of which is optionally substituted by one or more substituents selected from the group consisting of halogen, cyano, nitro, lower alkyl, lower alkoxy, lower alkylsulfanyl, lower alkyl substituted by halogen, —C(O)-lower alkyl, —C(O)—O-lower alkyl, —NH—C(O)—O-lower alkyl and —C(O)—NH—R', wherein R' is lower alkynyl or is lower alkyl substituted by halogen, or is —(CH$_2$)$_n$-cycloalkyl, —(CH$_2$)$_n$-heterocyclyl, —(CH$_2$)$_n$-heteroaryl or —(CH$_2$)$_n$-aryl, each of which is optionally substituted by halogen;

$R^6$ is hydrogen,

—C(O)H,

—(CH$_2$)$_n$—O-lower alkyl,

—C(O)O-lower alkyl, lower alkyl substituted by hydroxy or halogen, cycloalkyl, aryl, —(CH$_2$)$_n$—O—CH$_2$-aryl, optionally substituted by halogen or lower alkyl, —(CH$_2$)$_n$—O—CH$_2$-heteroaryl, optionally substituted by halogen, lower alkyl or lower alkyl substituted by halogen, or
—(CH$_2$)$_n$—NH—(CH$_2$)$_o$-heterocyclyl;
n is 0, 1, 2 or 3
m is 0 or 1; and
o is 1, 2 or 3;
or a pharmaceutically acceptable acid addition salt thereof.

2. A compound of formula I of claim 1, wherein
R$^1$, R$^2$, and R$^3$ are each independently hydrogen or halogen;
R$^4$ is hydrogen or lower alkyl;
R$^5$ is —(CH$_2$)$_m$-aryl or —(CH$_2$)$_m$-5 or 6 membered heteroaryl, each of which is optionally substituted by one or more halogen, cyano, nitro, lower alkyl, lower alkoxy, lower alkylsulfanyl, lower alkyl substituted by halogen, —(CO)-lower alkyl, —(CO)—O-lower alkyl, or —NH—(CO)—O-lower alkyl;
R$^6$ is hydrogen, cycloalkyl, aryl, or lower alkyl optionally substituted by lower alkoxy-aryl; and
m is 0 or 1;
or a pharmaceutically acceptable acid addition salt thereof.

3. The compound of claim 1, wherein R$^5$ is —(CH$_2$)$_m$-aryl or —(CH$_2$)$_m$-heteroaryl, each of which is unsubstituted.

4. The compound of claim 3, selected from the group consisting of
5-methyl-3-phenyl-4-(1-phenyl-1H-imidazol-4-yl)-isoxazole,
2-[4-(5-methyl-3-phenyl-isoxazol-4-yl)-imidazol-1-yl]-pyridine,
2-[4-(5-Methyl-3-phenyl-isoxazol-4-yl)-imidazol-1-yl]-pyridine,
2-[4-(5-methyl-3-phenyl-isoxazol-4-yl)-imidazol-1-yl]-pyrimidine,
4-(1-benzyl-1H-imidazol-4-yl)-5-methyl-3-phenyl-isoxazole,
2-{4-[3-(2-fluoro-phenyl)-5-methyl-isoxazol-4-yl]-imidazol-1-yl}-pyrimidine,
2-{4-[3-(3-fluoro-phenyl)-5-methyl-isoxazol-4-yl]-imidazol-1-yl}-pyrimidine,
2-{4-[3-(4-fluoro-phenyl)-5-methyl-isoxazol-4-yl]-imidazol-1-yl}-pyrimidine,
2-{4-[3-(4-bromo-phenyl)-5-methyl-isoxazol-4-yl]-imidazol-1-yl}-pyrimidine, and
4-(1-benzyl-1H-imidazol-4-yl)-3-(4-bromo-phenyl)-5-methyl-isoxazole.

5. The compound of claim 3, selected from the group consisting of
2-{4-[3-(3,4-difluoro-phenyl)-5-methyl-isoxazol-4-yl]-imidazol-1-yl}-pyrimidine,
2-[2-methyl-4-(5-methyl-3-phenyl-isoxazol-4-yl)-imidazol-1-yl]-pyrimidine,
2-[2-benzyloxymethyl-4-(5-methyl-3-phenyl-isoxazol-4-yl)-imidazol-1-yl]-pyrimidine,
4-(1-benzyl-2-benzyloxymethyl-1H-imidazol-4-yl)-5-methyl-3-phenyl-isoxazole,
4-{4-[3-(4-fluoro-phenyl)-5-methyl-isoxazol-4-yl]-imidazol-1-yl}-pyridine,
3-{4-[3-(4-fluoro-phenyl)-5-methyl-isoxazol-4-yl]-imidazol-1-yl}-pyridine,
[3-phenyl-4-(1-phenyl-1H-imidazol-4-yl)-isoxazol-5-yl]-methanol,
4-(5-methyl-3-phenyl-isoxazol-4-yl)-1-phenyl-1H-imidazole-2-carboxylic acid methyl ester and
4-(2-benzyloxymethyl-1-phenyl-1H-imidazol-4-yl)-5-methyl-3-phenyl-isoxazole.

6. The compound of claim 1, wherein R$^5$ is —(CH$_2$)$_m$-aryl or —(CH$_2$)$_m$-heteroaryl, each of which is substituted by one or more halogen.

7. The compound of claim 6, selected from the group consisting of:
4-[1-(4-fluoro-phenyl)-1H-imidazol-4-yl]-5-methyl-3-phenyl-isoxazole,
4-[1-(3-fluoro-phenyl)-1H-imidazol-4-yl]-5-methyl-3-phenyl-isoxazole,
4-[1-(3-chloro-phenyl)-1H-imidazol-4-yl]-5-methyl-3-phenyl-isoxazole,
4-[1-(4-bromo-phenyl)-1H-imidazol-4-yl]-5-methyl-3-phenyl-isoxazole,
4-[1-(3-bromo-phenyl)-1H-imidazol-4-yl]-5-methyl-3-phenyl-isoxazole,
4-[1-(3,4-difluoro-phenyl)-1H-imidazol-4-yl]-5-methyl-3-phenyl-isoxazole,
4-[1-(3,5-difluoro-phenyl)-1H-imidazol-4-yl]-5-methyl-3-phenyl-isoxazole,
4-[1-(3-chloro-4-fluoro-phenyl)-1H-imidazol-4-yl]-5-methyl-3-phenyl-isoxazole,
4-[1-(3,4-dichloro-phenyl)-1H-imidazol-4-yl]-5-methyl-3-phenyl-isoxazole,
4-[1-(2,4-dichloro-phenyl)-1H-imidazol-4-yl]-5-methyl-3-phenyl-isoxazole, and
4-[1-(2-fluoro-5-methoxy-phenyl)-1H-imidazol-4-yl]-5-methyl-3-phenyl-isoxazole.

8. The compound of claim 6, selected from the group consisting of:
4-[1-(4-fluoro-benzyl)-1H-imidazol-4-yl]-5-methyl-3-phenyl-isoxazole,
4-[1-(2-chloro-phenyl)-1H-imidazol-4-yl]-5-methyl-3-phenyl-isoxazole,
4-[1-(2-bromo-phenyl)-1H-imidazol-4-yl]-5-methyl-3-phenyl-isoxazole,
3-(4-fluoro-phenyl)-4-[1-(4-fluoro-phenyl)-1H-imidazol-4-yl]-5-methyl-isoxazole,
4-[1-(4-bromo-phenyl)-1H-imidazol-4-yl]-3-(4-fluoro-phenyl)-5-methyl-isoxazole,
3-(4-fluoro-phenyl)-4-[1-(3-fluoro-phenyl)-1H-imidazol-4-yl]-5-methyl-isoxazole,
4-[1-(3-chloro-phenyl)-1H-imidazol-4-yl]-3-(4-fluoro-phenyl)-5-methyl-isoxazole,
4-[1-(3-bromo-phenyl)-1H-imidazol-4-yl]-3-(4-fluoro-phenyl)-5-methyl-isoxazole,
4-[1-(3,4-difluoro-phenyl)-1H-imidazol-4-yl]-3-(4-fluoro-phenyl)-5-methyl-isoxazole,
4-[1-(3,5-difluoro-phenyl)-1H-imidazol-4-yl]-3-(4-fluoro-phenyl)-5-methyl-isoxazole and
4-[1-(3,5-dichloro-phenyl)-1H-imidazol-4-yl]-3-(4-fluoro-phenyl)-5-methyl-isoxazole.

9. The compound of claim 1, wherein R$^5$ is —(CH$_2$)$_m$-aryl or —(CH$_2$)$_m$-heteroaryl, each of which is substituted by one or more cyano.

10. The compound of claim 9, selected from the group consisting of:
4-[4-(5-methyl-3-phenyl-isoxazol-4-yl)-imidazol-1-yl]-benzonitrile,
3-[4-(5-methyl-3-phenyl-isoxazol-4-yl)-imidazol-1-yl]-benzonitrile,
4-[2-benzyloxymethyl-4-(5-methyl-3-phenyl-isoxazol-4-yl)-imidazol-1-yl]-benzonitrile,
4-{4-[3-(4-fluoro-phenyl)-5-methyl-isoxazol-4-yl]-imidazol-1-yl}-benzonitrile,
3-{4-[3-(4-fluoro-phenyl)-5-methyl-isoxazol-4-yl]-imidazol-1-yl}-benzonitrile and 4-[4-(5-hydroxymethyl-3-phenyl-isoxazol-4-yl)-imidazol-1-yl]-benzonitrile.

11. The compound of claim 1, wherein $R^5$ is —$(CH_2)_m$-aryl or —$(CH_2)_m$-heteroaryl, each of which is substituted by nitro.

12. The compound of claim 11, selected from the group consisting of:
- 5-methyl-4-[1-(4-nitro-phenyl)-1H-imidazol-4-yl]-3-phenyl-isoxazole,
- 3-(2-fluoro-phenyl)-5-methyl-4-[1-(4-nitro-phenyl)-1H-imidazol-4-yl]-isoxazole,
- 3-(3-fluoro-phenyl)-5-methyl-4-[1-(4-nitro-phenyl)-1H-imidazol-4-yl]-isoxazole,
- 3-(3-bromo-phenyl)-5-methyl-4-[1-(4-nitro-phenyl)-1H-imidazol-4-yl]-isoxazole,
- 3-(4-fluoro-phenyl)-5-methyl-4-[1-(4-nitro-phenyl)-1H-imidazol-4-yl]-isoxazole,
- 3-(4-bromo-phenyl)-5-methyl-4-[1-(4-nitro-phenyl)-1H-imidazol-4-yl]-isoxazole,
- 3-(3,4-difluoro-phenyl)-5-methyl-4-[1-(4-nitro-phenyl)-1H-imidazol-4-yl]-isoxazole,
- 5-methyl-4-[2-methyl-1-(4-nitro-phenyl)-1H-imidazol-4-yl]-3-phenyl-isoxazole,
- 4-[2-benzyloxymethyl-1-(4-nitro-phenyl)-1H-imidazol-4-yl]-5-methyl-3-phenyl-isoxazole, and
- 5-methyl-4-[1-(3-nitro-phenyl)-1H-imidazol-4-yl]-3-phenyl-isoxazole.

13. The compound of claim 11, selected from the group consisting of:
- 3-(4-fluoro-phenyl)-5-methyl-4-[1-(4-methyl-3-nitro-phenyl)-1H-imidazol-4-yl]-isoxazole,
- 5-ethyl-3-(4-fluoro-phenyl)-4-[1-(4-nitro-phenyl)-1H-imidazol-4-yl]-isoxazole,
- 5-cyclopropyl-4-[1-(4-nitro-phenyl)-1H-imidazol-4-yl]-3-phenyl-isoxazole,
- [4-(5-methyl-3-phenyl-isoxazol-4-yl)-1-(4-nitro-phenyl)-1H-imidazol-2-yl]-methanol,
- 4-[2-chloromethyl-1-(4-nitro-phenyl)-1H-imidazol-4-yl]-5-methyl-3-phenyl-isoxazole,
- 4-(5-methyl-3-phenyl-isoxazol-4-yl)-1-(4-nitro-phenyl)-1H-imidazole-2-carbaldehyde,
- 5-methyl-4-[2-(4-methyl-benzyloxymethyl)-1-(4-nitro-phenyl)-1H-imidazol-4-yl]-3-phenyl-isoxazole,
- 4-[2-(4-fluoro-benzyloxymethyl)-1-(4-nitro-phenyl)-1H-imidazol-4-yl]-5-methyl-3-phenyl-isoxazole,
- 4-[2-(4-chloro-benzyloxymethyl)-1-(4-nitro-phenyl)-1H-imidazol-4-yl]-5-methyl-3-phenyl-isoxazole, and
- 4-[2-(4-bromo-benzyloxymethyl)-1-(4-nitro-phenyl)-1H-imidazol-4-yl]-5-methyl-3-phenyl-isoxazole.

14. The compound of claim 11, selected from the group consisting of:
- 4-[2-(3-chloro-benzyloxymethyl)-1-(4-nitro-phenyl)-1H-imidazol-4-yl]-5-methyl-3-phenyl-isoxazole,
- 4-[2-(3-fluoro-benzyloxymethyl)-1-(4-nitro-phenyl)-1H-imidazol-4-yl]-5-methyl-3-phenyl-isoxazole,
- 4-[2-(3-bromo-benzyloxymethyl)-1-(4-nitro-phenyl)-1H-imidazol-4-yl]-5-methyl-3-phenyl-isoxazole,
- 4-[2-(2-fluoro-benzyloxymethyl)-1-(4-nitro-phenyl)-1H-imidazol-4-yl]-5-methyl-3-phenyl-isoxazole,
- 2-[4-(5-methyl-3-phenyl-isoxazol-4-yl)-1-(4-nitro-phenyl)-1H-imidazol-2-ylmethoxymethyl]-pyridine,
- 2-methyl-6-[4-(5-methyl-3-phenyl-isoxazol-4-yl)-1-(4-nitro-phenyl)-1H-imidazol-2-ylmethoxymethyl]-pyridine,
- 3-[4-(5-methyl-3-phenyl-isoxazol-4-yl)-1-(4-nitro-phenyl)-1H-imidazol-2-ylmethoxymethyl]-pyridine,
- 5-[4-(5-methyl-3-phenyl-isoxazol-4-yl)-1-(4-nitro-phenyl)-1H-imidazol-2-ylmethoxymethyl]-2-trifluoromethyl-pyridine and
- 4-[4-(5-methyl-3-phenyl-isoxazol-4-yl)-1-(4-nitro-phenyl)-1H-imidazol-2-ylmethoxymethyl]-pyridine.

15. The compound of claim 1, wherein $R^5$ is —$(CH_2)_m$-aryl or —$(CH_2)_m$-heteroaryl, each of which is substituted by lower alkyl.

16. The compound of claim 15, selected from the group consisting of:
- 5-methyl-3-phenyl-4-(1-m-tolyl-1H-imidazol-4-yl)-isoxazole,
- 5-methyl-3-phenyl-4-[1-(4-propyl-phenyl)-1H-imidazol-4-yl]-isoxazole,
- 4-[2-benzyloxymethyl-1-(5-methyl-isoxazol-3-ylmethyl)-1H-imidazol-4-yl]-5-methyl-3-phenyl-isoxazole,
- 5-methyl-4-[1-(5-methyl-isoxazol-3-ylmethyl)-2-phenyl-1H-imidazol-4-yl]-3-phenyl-isoxazole,
- 3-(4-fluoro-phenyl)-5-methyl-4-(1-m-tolyl-1H-imidazol-4-yl)-isoxazole and
- 3-(4-fluoro-phenyl)-5-methyl-4-[1-(4-methyl-3-nitro-phenyl)-1H-imidazol-4-yl]-isoxazole.

17. The compound of claim 1, wherein $R^5$ is —$(CH_2)_m$-aryl or —$(CH_2)_m$-heteroaryl, each of which is substituted by lower alkoxy.

18. The compound of claim 17, selected from the group consisting of:
- 4-[1-(4-methoxy-phenyl)-1H-imidazol-4-yl]-5-methyl-3-phenyl-isoxazole,
- 4-[1-(4-ethoxy-phenyl)-1H-imidazol-4-yl]-5-methyl-3-phenyl-isoxazole,
- 4-[1-(2-ethoxy-phenyl)-1H-imidazol-4-yl]-5-methyl-3-phenyl-isoxazole,
- 4-[1-(2-fluoro-5-methoxy-phenyl)-1H-imidazol-4-yl]-5-methyl-3-phenyl-isoxazole,
- 3-(2-fluoro-phenyl)-4-[1-(4-methoxy-phenyl)-1H-imidazol-4-yl]-5-methyl-isoxazole,
- 3-(3-fluoro-phenyl)-4-[1-(4-methoxy-phenyl)-1H-imidazol-4-yl]-5-methyl-isoxazole and
- 4-[1-(3-ethoxy-phenyl)-1H-imidazol-4-yl]-5-methyl-3-phenyl-isoxazole.

19. The compound of claim 1, wherein $R^5$ is —$(CH_2)_m$-aryl or —$(CH_2)_m$-heteroaryl, each of which is substituted by lower alkylsulfanyl.

20. The compound of claim 19, which is 5-methyl-4-[1-(4-methylsulfanyl-phenyl)-1H-imidazol-4-yl]-3-phenyl-isoxazole.

21. The compound of claim 1, wherein $R^5$ is —$(CH_2)_m$-aryl or —$(CH_2)_m$-heteroaryl, each of which is substituted by lower alkyl substituted by halogen.

22. The compound of claim 21, selected from the group consisting of:
- 5-methyl-3-phenyl-4-[1-(3-trifluoromethyl-phenyl)-1H-imidazol-4-yl]-isoxazole,
- 5-methyl-3-phenyl-4-[1-(4-trifluoromethyl-phenyl)-1H-imidazol-4-yl]-isoxazole,
- 5-methyl-3-phenyl-4-[1-(2-trifluoromethyl-phenyl)-1H-imidazol-4-yl]-isoxazole,
- 4-[1-(3,5-bis-trifluoromethyl-phenyl)-1H-imidazol-4-yl]-5-methyl-3-phenyl-isoxazole,
- 3-(3,4-difluoro-phenyl)-5-methyl-4-[1-(4-trifluoromethyl-phenyl)-1H-imidazol-4-yl]-isoxazole,
- 5-methyl-4-[2-methyl-1-(4-trifluoromethyl-phenyl)-1H-imidazol-4-yl]-3-phenyl-isoxazole,
- 4-[2-benzyloxymethyl-1-(4-trifluoromethyl-phenyl)-1H-imidazol-4-yl]-5-methyl-3-phenyl-isoxazole, 3-(4-fluoro-phenyl)-5-methyl-4-[1-(3-trifluoromethyl-phenyl)-1H-imidazol-4-yl]-isoxazole, and
3-(4-fluoro-phenyl)-5-methyl-4-[1-(2-trifluoromethyl-phenyl)-1H-imidazol-4-yl]-isoxazole.

23. The compound of claim 21, selected from the group consisting of:
5-ethyl-3-(4-fluoro-phenyl)-4-[1-(4-trifluoromethyl-phenyl)-1H-imidazol-4-yl]-isoxazole,
{3-phenyl-4-[1-(4-trifluoromethyl-phenyl)-1H-imidazol-4-yl]-isoxazol-5-yl}-methanol,
{3-(4-fluoro-phenyl)-4-[1-(4-trifluoromethyl-phenyl)-1H-imidazol-4-yl]-isoxazol-5-yl}-methanol,
3-(4-fluoro-phenyl)-5-methoxymethyl-4-[1-(4-trifluoromethyl-phenyl)-1H-imidazol-4-yl]-isoxazole and
4-(5-methyl-3-phenyl-isoxazol-4-yl)-1-(4-trifluoromethyl-phenyl)-1H-imidazole-2-carboxylic acid ethyl ester.

24. The compound of claim 1, wherein $R^5$ is —$(CH_2)_m$-aryl or —$(CH_2)_m$-heteroaryl, each of which is substituted by —(CO)-lower alkyl.

25. The compound of claim 24, selected from the group consisting of:
1-{4-[4-(3-phenyl-isoxazol-4-yl)-imidazol-1-yl]-phenyl}-ethanone,
1-{4-[4-(5-methyl-3-phenyl-isoxazol-4-yl)-imidazol-1-yl]-phenyl}-ethanone,
1-{4-[4-(5-ethyl-3-phenyl-isoxazol-4-yl)-imidazol-1-yl]-phenyl}-ethanone,
5-ethyl-4-[1-(4-nitro-phenyl)-1H-imidazol-4-yl]-3-phenyl-isoxazole,
1-(4-{4-[3-(2-fluoro-phenyl)-5-methyl-isoxazol-4-yl]-imidazol-1-yl}-phenyl)-ethanone,
1-(4-{4-[3-(3-fluoro-phenyl)-5-methyl-isoxazol-4-yl]-imidazol-1-yl}-phenyl)-ethanone,
1-(4-{4-[3-(3-bromo-phenyl)-5-methyl-isoxazol-4-yl]-imidazol-1-yl}-phenyl)-ethanone,
1-(4-{4-[3-(4-fluoro-phenyl)-5-methyl-isoxazol-4-yl]-imidazol-1-yl}-phenyl)-ethanone,
1-(4-{4-[3-(4-bromo-phenyl)-5-methyl-isoxazol-4-yl]-imidazol-1-yl}-phenyl)-ethanone, and
1-(4-{4-[3-(3,4-difluoro-phenyl)-5-methyl-isoxazol-4-yl]-imidazol-1-yl}-phenyl)-ethanone.

26. The compound of claim 24, selected from the group consisting of:
1-{4-[2-methyl-4-(5-methyl-3-phenyl-isoxazol-4-yl)-imidazol-1-yl]-phenyl}-ethanone,
1-{4-[2-benzyloxymethyl-4-(5-methyl-3-phenyl-isoxazol-4-yl)-imidazol-1-yl]-phenyl}-ethanone,
1-(4-{4-[5-ethyl-3-(4-fluoro-phenyl)-isoxazol-4-yl]-imidazol-1-yl}-phenyl)-ethanone,
1-{4-[4-(5-cyclopropyl-3-phenyl-isoxazol-4-yl)-imidazol-1-yl]-phenyl}-ethanone,
1-(4-{4-[3-(4-fluoro-phenyl)-5-hydroxymethyl-isoxazol-4-yl]-imidazol-1-yl}-phenyl)-ethanone and
1-(4-{4-[3-(4-fluoro-phenyl)-5-methoxymethyl-isoxazol-4-yl]-imidazol-1-yl}-phenyl)-ethanone.

27. The compound of claim 1, wherein $R^5$ is —$(CH_2)_m$-aryl or —$(CH_2)_m$-heteroaryl, each of which is substituted by —(CO)—O-lower alkyl.

28. The compound of claim 27, which is
3-[4-(5-methyl-3-phenyl-isoxazol-4-yl)-imidazol-1-yl]-benzoic acid methyl ester,
4-{5-[3-(3-fluoro-phenyl)-5-methyl-isoxazol-4-yl]-imidazol-1-yl}-benzoic acid ethyl ester and
4-{4-[3-(4-fluoro-phenyl)-5-methyl-isoxazol-4-yl]-imidazol-1-yl}-benzoic acid methyl ester.

29. The compound of claim 1, wherein $R^5$ is —$(CH_2)_m$-aryl or —$(CH_2)_m$-heteroaryl, each of which is substituted by —NH—(CO)—O-lower alkyl.

30. The compound of claim 29, which is
{4-[4-(5-methyl-3-phenyl-isoxazol-4-yl)-imidazol-1-yl]-phenyl}-carbamic acid tert-butyl ester.

31. The compound of claim 1, wherein $R^5$ is —$(CH_2)_m$-aryl or —$(CH_2)_m$-heteroaryl, each of which is substituted by —C(O)—NH—R', wherein R' is lower alkynyl or lower alkyl substituted by halogen or hydroxy, or is
—$(CH_2)_n$-cycloalkyl, —$(CH_2)_n$-heterocyclyl, —$(CH_2)_n$-heteroaryl or —$(CH_2)_n$-aryl, each of which is optionally substituted by halogen.

32. The compound of claim 31, selected from the group consisting of:
N-cyclopropylmethyl-4-[4-(5-methyl-3-phenyl-isoxazol-4-yl)-imidazol-1-yl]-benzamide,
4-[4-(5-methyl-3-phenyl-isoxazol-4-yl)-imidazol-1-yl]-N-prop-2-ynyl-benzamide,
4-[4-(5-methyl-3-phenyl-isoxazol-4-yl)-imidazol-1-yl]-N-(3-morpholin-4-yl-propyl)-benzamide,
N-cyclopropyl-4-[4-(5-methyl-3-phenyl-isoxazol-4-yl)-imidazol-1-yl]-benzamide,
N-cyclobutyl-4-[4-(5-methyl-3-phenyl-isoxazol-4-yl)-imidazol-1-yl]-benzamide,
N-cyclopentyl-4-[4-(5-methyl-3-phenyl-isoxazol-4-yl)-imidazol-1-yl]-benzamide,
4-[4-(5-methyl-3-phenyl-isoxazol-4-yl)-imidazol-1-yl]-N-(tetrahydro-pyran-4-yl)-benzamide,
4-[4-(5-methyl-3-phenyl-isoxazol-4-yl)-imidazol-1-yl]-N-pyridin-3-ylmethyl-benzamide,
4-[4-(5-methyl-3-phenyl-isoxazol-4-yl)-imidazol-1-yl]-N-pyridin-4-ylmethyl-benzamide, and
N-(3-fluoro-phenyl)-4-[4-(5-methyl-3-phenyl-isoxazol-4-yl)-imidazol-1-yl]-benzamide.

33. The compound of claim 31, selected from the group consisting of:
N-cyclopropylmethyl-3-[4-(5-methyl-3-phenyl-isoxazol-4-yl)-imidazol-1-yl]-benzamide,
N-cyclopropyl-3-[4-(5-methyl-3-phenyl-isoxazol-4-yl)-imidazol-1-yl]-benzamide,
N-cyclobutyl-3-[4-(5-methyl-3-phenyl-isoxazol-4-yl)-imidazol-1-yl]-benzamide,
N-cyclopentyl-3-[4-(5-methyl-3-phenyl-isoxazol-4-yl)-imidazol-1-yl]-benzamide,
3-[4-(5-methyl-3-phenyl-isoxazol-4-yl)-imidazol-1-yl]-N-(tetrahydro-pyran-4-yl)-benzamide,
N-cyclopropylmethyl-2-[4-(5-methyl-3-phenyl-isoxazol-4-yl)-imidazol-1-yl]-benzamide,
2-[4-(5-methyl-3-phenyl-isoxazol-4-yl)-imidazol-1-yl]-N-prop-2-ynyl-benzamide,
N-cyclobutyl-2-[4-(5-methyl-3-phenyl-isoxazol-4-yl)-imidazol-1-yl]-benzamide,
N-cyclopentyl-2-[4-(5-methyl-3-phenyl-isoxazol-4-yl)-imidazol-1-yl]-benzamide, and
2-[4-(5-methyl-3-phenyl-isoxazol-4-yl)-imidazol-1-yl]-N-(tetrahydro-pyran-4-yl)-benzamide.

34. The compound of claim 31, selected from the group consisting of:

N-cyclopropylmethyl-4-{4-[3-(3-fluoro-phenyl)-5-methyl-isoxazol-4-yl]-imidazol-1-yl}-benzamide,
4-{4-[3-(3-fluoro-phenyl)-5-methyl-isoxazol-4-yl]-imidazol-1-yl}-N-prop-2-ynyl-benzamide,
N-cyclopropyl-4-{4-[3-(3-fluoro-phenyl)-5-methyl-isoxazol-4-yl]-imidazol-1-yl}-benzamide,
N-cyclobutyl-4-{4-[3-(3-fluoro-phenyl)-5-methyl-isoxazol-4-yl]-imidazol-1-yl}-benzamide,
N-cyclopentyl-4-{4-[3-(3-fluoro-phenyl)-5-methyl-isoxazol-4-yl]-imidazol-1-yl}-benzamide,
4-{4-[3-(3-fluoro-phenyl)-5-methyl-isoxazol-4-yl]-imidazol-1-yl}-N-(2-hydroxy-ethyl)-benzamide,
4-{4-[3-(3-fluoro-phenyl)-5-methyl-isoxazol-4-yl]-imidazol-1-yl}-N-(2-morpholin-4-yl-ethyl)-benzamide,
4-{4-[3-(3-fluoro-phenyl)-5-methyl-isoxazol-4-yl]-imidazol-1-yl}-N-(3-morpholin-4-yl-propyl)-benzamide,
4-{4-[3-(3-fluoro-phenyl)-5-methyl-isoxazol-4-yl]-imidazol-1-yl}-N-[2-(1H-imidazol-4-yl)-ethyl]-benzamide, and
4-{4-[3-(3-fluoro-phenyl)-5-methyl-isoxazol-4-yl]-imidazol-1-yl}-N-furan-2-ylmethyl-benzamide.

35. The compound of claim 31, selected from the group consisting of:

4-{4-[3-(3-fluoro-phenyl)-5-methyl-isoxazol-4-yl]-imidazol-1-yl}-N-pyridin-2-ylmethyl-benzamide,
N-(3-fluoro-phenyl)-4-{4-[3-(3-fluoro-phenyl)-5-methyl-isoxazol-4-yl]-imidazol-1-yl}-benzamide,
N-cyclopropylmethyl-3-{4-[3-(3-fluoro-phenyl)-5-methyl-isoxazol-4-yl]-imidazol-1-yl}-benzamide,
N-cyclopropyl-3-{4-[3-(3-fluoro-phenyl)-5-methyl-isoxazol-4-yl]-imidazol-1-yl}-benzamide,
N-cyclobutyl-3-{4-[3-(3-fluoro-phenyl)-5-methyl-isoxazol-4-yl]-imidazol-1-yl}-benzamide,
N-cyclopentyl-3-{4-[3-(3-fluoro-phenyl)-5-methyl-isoxazol-4-yl]-imidazol-1-yl}-benzamide,
3-{4-[3-(3-fluoro-phenyl)-5-methyl-isoxazol-4-yl]-imidazol-1-yl}-N-(tetrahydro-pyran-4-yl)-benzamide;
4-{4-[3-(3-fluoro-phenyl)-5-methyl-isoxazol-4-yl]-imidazol-1-yl}-N-pyridin-3-ylmethyl-benzamide and
N-cyclopentyl-4-{4-[3-(4-fluoro-phenyl)-5-methyl-isoxazol-4-yl]-imidazol-1-yl}-benzamide.

36. A pharmaceutical composition comprising an aryl-isoxazol-4-yl-imidazole derivative of formula I:

wherein $R^1$, $R^2$, and $R^3$ are each independently hydrogen or halogen;

$R^4$ is hydrogen, lower alkyl, cycloalkyl, —$(CH_2)_n$—O-lower alkyl or lower alkyl substituted by hydroxy;

$R^5$ is —$(CH_2)_m$-aryl or —$(CH_2)_m$-heteroaryl, each of which is optionally substituted by one or more substituents selected from the group consisting of halogen, cyano, nitro, lower alkyl, lower alkoxy, lower alkylsulfanyl, lower alkyl substituted by halogen, —C(O)-lower alkyl, —C(O)—O-lower alkyl, —NH—C(O)—O-lower alkyl and —C(O)—NH—R', wherein R' is lower alkynyl or is lower alkyl substituted by halogen, or is —$(CH_2)_n$-cycloalkyl, —$(CH_2)_n$-heterocyclyl, —$(CH_2)_n$-heteroaryl or —$(CH_2)_n$-aryl, each of which is optionally substituted by halogen;

$R^6$ is hydrogen,
—C(O)H,
—$(CH_2)_n$—O-lower alkyl,
—C(O)O-lower alkyl,
lower alkyl substituted by hydroxy or halogen,
cycloalkyl,
aryl,
—$(CH_2)_n$—O—$CH_2$-aryl, optionally substituted by halogen or lower alkyl,
—$(CH_2)_n$—O—$CH_2$-heteroaryl, optionally substituted by halogen, lower alkyl or lower alkyl substituted by halogen, or
—$(CH_2)_n$—NH—$(CH_2)_o$-heterocyclyl;

n is 0, 1, 2 or 3
m is 0 or 1; and
o is 1, 2 or 3;
or a pharmaceutically acceptable acid addition salt thereof and a pharmaceutically acceptable carrier.

* * * * *